(12) United States Patent
Olsen et al.

(10) Patent No.: US 11,598,769 B2
(45) Date of Patent: Mar. 7, 2023

(54) OLIGOMERIZED PROTEIN-POLYMER CONJUGATES

(71) Applicant: Massachusetts Institute of Technology, Cambridge, MA (US)

(72) Inventors: Bradley David Olsen, Arlington, MA (US); Hadley Sikes Johnson, Arlington, MA (US); Eric Alexander Miller, Cambridge, MA (US); Justin Paloni, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 457 days.

(21) Appl. No.: 16/523,209

(22) Filed: Jul. 26, 2019

(65) Prior Publication Data
US 2020/0057058 A1    Feb. 20, 2020

Related U.S. Application Data

(60) Provisional application No. 62/711,440, filed on Jul. 27, 2018.

(51) Int. Cl.
*G01N 33/543* (2006.01)

(52) U.S. Cl.
CPC . *G01N 33/54353* (2013.01); *G01N 33/54366* (2013.01)

(58) Field of Classification Search
CPC ....... G01N 33/54353; G01N 33/54366; C07K 17/08
See application file for complete search history.

(56) References Cited

U.S. PATENT DOCUMENTS

| 4,208,479 | A  | * | 6/1980  | Zuk ..................... C07J 41/0016 436/826 |
| 2009/0324593 | A1 | * | 12/2009 | Johnson ........... G01N 33/56983 424/133.1 |
| 2013/0280782 | A1 |   | 10/2013 | Olsen et al. |
| 2013/0344567 | A1 | * | 12/2013 | Boschetti ............... C07H 21/04 536/23.1 |
| 2014/0024722 | A1 |   | 1/2014  | Olsen et al. |
| 2016/0272960 | A1 | * | 9/2016  | Thanos .......... C12Y 305/04004 |

OTHER PUBLICATIONS

Shimizu (Cancer Science 2014 105:1056-1062). (Year: 2014).*
Ackerman et al., Highly avid magnetic bead capture: an efficient selection method for de novo protein engineering utilizing yeast surface display. Biotechnol Prog. May-Jun. 2009;25(3):774-83. doi: 10.1002/btpr.174.
Bahadir et al., Lateral flow assays: Principles, designs and labels. TrAC Trends Anal Chem. Sep. 2016;82:286-306. doi: 10.1016/j.trac.2016.06.006.

(Continued)

*Primary Examiner* — Changhwa J Cheu
(74) *Attorney, Agent, or Firm* — Wolf, Greenfield & Sacks, P.C.

(57) ABSTRACT

The present disclosure relates to protein-polymer conjugates comprising an engineered binding oligomer protein and a polymer for detection of a ligand of interest, methods, compositions and kits thereof.

18 Claims, 44 Drawing Sheets

Specification includes a Sequence Listing.

(56) References Cited

OTHER PUBLICATIONS

Balsara et al., Birefringence detection of the order-to-disorder transition in block copolymer liquids. Macromolecules. Jul. 1, 1992;25(15):3896-901. doi: 10.1021/ma00041a011. Epub May 1, 2002.
Boutris et al., Characterization of the LCST behaviour of aqueous poly(N-isopropylacrylamide) solutions by thermal and cloud point techniques. Polymer. May 1997;38(10):2567-70. doi: 10.1016/S0032-3861(97)01024-067.
Chandra et al., Novel multiplex technology for diagnostic characterization of rheumatoid arthritis. Arthritis Res Ther. Jun. 24, 2011;13(3):R102, 13 pages, doi: 10.1186/ar3383.
Chang et al., Effect of polymer chemistry on globular protein-polymer block copolymer self-assembly. Polym Chem. 2014;5(17):4884-95. doi: 10.1039/C4PY00448E.
Chang et al., Kinetic Effects on Self-Assembly and Function of Protein-Polymer Bioconjugates in Thin Films Prepared by Flow Coating. Macromol Rapid Commun. Jan. 2017;38(1):6 pages. doi: 10.1002/marc.201600449. Epub Nov. 4, 2016.
Demonte et al., Structure-based engineering of streptavidin monomer with a reduced biotin dissociation rate. Proteins. Sep. 2013;81(9):1621-33. doi: 10.1002/prot.24320. Epub Jun. 17, 2013.
Dixit et al., Multisubstrate-compatible ELISA procedures for rapid and high-sensitivity immunoassays. Nat Protoc. Apr. 2011;6(4):439-45. doi: 10.1038/nprot.2011.304. Epub Mar. 10, 2011.
Dong et al., Three-Dimensional Ordered Antibody Arrays Through Self-Assembly of Antibody-Polymer Conjugates. Angew Chem Int Ed Engl. Jan. 24, 2017;56(5):1273-7. doi: 10.1002/anie.201607085. Epub Dec. 28, 2016.
Dubacheva et al., Controlling Multivalent Binding through Surface Chemistry: Model Study on Streptavidin. J Am Chem Soc. Mar. 22, 2017;139(11):4157-67. doi: 10.1021/jacs.7b00540. Epub Mar. 9, 2017.
Frenzel et al., Expression of Recombinant Antibodies. Front Immunol. Jul. 29, 2013;4:217, 20 pages, doi: 10.3389/fimmu.2013.00217. eCollection 2013.
Gonzales-Sapienza et al., Single-Domain Antibodies as Versatile Affinity Reagents for Analytic and Diagnostic Applications. Front Immunol. Aug. 21, 2017;8:977, 12 pages, doi: 10.3389/fimmu.2017.00977. eCollection 2017.
Hanley et al., Phase Behavior of a Block Copolymer in Solvents of Varying Selectivity. Macromol. Aug. 8, 2000;33(16):5918-31. doi: 10.1021/ma000318b.
Hashimoto et al., Ordered structure in block polymer solutions. 4. Scaling rules on size of fluctuations with block molecular weight, concentration, and temperature in segregation and homogeneous regimes. Macromol. Jul. 1, 1983;16(7):1093-101. doi: 10.1021/ma00241a010. Epub May 1, 2002.
Ho et al., Ultrasensitive electrochemical detection of biotin using electrically addressable site-oriented antibody immobilization approach via aminophenyl boronic acid. Biosens Bioelectron. Nov. 15, 2010;26(3):1021-7. doi: 10.1016/j.bios.2010.08.048.
Huang et al., Highly Active Biocatalytic Coatings from Protein-Polymer Diblock Copolymers. ACS Appl Mater Interfaces. Jul. 15, 2015;7(27): 14660-9. doi: 10.1021/acsami.5b01884. Epub Jul. 2, 2015.
Huang et al., Self-Consistent Calculations of Block Copolymer Solution Phase Behavior. Macromol. Jun. 1, 1998;31(11):3556-65. doi: 10.1021/ma980007p. Epub May 15, 1998.
Kalichuk et al., The archaeal "7 kDa DNA-binding" proteins: extended characterization of an old gifted family. Sci Rep. Nov. 17, 2016;6:37274, 10 pages, doi: 10.1038/srep37274.
Kim et al., Protein immobilization techniques for microfluidic assays. Biomicrofluidics. Jul. 30, 2013;7(4):41501, 47 pages, doi: 10.1063/1.4816934. eCollection 2013.
Lai et al., Scaling of Domain Spacing in Concentrated Solutions of Block Copolymers in Selective Solvents. Macromol. May 1, 2002;35(10):4044-9. doi: 10.1021/ma0122223. Epub Apr. 4, 2002.

Lam et al., The Effect of Protein Electrostatic Interactions on Globular Protein-Polymer Block Copolymer Self-Assembly. Biomacromolecules. Sep. 12, 2016;17(9):2820-9. doi: 10.1021/acs.biomac.6b00522. Epub Aug. 2, 2016.
Lam et al., The Nature of Protein Interactions Governing Globular Protein-Polymer Block Copolymer Self-Assembly. Biomacromol. 2014;15(4):1248-58. doi: 10.1021/bm401817p.
Lam et al., Phase transitions in concentrated solution self-assembly of globular protein-polymer block copolymers. Soft Matter. Jan. 2013;9(8):2393-402. doi: 10.1039/C2SM27459K.
Lessard et al., Effect of the molecular weight on the lower critical solution temperature of poly(N,N-diethylacrylamide) in aqueous solutions. Can J Chem. 2001;79(12):1870-4. doi: 10.1139/v01-180.
Li et al., A nanobody-based electrochemiluminescent immunosensor for sensitive detection of human procalcitonin. Analyst. 2014;139(15):3718-21. doi: 10.1039/C4AN00626G.
Li et al., Multiplexed lateral flow biosensors: Technological advances for radically improving point-of-care diagnoses. Biosens Bioelectron. Sep. 15, 2016;83:177-92. doi: 10.1016/j.bios.2016.04.021. Epub Apr. 8, 2016.
Ling et al., Multiplexing molecular diagnostics and immunoassays using emerging microarray technologies. Expert Rev Mol Diagn. Jan. 2007;7(1):87-98. doi: 10.1586/14737159.7.1.87.
Lodge et al., Phase Behavior of Block Copolymers in a Neutral Solvent. Macromol. Jan. 7, 2003;36(3):816-22. doi: 10.1021/ma0209601. Epub Feb. 1, 2003.
Lodge et al., Solvent Distribution in Weakly-Ordered Block Copolymer Solutions. Macromol. 1997;30(20):6139-49. doi: 10.1021/ma970720z.
Lodge et al., The Full Phase Behavior for Block Copolymers in Solvents of Varying Selectivity. Macromol. 2002;35(12):4707-17. doi: 10.1021/ma0200975.
Makaraviciute et al., Site-directed antibody immobilization techniques for immunosensors. Biosens Bioelectron. Dec. 15, 2013;50:460-71. doi: 10.1016/j.bios.2013.06.060. Epub Jul. 5, 2013.
McConnell et al., Melting of Ordered Arrays and Shape Transitions in Highly Concentrated Diblock Copolymer Solutions. Macromol. 1997;30(3):435-44. doi: 10.1021/ma961241n.
Miller et al., Paper-based diagnostics in the antigen-depletion regime: High-density immobilization of rcSso7d-cellulose-binding domain fusion proteins for efficient target capture. Biosens Bioelectron. Apr. 15, 2018; 102:456-463. doi: 10.1016/j.bios.2017.11.050. Epub Nov. 20, 2017.
Miller et al., Activity-based assessment of an engineered hyperthermophilic protein as a capture agent in paper-based diagnostic tests. Mol Syst Des Eng. Dec. 1, 2016;1(4):377-381. doi: 10.1039/C6ME00032K. Epub Jun. 29, 2016.
Miranda et al., Reagentless fluorescent biosensors from artificial families of antigen binding proteins. Biosens Bioelectron. 2011;26(10):4184-90. doi: 10.1016/j.bios.2011.04.030.
Myers et al., Innovations in optical microfluidic technologies for point-of-care diagnostics. Lab Chip. Dec. 2008;8(12):2015-31. doi: 10.1039/b812343h. Epub Oct. 30, 2008.
Olsen et al., Phase Transitions in Asymmetric Rod-Coil Block Copolymers. Macromol. Oct. 1, 2006;39(20):7078-83. doi: 10.1021/ma060994z. Epub Sep. 12, 2006.
Olsen et al., Universalization of the Phase Diagram for a Model Rod-Coil Diblock Copolymer. Macromol. Sep. 23, 2008;41(18):6809-17. doi: 10.1021/ma800978c. Epub Aug. 19, 2008.
Paloni et al., Improved Ordering in Low Molecular Weight Protein-Polymer Conjugates Through Oligomerization of the Protein Block. Biomacromolecules. Sep. 10, 2018;19(9):3814-3824. doi: 10.1021/acs.biomac.8b00928. Epub Aug. 22, 2018.
Peluso et al., Optimizing antibody immobilization strategies for the construction of protein microarrays. Anal Biochem. Jan. 15, 2003;312(2):113-24.
Perez-Luna et al., Molecular Recognition between Genetically Engineered Streptavidin and Surface-Bound Biotin. J Am Chem Soc. Jul. 1, 1999;121(27):6469-78. doi: 10.1021/ja983984p. Epub Jun. 19, 1999.
Qin et al., Topological Effects on Globular Protein-ELP Fusion Block Copolymer Self-Assembly. Adv Funct Mater. 2015;25(5):729-38. doi: 10.1002/adfm.201403453.

(56) References Cited

OTHER PUBLICATIONS

Quesada-Gonzalez et al., Nanoparticle-based lateral flow biosensors. Biosens Bioelectron. Nov. 15, 2015;73:47-63. doi: 10.1016/j.bios.2015.05.050. Epub May 25, 2015.

Renberg et al., Affibody Molecules in Protein Capture Microarrays: Evaluation of Multidomain Ligands and Different Detection Formats. J Proteome Res. Jan. 2007;6(1):171-9.

Sajid et al., Designs, formats and applications of lateral flow assay: A literature review. J Saudi Chem Soc. 2015;19(6):689-705. doi: 10.1016/j.jscs.2014.09.001.

Shibayama et al., Ordered structure in block polymer solutions. 3. Concentration dependence of microdomains in nonselective solvents. Macromol. Sep. 1, 1983;16(9):1427-33. doi: 10.1021/ma00243a005. Epub May 1, 2002.

Sinem et al., SNAP-tag as a Tool for Surface Immobilization. Curr Pharm Des. 2013;19(30):5443-8.

Squires et al., Making it stick: convection, reaction and diffusion in surface-based biosensors. Nat Biotechnol. Apr. 2008;26(4):417-26. doi: 10.1038/nbt1388.

Thomas et al., Coil fraction-dependent phase behaviour of a model globular protein-polymer diblock copolymer. Soft Matter. May 7, 2014;10(17):3093-102. doi: 10.1039/c3sm52531g.

Thomas et al., Kinetically Controlled Nanostructure Formation in Self-Assembled Globular Protein-Polymer Diblock Copolymers. Biomacromolecules. Sep. 10, 2012;13(9):2781-92. doi: 10.1021/bm300763x. Epub Aug. 28, 2012.

Thomas et al., Solid-State Nanostructured Materials from Self-Assembly of a Globular Protein-Polymer Diblock Copolymer. ACS Nano. Jul. 26, 2011;5(7):5697-707. doi: 10.1021/nn2013673. Epub Jun. 22, 2011.

Traxlmayr et al., Strong Enrichment of Aromatic Residues in Binding Sites from a Charge-neutralized Hyperthermostable Ss07d Scaffold Library. J Biol Chem. Oct. 21, 2016;291(43):22496-508. Epub Aug. 30, 2016.

Vuoriluoto et al., Control of Protein Affinity of Bioactive Nanocellulose and Passivation Using Engineered Block and Random Copolymers. ACS Appl Mater Interfaces. Mar. 2, 2016;8(8):5668-78. Epub Feb. 16, 2016.

Wang et al., Nanobody-Based Electrochemical Immunoassay for Ultrasensitive Determination of Apolipoprotein-A1 Using Silver Nanoparticles Loaded Nanohydroxyapatite as Label. Anal Chem. Nov. 17, 2015;87(22):11209-14. doi: 10.1021/acs.analchem.5b04063. Epub Nov. 6, 2015.

Xia et al., Thermal Response of Narrow-Disperse Poly(N-isopropylacrylamide) Prepared by Atom Transfer Radical Polymerization. Macromol. Jul. 1, 2005;38(14):5937-43. doi: 10.1021/ma050261z. Epub Jun. 15, 2005.

Yang et al., Micro-optics for microfluidic analytical applications. Chem Soc Rev. Jan. 2018;47(4):1391-458. doi: 10.1039/C5CS00649J.

Yetisen et al., Paper-based microfluidic point-of-care diagnostic devices. Lab Chip. Jun. 21, 2013;13(12):2210-51. doi: 10.1039/c3lc50169h. Epub May 8, 2013.

Cracknell et al., Enzymes as Working or Inspirational Electrocatalysts for Fuel Cells and Electrolysis. Chem Rev. 2008;108(7):2439-61. doi: 10.1021/cr0680639.

Kim et al., Protein immobilization techniques for microfluidic assays. Biomicrofluidics. Biomicrofluidics. Jul. 30, 2013;7(4):41501, 47 pages, doi: 10.1063/1.4816934. eCollection 2013.

Ling et al., Multiplexing molecular diagnostics and immunoassays using emerging microarray technologies. Expert Rev Mol Diagn. Jan. 2007;7(1):87-98.

Sajid et al., Designs, formats and applications of lateral flow assay: A literature review. J Saudi Chem Soc. Nov. 2015;19(6):689-705. doi: 10.1016/j.jscs.2014.09.001.

Yang et al., Micro-optics for microfluidic analytical applications. Chem Soc Rev. 2018;47(4):1391-458. doi: 10.1039/C5CS00649J.

PCT/US2019/043601, Dec. 4, 2019, International Search Report and Written Opinion.

PCT/US2019/043601, Feb. 11, 2021, International Preliminary Report on Patentability.

PCT/US2019/043601, Sep. 30, 2019, Invitation to Pay Additional Fees.

* cited by examiner

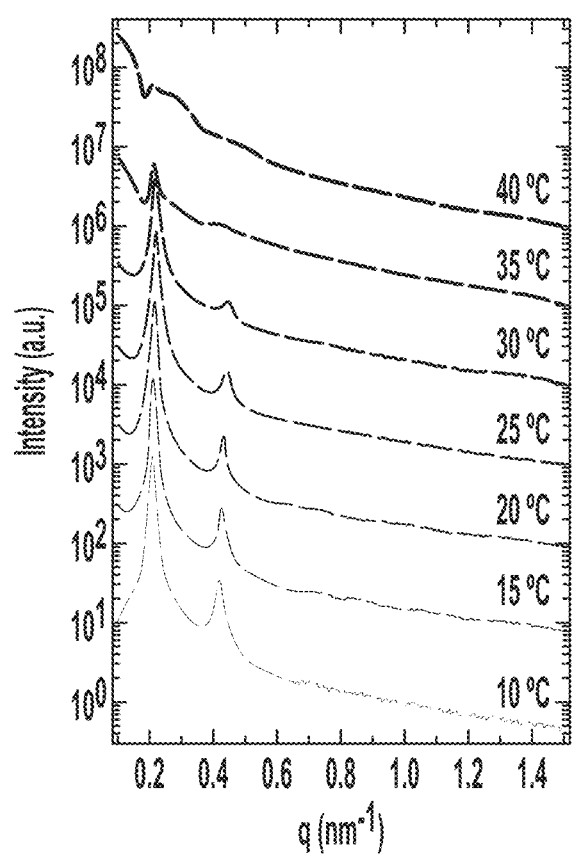
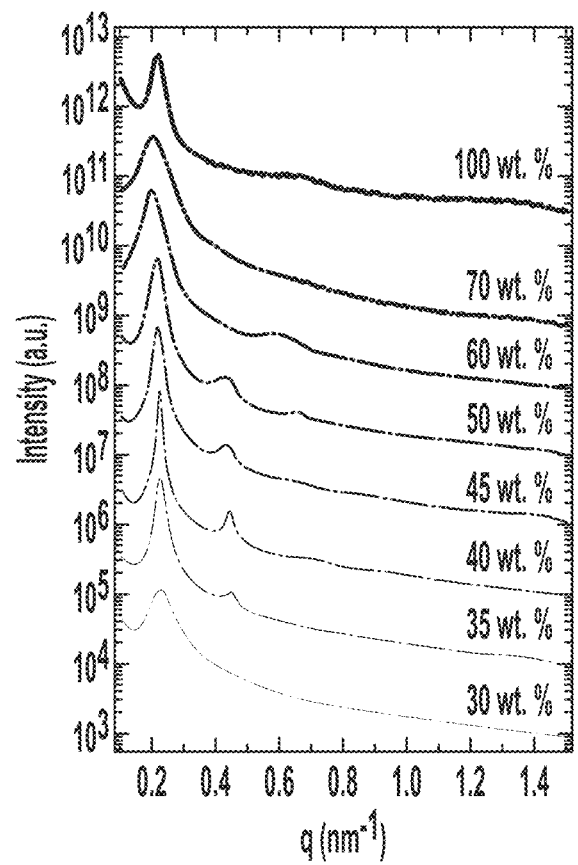
FIG. 3A
FIG. 3B

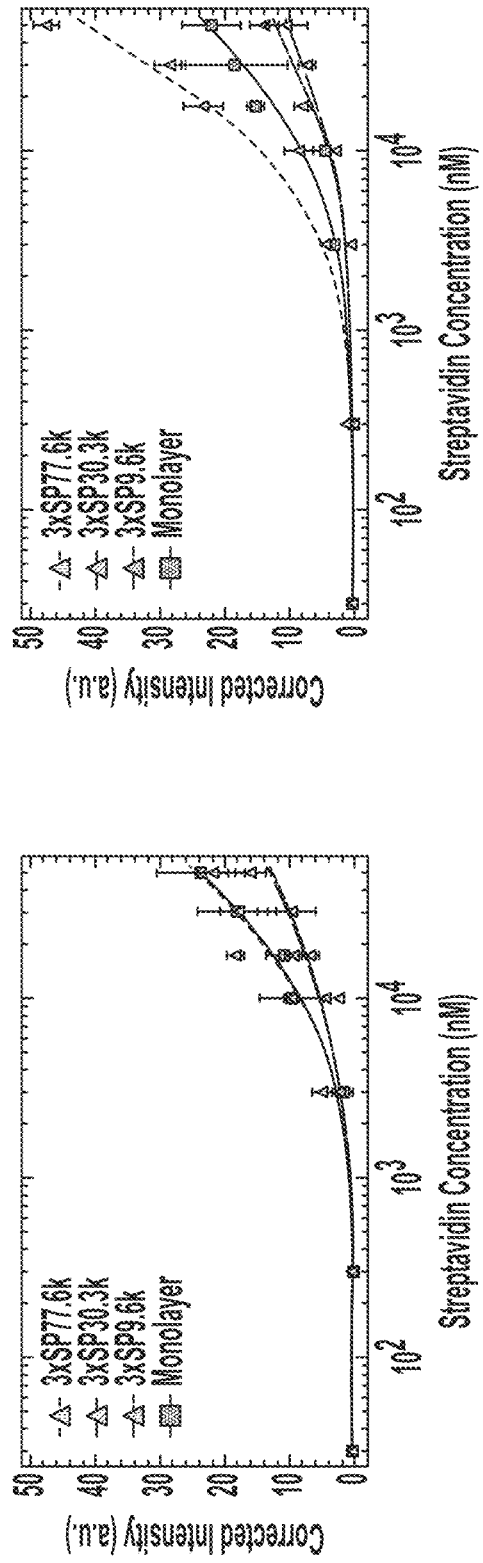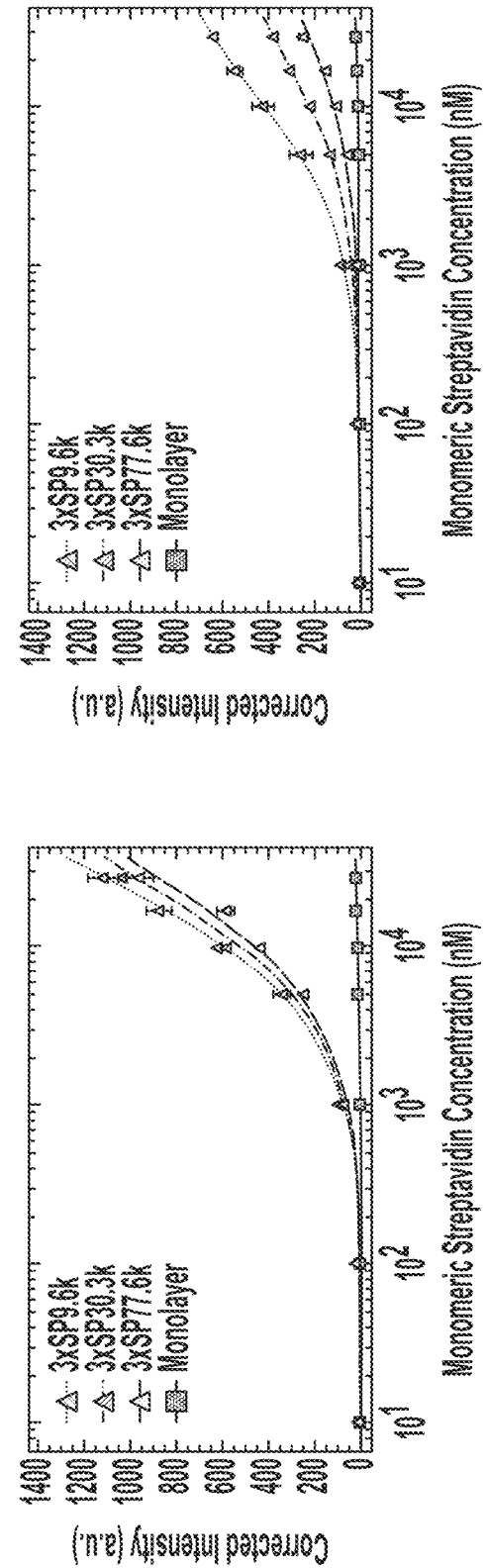
FIG. 27A
FIG. 27B
FIG. 27C
FIG. 27D

SEQUENCE LISTING

<160> NUMBER OF SEQ ID NOS: 40

<210> SEQ ID NO 1
<211> LENGTH: 64
<212> TYPE: PRT
<213> ORGANISM: Sulfolobus solfataricus

<400> SEQUENCE: 1

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 2
<211> LENGTH: 62
<212> TYPE: PRT
<213> ORGANISM: Sulfolobus solfataricus

<400> SEQUENCE: 2

Met Ala Thr Val Lys Phe Thr Tyr Gln Gly Glu Glu Lys Gln Val Asp
1               5                   10                  15

Ile Ser Lys Ile Lys Lys Val Trp Arg Val Gly Gln Met Ile Ser Phe
            20                  25                  30

Thr Tyr Asp Glu Gly Gly Gly Ala Thr Gly Arg Gly Ala Val Ser Glu
        35                  40                  45

Lys Asp Ala Pro Lys Glu Leu Leu Gln Met Leu Glu Lys Gln
    50                  55                  60

<210> SEQ ID NO 3
<211> LENGTH: 64
<212> TYPE: PRT
<213> ORGANISM: Sulfolobus solfataricus

<400> SEQUENCE: 3

Met Ala Thr Val Lys Phe Lys Tyr Lys Gly Glu Glu Lys Gln Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60

<210> SEQ ID NO 4
<211> LENGTH: 66
<212> TYPE: PRT
<213> ORGANISM: Sulfolobus acidocaldarius

<400> SEQUENCE: 4

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
        50                  55                  60

Lys Lys
 65

<210> SEQ ID NO 5
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 5

Gly Gly Gly Gly Ser Gly Gly Gly Gly Ser Gly Gly Gly Gly Ser
 1               5                  10                  15

<210> SEQ ID NO 6
<211> LENGTH: 62
<212> TYPE: PRT
<213> ORGANISM: Artificial Sequence
<220> FEATURE:
<223> OTHER INFORMATION: Synthetic Polypeptide

<400> SEQUENCE: 6

Met Ala Thr Val Lys Phe Thr Tyr Gln Gly Glu Glu Lys Gln Val Asp
 1               5                  10                  15

Ile Ser Lys Ile Lys Ile Val Ala Arg Asp Gly Gln Tyr Ile Asp Phe
            20                  25                  30

Lys Tyr Asp Glu Gly Gly Gly Ala Tyr Gly Tyr Gly Trp Val Ser Glu
        35                  40                  45

Lys Asp Ala Pro Lys Glu Leu Leu Gln Met Leu Glu Lys Gln
        50                  55                  60

<210> SEQ ID NO 7
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 7

Met Ala Thr Val Lys Phe Thr Tyr Gln Gly Glu Glu Lys Gln Val Asp
 1               5                  10                  15

Ile Ser Lys Ile Lys Tyr Val Tyr Arg Trp Gly His Tyr Ile Tyr Phe
            20                  25                  30

Trp Tyr Asp Glu Gly Gly Gly Ala Ser Gly Trp Gly Val Ser Glu
        35                  40                  45

Lys Asp Ala Pro Lys Glu Leu Leu Gln
        50                  55

<210> SEQ ID NO 8
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 8

Met Ala Thr Val Lys Phe Thr Tyr Gln Gly Glu Glu Lys Gln Val Asp
 1               5                  10                  15

Ile Ser Lys Ile Lys His Val Arg Arg Trp Gly Gln Trp Ile Tyr Phe
            20                  25                  30

-continued

Ile Tyr Asp Glu Gly Gly Gly Ala Arg Gly Asn Gly Tyr Val Ser Glu
            35                  40                  45

Lys Asp Ala Pro Lys Glu Leu Leu Gln
    50                  55

<210> SEQ ID NO 9
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 9

Met Ala Thr Val Lys Phe Thr Tyr Gln Gly Glu Glu Lys Gln Val Asp
1               5                   10                  15

Ile Ser Lys Ile Lys Arg Val Arg Arg Tyr Gly Gln Trp Ile Ala Phe
            20                  25                  30

His Tyr Asp Glu Gly Gly Gly Ala Ala Gly Trp Gly Tyr Val Ser Glu
            35                  40                  45

Lys Asp Ala Pro Lys Glu Leu Leu Gln
    50                  55

<210> SEQ ID NO 10
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 10

Met Ala Thr Val Lys Phe Thr Tyr Gln Gly Glu Glu Lys Gln Val Asp
1               5                   10                  15

Ile Ser Lys Ile Lys Trp Val Trp Arg Gly Gly Gln Gly Ile Ile Phe
            20                  25                  30

Trp Tyr Asp Glu Gly Gly Gly Ala Arg Gly Tyr Gly Arg Val Ser Glu
            35                  40                  45

Lys Asp Ala Pro Lys Glu Leu Leu Gln
    50                  55

<210> SEQ ID NO 11
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 11

Met Ala Thr Val Lys Phe Thr Tyr Gln Gly Glu Glu Lys Gln Val Asp
1               5                   10                  15

Ile Ser Lys Ile Lys Arg Val Ile Arg Ile Gly Gln Tyr Ile Tyr Phe
            20                  25                  30

Trp Tyr Asp Glu Gly Gly Gly Ala Arg Gly Trp Gly Tyr Val Ser Glu
            35                  40                  45

Lys Asp Ala Pro Lys Glu Leu Leu Gln
    50                  55

<210> SEQ ID NO 12
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 12

Met Ala Thr Val Lys Phe Thr Tyr Gln Gly Glu Glu Lys Gln Val Asp
1               5                   10                  15

Ile Ser Lys Ile Lys Trp Val His Arg Trp Gly Gln Arg Ile Arg Phe
                20                  25                  30

Trp Tyr Asp Glu Gly Gly Gly Ala Gly Asn Gly Lys Val Ser Glu
                35                  40                  45

Lys Asp Ala Pro Lys Glu Leu Leu Gln
        50                  55

<210> SEQ ID NO 13
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 13

Met Ala Thr Val Lys Phe Thr Tyr Gln Gly Glu Glu Lys Gln Val Asp
1               5                   10                  15

Ile Ser Lys Ile Lys Trp Val Ile Arg Trp Gly Gln Trp Ile Trp Phe
                20                  25                  30

Lys Tyr Asp Glu Gly Gly Gly Ala Ser Gly Trp Gly Tyr Val Ser Glu
                35                  40                  45

Lys Asp Ala Pro Lys Glu Leu Leu Gln
        50                  55

<210> SEQ ID NO 14
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 14

Met Ala Thr Val Lys Phe Thr Tyr Gln Gly Glu Glu Lys Gln Val Asp
1               5                   10                  15

Ile Ser Lys Ile Lys Arg Val Arg Arg Trp Gly Gln Trp Ile Tyr Phe
                20                  25                  30

Arg Tyr Asp Glu Gly Gly Gly Ala Tyr Gly Ser Gly Tyr Val Ser Glu
                35                  40                  45

Lys Asp Ala Pro Lys Glu Leu Leu Gln
        50                  55

<210> SEQ ID NO 15
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 15

Met Ala Thr Val Lys Phe Thr Tyr Gln Gly Glu Glu Lys Gln Val Asp
1               5                   10                  15

Ile Ser Lys Ile Lys Tyr Val Tyr Arg Trp Gly Gln Trp Ile Tyr Phe
                20                  25                  30

Trp Tyr Asp Glu Gly Gly Gly Ala Trp Gly Arg Gly Tyr Val Ser Glu
                35                  40                  45

Lys Asp Ala Pro Lys Glu Leu Leu Gln

<210> SEQ ID NO 16
<211> LENGTH: 252
<212> TYPE: DNA
<213> ORGANISM: Artificial Sequence
<220> FEATURE:
<223> OTHER INFORMATION: Synthetic Polynucleotide

<400> SEQUENCE: 16

```
atgggcagca tccatcatca tcatcatcac agcagcggcc tggtgccgcg cggcagccat      60
atgtgtgcaa ccgtgaaatt cacataccaa ggcgaagaaa aacaggtgga tattagcaaa     120
atcaagatcg tggctcgtga cggccagtac attgacttta aatatgatga aggtggtggt     180
gcctatggtt atggtgggt gagcgaaaaa gatgcaccga agaactgct gcagatgctg       240
gaaaagcaat aa                                                         252
```

<210> SEQ ID NO 17
<211> LENGTH: 83
<212> TYPE: PRT
<213> ORGANISM: Artificial Sequence
<220> FEATURE:
<223> OTHER INFORMATION: Synthetic Polypeptide

<400> SEQUENCE: 17

Met Gly Ser Ile His His His His His His Ser Ser Gly Leu Val Pro
1               5                   10                  15

Arg Gly Ser His Met Cys Ala Thr Val Lys Phe Thr Tyr Gln Gly Glu
            20                  25                  30

Glu Lys Gln Val Asp Ile Ser Lys Ile Lys Ile Val Ala Arg Asp Gly
        35                  40                  45

Gln Tyr Ile Asp Phe Lys Tyr Asp Glu Gly Gly Ala Tyr Gly Tyr
    50                  55                  60

Gly Trp Val Ser Glu Lys Asp Ala Pro Lys Glu Leu Leu Gln Met Leu
65                  70                  75                  80

Glu Lys Gln

<210> SEQ ID NO 18
<211> LENGTH: 474
<212> TYPE: DNA
<213> ORGANISM: Artificial Sequence
<220> FEATURE:
<223> OTHER INFORMATION: Synthetic Polynucleotide

<400> SEQUENCE: 18

```
atgggcagca gccatcatca tcatcatcac agcagcggcc tggtgccgcg cggcagccat      60
atgtgtgcaa ccgtgaaatt cacataccaa ggcgaagaaa aacaggtgga tattagcaaa     120
atcaagatcg tggctcgtga cggccagtac attgacttta aatatgatga aggtggtggt     180
gcctatggtt atggtgggt gagcgaaaaa gatgcaccga agaactgct gcagatgctg       240
gaaaagcaag tggtggtgg tagcggtggt ggcggttcaa tggcaaccgt gaaattcaca      300
taccaaggcg aagaaaaaca ggtggatatt agcaaaatca gatcgtggc tcgtgacggc      360
cagtacattg actttaaata tgatgaaggt ggtggtgcct atggttatgg ttgggtgagc     420
gaaaaagatg caccgaaaga actgctgcag atgctggaaa gcaaggtgg ataa            474
```

<210> SEQ ID NO 19
<211> LENGTH: 157
<212> TYPE: PRT

<213> ORGANISM: Artificial Sequence
<220> FEATURE:
<223> OTHER INFORMATION: Synthetic Polypeptide

<400> SEQUENCE: 19

```
Met Gly Ser Ser His His His His His His Ser Ser Gly Leu Val Pro
1               5                   10                  15
Arg Gly Ser His Met Cys Ala Thr Val Lys Phe Thr Tyr Gln Gly Glu
            20                  25                  30
Glu Lys Gln Val Asp Ile Ser Lys Ile Lys Ile Val Ala Arg Asp Gly
        35                  40                  45
Gln Tyr Ile Asp Phe Lys Tyr Asp Glu Gly Gly Ala Tyr Gly Tyr
    50                  55                  60
Gly Trp Val Ser Glu Lys Asp Ala Pro Lys Glu Leu Leu Gln Met Leu
65                  70                  75                  80
Glu Lys Gln Gly Gly Gly Ser Gly Gly Gly Ser Met Ala Thr
                85                  90                  95
Val Lys Phe Thr Tyr Gln Gly Glu Glu Lys Gln Val Asp Ile Ser Lys
                100                 105                 110
Ile Lys Ile Val Ala Arg Asp Gly Gln Tyr Ile Asp Phe Lys Tyr Asp
            115                 120                 125
Glu Gly Gly Gly Ala Tyr Gly Tyr Gly Trp Val Ser Glu Lys Asp Ala
        130                 135                 140
Pro Lys Glu Leu Leu Gln Met Leu Glu Lys Gln Gly Gly
145                 150                 155
```

<210> SEQ ID NO 20
<211> LENGTH: 690
<212> TYPE: DNA
<213> ORGANISM: Artificial Sequence
<220> FEATURE:
<223> OTHER INFORMATION: Synthetic Polynucleotide

<400> SEQUENCE: 20

```
atgggcagca gccatcatca tcatcatcac agcagcggcc tggtgccgcg cggcagccat    60
atgtgtgcaa ccgtgaaatt cacataccaa ggcgaagaaa acaggtgga tattagcaaa   120
atcaagatcg tggctcgtga cggccagtac attgacttta aatatgatga aggtggtggt   180
gcctatggtt atggttgggt gagcgaaaaa gatgcaccga agaactgct gcagatgctg   240
gaaaagcaag gtggtggtgg tagcggtggt ggcggttcaa tggcaaccgt gaaattcaca   300
taccaaggcg aagaaaaaca ggtggatatt agcaaaatca gatcgtggc tcgtgacggc   360
cagtacattg actttaaata tgatgaaggt ggtggtgcct atggttatgg ttgggtgagc   420
gaaaagatg caccgaaaga actgctgcag atgctggaaa agcaaggtgg tggtggtagc   480
ggtggtggcg gttcaatggc aaccgtgaaa ttcacatacc aaggcgaaga aaaacaggtg   540
gatattagca aaatcaagat cgtggctcgt gacggccagt acattgactt taaatatgat   600
gaaggtggtg gtgcctatgg atatggttgg gtgagcgaaa agatgcacc gaaagaactg   660
ctgcagatgc tggaaaagca aggtggataa                                    690
```

<210> SEQ ID NO 21
<211> LENGTH: 229
<212> TYPE: PRT
<213> ORGANISM: Artificial Sequence
<220> FEATURE:
<223> OTHER INFORMATION: Synthetic Polypeptide

<400> SEQUENCE: 21

```
Met Gly Ser Ser His His His His His Ser Ser Gly Leu Val Pro
1               5                   10                  15

Arg Gly Ser His Met Cys Ala Thr Val Lys Phe Thr Tyr Gln Gly Glu
            20                  25                  30

Glu Lys Gln Val Asp Ile Ser Lys Ile Lys Ile Val Ala Arg Asp Gly
            35                  40                  45

Gln Tyr Ile Asp Phe Lys Tyr Asp Glu Gly Gly Ala Tyr Gly Tyr
    50                  55                  60

Gly Trp Val Ser Glu Lys Asp Ala Pro Lys Glu Leu Leu Gln Met Leu
65                  70                  75                  80

Glu Lys Gln Gly Gly Gly Ser Gly Gly Gly Ser Met Ala Thr
            85                  90                  95

Val Lys Phe Thr Tyr Gln Gly Glu Glu Lys Gln Val Asp Ile Ser Lys
            100                 105                 110

Ile Lys Ile Val Ala Arg Asp Gly Gln Tyr Ile Asp Phe Lys Tyr Asp
            115                 120                 125

Glu Gly Gly Gly Ala Tyr Gly Tyr Gly Trp Val Ser Glu Lys Asp Ala
    130                 135                 140

Pro Lys Glu Leu Leu Gln Met Leu Glu Lys Gln Gly Gly Gly Ser
145                 150                 155                 160

Gly Gly Gly Gly Ser Met Ala Thr Val Lys Phe Thr Tyr Gln Gly Glu
            165                 170                 175

Glu Lys Gln Val Asp Ile Ser Lys Ile Lys Ile Val Ala Arg Asp Gly
            180                 185                 190

Gln Tyr Ile Asp Phe Lys Tyr Asp Glu Gly Gly Gly Ala Tyr Gly Tyr
    195                 200                 205

Gly Trp Val Ser Glu Lys Asp Ala Pro Lys Glu Leu Leu Gln Met Leu
210                 215                 220

Glu Lys Gln Gly Gly
225

<210> SEQ ID NO 22
<211> LENGTH: 900
<212> TYPE: DNA
<213> ORGANISM: Artificial Sequence
<220> FEATURE:
<223> OTHER INFORMATION: Synthetic Polynucleotide

<400> SEQUENCE: 22
atgggcagca gccatcatca tcatcatcac agcagcggcc tggtgccgcg cggcagccat    60
atgtgtgcaa ccgtgaaatt cacataccaa ggcgaagaaa acaggtgga tattagcaaa   120 atcaagatcg tggctcgtga cggccagtac attgacttta aatatgatga aggtggtggt   180
gcctatggtt atggttgggt gagcgaaaaa gatgcaccga agaactgct gcagatgctg   240 gaaaagcaag gtggtggtgg tagcggtggt ggcggttcaa tggcaaccgt gaaattcaca   300
taccaaggcg aagaaaaaca ggtggatatt agcaaaatca gatcgtggc tcgtgacggc   360 cagtacattg actttaaata tgatgaaggt ggtggtgcct atggttatgg ttgggtgagc   420 gaaaagatg caccgaaaga actgctgcag atgctggaaa agcaaggtgg tggtggtagc   480
ggtggtggcg gttcaatggc aaccgtgaaa ttcacatacc aaggcgaaga aaacaggtg   540 gatattagca aaatcaagat cgtggctcgt gacggccagt acattgactt taaatatgat   600
gaaggtggtg gtgcctatgg ttatggttgg gtgagcgaaa agatgcacc gaagaactg   660 ctgcagatgc tggaaaagca aggtggtggt ggtagcggtg gtggcggttc aatggcaacc   720
```

```
gtgaaattca cataccaagg cgaagaaaaa caggtggata ttagcaaaat caagatcgtg      780
gctcgtgacg gccagtacat tgactttaaa tatgatgaaa gtggtggtgc ctatggttat      840
ggttgggtga gcgaaaaaga tgcaccgaaa gaactgctgc agatgctgga aaagcaataa      900
```

<210> SEQ ID NO 23
<211> LENGTH: 299
<212> TYPE: PRT
<213> ORGANISM: Artificial Sequence
<220> FEATURE:
<223> OTHER INFORMATION: Synthetic Polypeptide

<400> SEQUENCE: 23

```
Met Gly Ser Ser His His His His His His Ser Ser Gly Leu Val Pro
1               5                   10                  15

Arg Gly Ser His Met Cys Ala Thr Val Lys Phe Thr Tyr Gln Gly Glu
            20                  25                  30

Glu Lys Gln Val Asp Ile Ser Lys Ile Lys Ile Val Ala Arg Asp Gly
        35                  40                  45

Gln Tyr Ile Asp Phe Lys Tyr Asp Glu Gly Gly Ala Tyr Gly Tyr
    50                  55                  60

Gly Trp Val Ser Glu Lys Asp Ala Pro Lys Glu Leu Leu Gln Met Leu
65                  70                  75                  80

Glu Lys Gln Gly Gly Gly Ser Gly Gly Gly Ser Met Ala Thr
                85                  90                  95

Val Lys Phe Thr Tyr Gln Gly Glu Glu Lys Gln Val Asp Ile Ser Lys
            100                 105                 110

Ile Lys Ile Val Ala Arg Asp Gly Gln Tyr Ile Asp Phe Lys Tyr Asp
        115                 120                 125

Glu Gly Gly Ala Tyr Gly Tyr Gly Trp Val Ser Glu Lys Asp Ala
    130                 135                 140

Pro Lys Glu Leu Leu Gln Met Leu Glu Lys Gln Gly Gly Gly Ser
145                 150                 155                 160

Gly Gly Gly Ser Met Ala Thr Val Lys Phe Thr Tyr Gln Gly Glu
            165                 170                 175

Glu Lys Gln Val Asp Ile Ser Lys Ile Lys Ile Val Ala Arg Asp Gly
        180                 185                 190

Gln Tyr Ile Asp Phe Lys Tyr Asp Glu Gly Gly Ala Tyr Gly Tyr
    195                 200                 205

Gly Trp Val Ser Glu Lys Asp Ala Pro Lys Glu Leu Leu Gln Met Leu
210                 215                 220

Glu Lys Gln Gly Gly Gly Ser Gly Gly Gly Ser Met Ala Thr
225                 230                 235                 240

Val Lys Phe Thr Tyr Gln Gly Glu Glu Lys Gln Val Asp Ile Ser Lys
            245                 250                 255

Ile Lys Ile Val Ala Arg Asp Gly Gln Tyr Ile Asp Phe Lys Tyr Asp
        260                 265                 270

Glu Ser Gly Gly Ala Tyr Gly Tyr Gly Trp Val Ser Glu Lys Asp Ala
    275                 280                 285

Pro Lys Glu Leu Leu Gln Met Leu Glu Lys Gln
290                 295
```

<210> SEQ ID NO 24
<211> LENGTH: 35
<212> TYPE: DNA
<213> ORGANISM: Artificial Sequence

```
<220> FEATURE:
<223> OTHER INFORMATION: Synthetic Polynucleotide

<400> SEQUENCE: 24
aggcagtctc atatgtgtgc aaccgtgaaa ttcac                              35

<210> SEQ ID NO 25
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 25
attgacctcg agttatccac ccgagaccac tgggtctcac accttgcttt tccagcatct    60

<210> SEQ ID NO 26
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 26
atttaaggtc tccggtggtg gtggtagcgg tggtggcggt tcaatggcaa ccgtgaaatt    60

<210> SEQ ID NO 27
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 27
atttaaggtc tcacaccttg cttttccagc atctgcagc                          39

<210> SEQ ID NO 28
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 28
taatacgact cactataggg                                               20

<210> SEQ ID NO 29
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 29
gctagttatt gctcagcgg                                                19

<210> SEQ ID NO 30
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 30

Gly Gly Gly Gly Gly Gly
1               5
```

<210> SEQ ID NO 31
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 31

Gly Gly Gly Gly Gly Gly Gly Gly
1               5

<210> SEQ ID NO 32
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 32

Glu Ala Ala Ala Lys Glu Ala Ala Ala Lys Glu Ala Ala Ala Lys
1               5                   10                  15

<210> SEQ ID NO 33
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 33

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
            35                  40                  45

<210> SEQ ID NO 34
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 34

Pro Ala Pro Ala Pro
1               5

<210> SEQ ID NO 35
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 35

Val Ser Gln Thr Ser Lys Leu Thr Arg Ala Glu Thr Val Phe Pro Asp
1               5                   10                  15

Val

<210> SEQ ID NO 36
<211> LENGTH: 6
<212> TYPE: PRT
<213> ORGANISM: Artificial Sequence

```
<220> FEATURE:
<223> OTHER INFORMATION: Synthetic Polypeptide

<400> SEQUENCE: 36

Arg Val Leu Ala Glu Ala
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 37

Glu Asp Val Val Cys Cys Ser Met Ser Tyr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 38

Gly Gly Ile Glu Gly Arg Gly Ser
1               5

<210> SEQ ID NO 39
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 39

Gly Phe Leu Gly
1

<210> SEQ ID NO 40
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 40

Gly Gly Gly Gly Ser Gly Gly Gly Gly Ser
1               5                   10
```

OLIGOMERIZED PROTEIN-POLYMER CONJUGATES

RELATED APPLICATION

This application claims the benefit under 35 U.S.C. § 119(e) of U.S. provisional application No. 62/711,440, filed Jul. 27, 2018, the entire contents of which is incorporated by reference herein in its entirety.

GOVERNMENT SUPPORT

This invention was made with Government support under Grant No. FA9550-12-1-0259 awarded by the Air Force Office of Scientific Research. The Government has certain rights in the invention.

FIELD

Protein-polymer conjugates that detect targets of interest are disclosed herein.

BACKGROUND

The highly-specific molecular recognition capabilities of proteins have enabled their widespread use in a variety of biosensor formats including lateral flow assays,[1-4] microfluidics,[5-8] and microarrays.[9-10] In each of these biosensors, proteins are immobilized on a surface, where device sensitivity is enhanced by achieving densely-packed proteins that are well-oriented to allow free access to binding sites.[11-13] The simplest and most general methods for protein surface functionalization involve covalent anchoring via free amines on the surfaces of proteins. Because these amines are distributed at multiple points across the protein surface, however, the resulting orientation is random, reducing the active proportion of the surface-immobilized binding protein. As such, there is significant interest in developing techniques that enable site-specific immobilization. Current directed immobilization strategies include modifying functional groups that appear at only a single location on a protein,[14-15] adding ssDNA fragment linkers,[16] or fusing to proteins[17-18] and installing tags[19-20] that display high binding affinity to a specific surface. While all of these methods can be used to orient proteins and improve biosensor performance, these approaches can only be used for specific classes of proteins or require significant protein and/or surface pre-treatment.

One potentially straightforward and effective technique for creating a dense array of properly oriented proteins is through utilization of block copolymer-like self-assembly. By conjugating a protein to a polymer and dissolving the bioconjugate in concentrated aqueous solution, it has been demonstrated that these conjugates assemble into ordered nanostructures similar to coil-coil diblock copolymers.[21-23] While the individual ordered phases in both types of diblock copolymers are identical, the self-assembly of protein-polymer conjugates exhibits notable differences from that of traditional block copolymers. Protein-polymer conjugates display highly asymmetric phase behavior[24] and re-entrant order-disorder transition (ODT) behavior,[24-25] in contrast to the enhanced ordering in more concentrated block copolymer solutions predicted by the dilution approximation.[26] A complete explanation for these deviations from characteristic block copolymer assembly has not yet been established, but it is known that coarse-grained features of the conjugates have significant effects on self-assembly: polymer topology,[27] polymer chemistry,[25] protein shape,[28] and electrostatics[29] have all been found to significantly affect phase behavior and ordering in protein-polymer block copolymers.

SUMMARY

Initial studies have been performed on the activity and binding capabilities of enzymatic coatings and sensors developed from these conjugates. Thin films of myoglobin-b-poly(N-isopropylacrylamide) (PNIPAM) formed weakly-ordered lamellae in solution and exhibited up to a 10-fold improvement in catalytic activity compared to common surface-immobilization techniques.[30] Similar antibody-PNIPAM thin film biosensors displayed a two order of magnitude decrease in the limit of detection compared to an antibody monolayer and a linear relationship between the number of binding events and film thickness, which is related to the total amount of protein in the film.[31] These studies suggest that the increased number of proteins that can be immobilized on a surface in 3D arrays achieved through protein-polymer diblock copolymer self-assembly can greatly enhance protein catalytic and sensing capabilities.

While protein-polymer conjugates incorporating antibodies as the protein block have been shown to function as highly sensitive biosensors, there is a growing trend toward using small proteins as affinity elements in sensors due to their enhanced stability and the ease with which they can be recombinantly expressed. For example, Nanobodies®—the 12-15 kDa single binding domain of heavy chain-only antibodies—have been incorporated into biosensors to achieve improved sensitivities compared to antibody-based sensors due to the greater surface functionalization achievable with these smaller proteins.[32] This sensitivity improvement is more clearly seen in electrochemical sensors[33-34] where the decreased distance between binding events and the surface has resulted in increased signal strength. Small engineered affinity binding proteins have also received more frequent use as sensors within the past decade. A class of 6 kDa proteins consisting of a three-helix bundle, affibodies, have been demonstrated to function effectively in microarray formats.[35-36] Similarly, 7 kDa DNA-binding proteins, particularly Sac7d and Sso7d, have been designed to bind with antibody-level affinities to a variety of targets.[37-39] Though their use in biosensors has only recently been explored,[18, 39-40] these engineered DNA-binding protein mutants display exceptional stability over a wide pH and temperature range,[41] making them attractive candidates for sensors that remain functional in conditions under which proteins typically unfold.

There are numerous potential benefits to using small proteins in biosensors fabricated from protein-polymer conjugates, but the weak ordering in these conjugates containing a small protein block remains a barrier to maximizing device sensitivity by self-assembly. In traditional coil-coil block copolymers, ordered phases are only observed when the overall degree of polymerization of the diblock copolymer is large enough to sufficiently reduce the entropic penalty due to chain stretching that occurs at the interfaces between domains. While the self-assembly of protein-polymer block copolymers is not fully understood, similar trends have been observed in these materials. Model studies using the fluorescent protein mCherry as the protein block in these conjugates have found that no ordered structures are observed at low coil fractions ($0.2 \leq f \leq 0.3$),[24] and at intermediate coil fractions ($0.3 \leq f \leq 0.5$), structures are significantly weaker ordered than the corresponding phases at high coil fractions (0.5≤f≤0.75).[24-25] Thus, exploring approaches to increase the molecular weight of the protein block in protein-polymer conjugates may yield methods to create well-ordered structures of these conjugates incorporating a low molecular weight protein.

Herein, the effect of increasing molecular weight of low molecular weight protein blocks on ordering in protein-polymer conjugates is explored using protein blocks incorporating an Sso7d mutant engineered to bind strongly to streptavidin, rcSso7d.SA.[39] Oligomers of rcSso7d.SA are created by linking the proteins with short, flexible peptide sequences, and the phase behavior of conjugates of these oligomers—monomer to tetramer—with PNIPAM is studied. While conjugates of monomeric rcSso7d.SA are disordered under all conditions studied, conjugates of oligomeric rcSso7d.SA are observed to self-assemble into well-ordered lamellar structures. The biosensing capabilities of these conjugates are also explored, and it is discovered that the trimer conjugates provide over a 3-fold reduction in limit of detection compared to monolayers of rcSso7d. SA.

In some aspects, the present disclosure relates to a protein-polymer conjugate comprising an oligomer of an engineered binding protein linked to a polymer, wherein the protein-polymer conjugate self-assembles into a lamellar nanostructure. In some embodiments, the polymer comprises a poly(N-isopropylacrylamide) (PNIPAM) block, a poly(hydroxypropyl acrylate) (PHPA) block, a poly(oligoethylene glycol acrylate) (POEGA) block, or a poly(3-(2-methyacroyloyethyl)-N,N-dimethylammonio)propane sulfonate) (PDMAS) block.

In some embodiments of the present disclosure, the protein oligomers comprise trimers and/or tetramers of the binding protein. In some embodiments, the binding protein is a Sso7d protein, a Sac7d protein, an engineered coiled-coil protein, or an antibody variable domain. In some embodiments, the Sso7d protein is an rcSso7d protein engineered to bind a ligand. In some embodiments, the ligand is streptavidin. In some embodiments, the rcSso7d protein comprises at least 85% of the amino acid sequence of SEQ ID NO: 2 from *Sulfolobus solfataricus*.

In some embodiments of the present disclosure, the coiled-coil protein is a three-helix bundle protein. In some embodiments, the antibody variable domain is a single variable domain, such as a VH, VHH and/or VL domain. In some embodiments, the oligomer of the antibody variable domain is an scFv.

In some embodiments of the present disclosure, the binding proteins are linked by peptide linkers. In some embodiments, the peptide linkers comprise Gly-Ser linkers.

In some aspects, the present disclosure relates to a biosensor comprising the protein-polymer conjugate disclosed herein bound to a surface. In some embodiments, the protein-polymer conjugate forms a thin film on the surface, such as a lamellar nanostructure. In some embodiments, the thin film comprises at least 2-fold more binding sites in an area of the protein-polymer conjugate compared to a monolayer of the protein of the same size as the area of the protein-polymer conjugate. In some embodiments, the unit spacing between repeating domains of protein-polymer conjugates on the surface is less than 50 nm. In some embodiments, the unit spacing between repeating domains of protein-polymer conjugates on the surface is less than 30 nm.

In some embodiments of the present disclosure, the limit of detection for binding by the protein is between 5 nM and 300 nM. In some embodiments, the surface is a semiconductor material, a quartz material, a glass material, a paper material, a cellulose material, or a nitrocellulose material. In some embodiments, the surface is silicon.

In some aspects, the present disclosure provides methods for making a protein-polymer conjugate comprising conjugating a protein to a polymer and dissolving the protein-polymer conjugate in aqueous solution. In some embodiments of the methods, the polymer is in molar excess of the protein. In some embodiments of the methods, the conjugating is in the presence of a cross-linking agent. In some embodiments of the methods, the cross-linking agent is: an aldehyde, optionally glutaraldehyde or formaldehyde; or ultraviolet light and $Ru(BiPy)_3^{+2}$.

In some aspects, the present disclosure provides methods for detecting a ligand of interest, the methods comprising: contacting a biosensor as described above with a sample comprising a ligand of interest, wherein the engineered binding protein oligomer binds the ligand of interest; and detecting the ligand of interest bound by the engineered binding protein oligomer. In some embodiments, the unit spacing between repeating domains of engineered protein oligomers on the surface is less than 50 nm. In some embodiments, the unit spacing between repeating domains of engineered protein oligomers on the surface is less than 30 nm. In some embodiments, the molecular weight of the ligand of interest is less than 50 kDa. In some embodiments, the molecular weight of the ligand of interest is less than 25 kDa.

In some embodiments of the methods, the protein-polymer conjugate is in molar excess of the ligand of interest. In some embodiments, the protein-polymer conjugate is in 10-fold molar excess of the ligand of interest. In some embodiments, the ligand of interest is streptavidin or monomeric streptavidin.

In some embodiments of the methods, the sample is a biological sample from a subject. In some embodiments, the biological sample is blood, serum, or urine. In some embodiments, the subject is a mammal. In some embodiments, the subject is a human. In some embodiments, the subject has or is suspected of having an infectious disease.

In some aspects, the present disclosure provides methods for detecting a ligand of interest, the methods comprising: contacting the protein-polymer conjugate described above with a sample comprising a ligand of interest, wherein the ligand of interest binds to the engineered binding protein oligomer and forms a complex; contacting the complex with a surface for a time sufficient for the complex to bind the surface; and detecting the ligand of interest bound by the engineered binding protein oligomer. In some embodiments, the unit spacing between repeating domains of protein-polymer conjugates is less than 50 nm. In some embodiments, the unit spacing between repeating domains of protein-polymer conjugates is less than 30 nm. In some embodiments, the molecular weight of the ligand of interest is less than 50 kDa. In some embodiments, the molecular weight of the ligand of interest is less than 25 kDa.

In some embodiments of the methods, the protein-polymer conjugate is in solution. In some embodiments, the solution comprises a buffer. In some embodiments, the sample is a biological sample. In some embodiments, the protein-polymer conjugate is in molar excess of the ligand of interest. In some embodiments, the protein-polymer conjugate is in at least 10-fold molar excess of the ligand of interest. In some embodiments, the ligand of interest is streptavidin or monomeric streptavidin.

In some embodiments of the methods, the surface is a semiconductor material, a quartz material, a glass material, a paper material, a cellulose material, or a nitrocellulose material. In some embodiments, the surface is silicon.

In some embodiments of the methods, the sample is a biological sample from a subject. In some embodiments, the biological sample is blood, serum, or urine. In some embodiments, the subject is a mammal. In some embodiments, the subject is a human. In some embodiments, the subject has or is suspected of having an infectious disease.

In some embodiments of the methods, the engineered high-affinity binding protein oligomer binds to streptavidin or monomeric streptavidin. In some embodiments, the limit of detection for binding by the protein is between 5 nM and 300 nM.

In some aspects, the present disclosure provides kits for assessing a presence or amount of a ligand, the kits comprising a container containing the protein-polymer conjugate described above. In some embodiments, the kits further comprise a surface for binding the protein-polymer conjugate. In some embodiments, the protein-polymer conjugate is bound to the surface. In some embodiments, the protein-polymer conjugate is not bound to the surface. In some embodiments, the surface is a semiconductor material, a quartz material, a glass material, a paper material, a cellulose material, or a nitrocellulose material. In some embodiments, the surface is silicon.

In some aspects, the present disclosure provides methods of detecting a ligand of interest, the method comprising contacting a biosensor as described herein with a sample comprising a ligand of interest, wherein the ligand of interest binds to a protein-polymer conjugate and forms a complex, and detecting the ligand of interest bound by the protein-polymer conjugate.

In some embodiments, the sample is a biological sample. In some embodiments, the biological sample is blood, serum, or urine. In some embodiments, the biological sample is from a subject having or suspected of having an infectious disease. In some embodiments, the subject is a mammal. In some embodiments, the subject is a human.

In some embodiments, the protein-polymer conjugate is in molar excess of the ligand of interest. In some embodiments, the protein-polymer conjugate is in at least 10-fold molar excess of the ligand of interest. In some embodiments, the ligand of interest is streptavidin or monomeric streptavidin.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

(FIG. 1A) Representation of rcSso7d.SA oligomers. From top to bottom: 1×rcSso7d.SA, 2×rcSso7d.SA, 3×rcSso7d.SA, 4×rcSso7d.SA. (FIG. 1B) General schematic of N-Cys-rcSso7d.SA oligomer conjugation to maleimide end-functionalized PNIPAM. Protein is a cartoon representation of the Sso7d crystal structure (PDB 1550).[42]

FIGS. 3A-3B. SAXS curve displaying changes in conjugate phase behavior with (FIG. 3A) temperature and (FIG. 3B) concentration. Both graphs contain data for 4×SP30k at either (FIG. 3A) 40 wt. % or (FIG. 3B) 25° C. and are representative of trends observed across all studied conjugates.

(FIG. 5A) Domain spacings in lamellar phases, (FIG. 5B) high concentration SAXS traces, and (FIG. 5C) average power fraction across heating and cooling cycles for 2×SP17k, 3×SP25k, and 4×SP30. Data in (FIG. 5A) and (FIG. 5B) are collected at 25° C., and bulk data are disconnected from concentrated solution data to indicate that the 100 wt. % data are not at equilibrium. In (FIG. 5B) the low intensity of the 2q* peak in the 2×SP17k scattering pattern is likely a result of a coincidence with a minimum in the form factor. Error bars in (FIG. 5C) represent standard deviation of the data set.

(FIG. 6A) Schematic representation of fluorescent binding assays performed within rcSso7d.SA oligomer-PNIPAM conjugate thin films. (FIG. 6B) Comparison of binding curves obtained for each considered conjugate and rcSso7d.SA monolayer. All curves are shifted to a background signal of 0 for clarity. Thicknesses for the 1×SP9.8k, 2×SP17k, 3×SP25k, and 4×SP30k films are 155, 130, 150, and 170 nm, respectively. Error bars represent the standard deviation of three replicates. (FIG. 6C) Predicted and calculated relative number of binding sites in each conjugate thin film. All values are relative to the number of binding sites in the 1×SP9.8k thin film. Error bars represent 95% confidence intervals for the calculated relative number of binding sites.

(FIG. 7A) Schematic representation of the Golden Gate assembly of the rcSso7d oligomers. Construct #1, bearing a codon encoding an N-terminal cysteine and opposing BsaI sites, was stably incorporated into an acceptor plasmid. Construct #2, featuring an N-terminal GS linker, was incorporated into this acceptor plasmid in a stochastic manner to yield the library of ligation products. (FIG. 7B) Representative colony PCR gel with selected clones from the resulting library. Labels at left represent the DNA product size, and labels at right represent the degree of oligomerization yielding bands at this product size.

(FIG. 20A) SAXS curves for samples incubated at room temperature for 0, 1, 2, 4, or 7 days (bottom to top). (FIG. 20B) FWHM$^{-1}$ of the primary scattering peak for samples in (FIG. 20A) indicate a slight improvement in ordering with increasing incubation time. (FIG. 20C) CD spectra of the conjugates reveal that the protein block remains folded during incubation at room temperature.

FIGS. 27A-27F. Binding curves for conjugate thin films exposed to SA (FIGS. 27A, 27B) or mSA2 (FIGS. 27C, 27D) in 50% urine (FIGS. 27A, 27C) or 50% blood serum (FIGS. 27B, 27D) solutions for 4 hours. Results are compared to those obtained using a rcSso7d.SA monolayer with a 4 hour exposure time. The limit of detection determined for each binding curve is reported for urine samples (FIG. 27E) and blood samples (FIG. 27F). Film thicknesses are listed in Table 8. Error bars represent the standard deviation of three replicates.

DETAILED DESCRIPTION

Figure 1A:
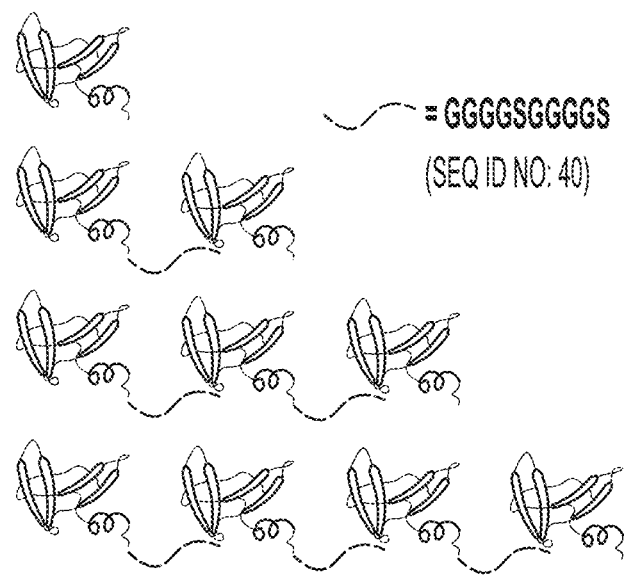
FIGS. 1A-1B.

The self-assembly of protein-polymer conjugates incorporating oligomers of a small, engineered high-affinity binding protein, rcSso7d.SA, is studied to determine the effect of protein oligomerization on nanoscale ordering. Oligomerization enables a systematic increase in the protein molar mass without changing its overall folded structure, leading to a higher driving force for self-assembly into well-ordered structures. Though conjugates of monomeric rcSso7d.SA are found to only exist in disordered states, oligomers of this protein linked to a poly(N-isopropylacrylamide) (PNIPAM) block self-assemble into lamellar nanostructures. Conjugates of trimeric and tetrameric rcSso7d.SA are observed to produce the strongest ordering in concentrated solution, displaying birefringent lamellae at concentrations as low as 40 wt. % that order with significantly higher quality than previously-studied protein-polymer conjugates. In highly concentrated solution, the oligomeric rcSso7d.SA-PNIPAM block copolymers exhibit ordering and domain spacing trends atypical from that of most block copolymers. Fluorescent binding assays indicate that oligomerized protein blocks retain binding functionality and exhibit limits of detection up to three times lower than that of surface-immobilized protein sensors. Therefore, oligomerization of the protein block in these block copolymers serves as an effective method to improve both nanoscale ordering and biosensing capabilities.

Protein-Polymer Conjugates

Engineered Binding Proteins

In some aspects, provided herein are protein-polymer conjugates that comprise an engineered binding protein, such as a ligand-binding protein or ligand-binding domain. In some embodiments, the ligand-binding protein is an engineered Sso7d ligand-binding protein. The Sso7d protein from the hyperthermophilic archaeon *Sulfolobus solfataricus* is a small protein (7 kDa) with high thermal stability ($T_m$ of 98° C.), which is highly positively charged since it is a DNA-binding protein. The high positive charges in Sso7d introduce a strong specificity constraint for binding epitopes and leads to nonspecific interaction with mammalian cell membranes. Charge-neutralized variants of Sso7d that maintain high thermal stability have been reported[43].

In some embodiments, the Sso7d ligand-binding protein comprises the amino acid sequence of SEQ ID NO: 1, corresponding to the amino acid sequence of Sso7d from *Sulfolobus solfataricus* (UniProtKb: P39476; European Nucleotide Archive: AAK42212.1)

Amino acid sequence of Sso7d from *Sulfolobus solfataricus* (SEQ ID NO: 1):

(SEQ ID NO: 1)
MATVKFKYKGEEKEVDISKIKKVWRVGKMISFTYDEGGGKTGRGAVSEK
DAPKELLQMLEKQKK

Orthologs of Sso7d have been described in various species, including *Sulfolobus islandicus* (NCBI Reference Sequence: WP 012713334.1), *Sulfolobus tokodaii* (NCBI Reference Sequence: WP 010978621.1), *Sulfolobus* sp. A20 (Sequence ID: WP 069284107.1), *Acidianus hospitalis* (NCBI Reference Sequence: WP 013777046.1), and *Acidianus manzaensis* (GenBank: ARM76167.1).

In some embodiments, the Sso7d ligand-binding protein is a reduced-charge variant of Sso7d (rcSso7d). In some embodiments, the rcSso7d ligand-binding protein comprises the amino acid sequence of SEQ ID NO: 2.

Amino acid sequence of rcSso7d from *Sulfolobus solfataricus* (SEQ ID NO: 2):

(SEQ ID NO: 2)
MATVKFTYQGEEKQVDISKIKKVWRVGQMISFTYDEGGGATGRGAVSEK
DAPKELLQMLEKQ

In some embodiments, the engineered ligand-binding protein is Sso7a. In some embodiments, the Sso7a ligand-binding protein is from *Sulfolobus solfataricus* (UniProtKB: P61991; European Nucleotide Archive: AAK42090.1).

Amino acid sequence of Sso7a from *Sulfolobus solfataricus* (SEQ ID NO: 3):

(SEQ ID NO: 3)
MATVKFKYKG EEKQVDISKI KKVWRVGKMI SFTYDEGGGK
TGRGAVSEKD APKELLQMLE KQKK

In some embodiments, a reduced charge variant of Sso7a is contemplated herein.

In some embodiments, the ligand-binding protein is Sac7d from *Sulfolobus acidocaldarius* (UniProtKB: P13123). In some embodiments, the ligand-binding protein is a reduced-charge variant of Sac7d (rcSac7d).

Amino acid sequence of Sac7d from *Sulfolobus acidocaldarius* (SEQ ID NO: 4):

(SEQ ID NO: 4)
MVKVKFKYKG EEKEVDTSKI KKVWRVGKMV SFTYDDNGKT
GRGAVSEKDA PKELLDMLAR AEREKK

In some embodiments, the Sso7 ligand-binding protein is a variant that is at least or about 50% identical, at least or about 60% identical, at least or about 70% identical, at least or about 80% identical, at least or about 85% identical, at least or about 90% identical, at least or about 95% identical, at least or about 96% identical, at least or about 97% identical, at least or about 98% identical, at least or about 99% identical, at least or about 99.5% identical, at least or about 99.9% identical, or about 100% identical to the amino acid sequence of SEQ ID NO: 1, SEQ ID NO: 2, SEQ ID NO: 3, or SEQ ID NO: 4.

In some embodiments, the Sso7 ligand-binding protein includes variants which are shorter or longer than amino acid sequence of SEQ ID NO: 1, SEQ ID NO: 2, SEQ ID NO: 3, or SEQ ID NO: 4 by about 5 amino acids, by about 10 amino acids, by about 15 amino acids, by about 20 amino acids, by about 25 amino acids, by about 30 amino acids, by about 40 amino acids, by about 50 amino acids, or more.

Any orthologs of the sequences described herein may be identified conducting a BLAST search of the sequence of interest.

In some embodiments, the engineered binding protein of the protein-polymer conjugates provided herein are engineered coiled-coil proteins such as Affibodies® or Alphabodies®. Affibodies are 6 kDa proteins consisting of 58 amino acids folded into a three-helix bundle that are engineered to bind to a large number of targets or ligands with high affinity. Affibodies can withstand high temperatures (up to 90° C.) and extreme pH conditions (down to pH 2.5 or up to pH 11).[44-46] Alphabodies are 10 kDa engineered proteins designed to bind intracellular protein targets. Alphabodies were developed as scaffolds comprising amino acid residues which maintain correct folding and thermostability, but are modified to bind targets.[47] Additional non-limiting examples of coiled-coil proteins which contain three-helix bundles are DNA binding proteins such as Oct1 and Oct2 from humans, phosphotransferase proteins such as enzyme IIA$^{lactose}$ from *L. lactis* bacteria, and immunoglobulin-binding proteins such as Protein A (domains B, E, and Z) from *S. aureus*, Protein G from *Streptococcus*, and Protein L from *Peptostreptococcus*.

In some embodiments, the engineered binding protein of the protein-polymer conjugates provided herein is an antibody variable domain. Antibody variable domains are well-known in the art (see, e.g., ref. 48) and provide the antigen-binding specificity for a given antibody. Human immunoglobulin antibodies are large (~150 kDa) proteins which are typically composed of two heavy chains and two light chains. All human immunoglobulin heavy and light chains contain a variable domain (VH and VL, respectively) that are important for antigen binding. The smallest antigen binding fragment of an immunoglobulin which maintains the complete antigen binding site is the Fv (variable fragment), which consists of the VH and VL domains[49]. The VH and VL domains can be expressed as fusions independently of the constant fragment ($F_c$) of immunoglobulin molecule to confer antigen-binding to a protein, peptide, etc. In some embodiments, VH and VL domains are expressed as single-chain antibody fragments (scF$_{abs}$), diabodies, triabodies, or tetrabodies[50,51]. In some embodiments, VH and VL domains are expressed as bispecific antibodies which comprise two distinct antigen binding domains in one molecule[52-54]. In some embodiments, the antibody variable domain provided herein is a VHH single domain antibody[55]. These small (15 kDa) polypeptides correspond to the heavy chain variable region from camelid immunoglobulin molecules and are typically easily expressed in bacteria such as *E. coli* or yeast such as *Pichia pastoris* (also known as *Komagataella phaffii* or *Komagataella pastoris*). Vi single domain antibodies are commonly utilized for binding assays because stable in extreme temperatures (up to 90° C.) and stringent chemical conditions (up to 80% methanol)[56]. In some embodiments, the target binding domain of the protein-polymer conjugates provided herein is not a four-chain antibody molecule.

In some embodiments, the engineered binding protein of the protein-polymer conjugate binds to its target ligand with high affinity. High affinity binding between a protein and a ligand, as will be appreciated by a person skilled in the art, will depend on numerous factors, including: the protein, the ligand, the buffer solution in which the binding is taking place, the temperature, the presence or absence of other molecules in the binding solution, etc. In some embodiments, high affinity binding (as measured by dissociation constant or $K_d$) is between $10^{-14}$ mol/L and $10^{-5}$ mol/L, inclusive. In some embodiments a high affinity of binding is about $10^{-14}$ mol/L. In some embodiments a high affinity of binding is about $10^{-13}$ mol/L. In some embodiments a high affinity of binding is about $10^{-12}$ mol/L. In some embodiments a high affinity of binding is about $10^{-11}$ mol/L. In some embodiments a high affinity of binding is $10^{-10}$ mol/L. In some embodiments a high affinity of binding is about $10^{-9}$ mol/L. In some embodiments, a high affinity of binding is $10^{-8}$ mol/L. In some embodiments a high affinity of binding is about $10^{-7}$ mol/L. In some embodiments, a high affinity of binding is $10^{-6}$ mol/L. In some embodiments a high affinity of binding is about $10^{-5}$ mol/L.

In some embodiments, the engineered binding protein of the protein-polymer conjugate comprises oligomers of the target-binding protein. An oligomer, as used herein, is composed of multiple (two or more) polypeptides, which may or may not be joined by peptide linkers. For example, the oligomers can be dimers of two polypeptides, trimers of three polypeptides, or tetramers of four polypeptides. The two or more polypeptides in the oligomers can be the same (homo-oligomers) or different (hetero-oligomers) and in any order. For dimers, for example, the polypeptides can be the same (e.g., A-A), or different (e.g., A-B or B-A). For trimers, for example, the polypeptides can be all the same (e.g., A-A-A, B-B-B, C-C-C), all different (e.g., A-B-C, B-A-C, C-A-B, and so on), or have two of one type and one of another type (e.g., A-A-B, A-A-C, A-B-B, A-C-C, B-C-C, C-C-A, B-A-B, B—C—B, A-C-A, and so on).

The target-binding domain can be of essentially any size, such as 5 kDa, 6 kDa, 7 kDa, 8 kDa, 9 kDa, 10 kDa, 11 kDa, 12 kDa, 13 kDa, 14 kDa, 15 kDa, 16 kDa, 17 kDa, 18 kDa, 19 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, 100 kDa, or higher.

In some embodiments, the oligomer is composed of two Sso7d polypeptides. In some embodiments, the oligomer is composed of three Sso7d polypeptides. In some embodiments, the oligomer is composed of four Sso7d polypeptides. In some embodiments, the oligomer is composed of five Sso7d polypeptides. In some embodiments, the oligomer is composed of six Sso7d polypeptides. In some embodiments, the oligomer is composed of seven Sso7d polypeptides. In some embodiments, the oligomer is composed of eight Sso7d polypeptides. In some embodiments, the oligomer is composed of nine Sso7d polypeptides. In some embodiments, the oligomer is composed of ten Sso7d polypeptides.

In some embodiments, the engineered binding protein of the protein-polymer conjugate comprises an oligomer of an antibody variable domain. A common example of antibody variable domain oligomer is a single chain variable fragment (scFv). A scFv is composed of VH and VL domains derived from human immunoglobulin joined by a flexible linker. ScFvs are small (~25 kDa) polypeptides which contain an antigen-binding site. They are easily expressed in either *S. cerevisiae* or *E. coli* or other suitable yeast or bacteria. In some embodiments, the oligomer is composed of two scFv polypeptides. In some embodiments, the oligomer is composed of three scFv polypeptides. In some embodiments, the oligomer is composed of four scFv polypeptides. In some embodiments, the oligomer is composed of five scFv polypeptides. In some embodiments, the oligomer is composed of six scFv polypeptides. In some embodiments, the oligomer is composed of seven scFv polypeptides. In some embodiments, the oligomer is composed of eight scFv polypeptides. In some embodiments, the oligomer is composed of nine scFv polypeptides. In some embodiments, the oligomer is composed of ten scFv polypeptides In some embodiments, polypeptides which make up an oligomer are directly linked to each other. In some embodiments, the polypeptides of an oligomer, such as a Sso7d polypeptide or an antibody variable domain, are directly attached to upstream or downstream polypeptides through a peptide bond between the C-terminus of the upstream polypeptide and the N-terminus of the downstream polypeptide, i.e., are fusion proteins.

In some embodiments, the polypeptides which make up an oligomer are indirectly linked. In some embodiments, the polypeptides of an oligomer, such as a Sso7d polypeptide or an antibody variable domain, are linked through a linker. Non-limiting examples of linkers contemplated herein include a protein linker; a peptide linker, such as a Gly-Ser linker. Such linkers can have the formula $Gly_x$-$Ser_y$ in which x=1-XX and y=1-YY. The Gly-Ser linker can be replicated n number of times $[(Gly_x\text{-}Ser_y)_n]$, for example, wherein n=1, 2, 3, 4, 5, 6, 7, 8, 9, 10, 15, 20, 25, or 30, (e.g., a $(G_4S)_3$ inker has the amino acid sequence GGGGSGGGGSGGGGS, (SEQ ID NO: 5)). Additional non-limiting examples of linkers known to one of ordinary skill in the art, such as chemical linkers (e.g., crosslinkers, bifunctional linkers, trifunctional trilinkers), such as Bis[2-(N-succinimidyl-oxycarbonyloxy)ethyl] sulfone, 0,0'-Bis[2-(N-Succinimidyl-succinylamino)ethyl]polyethylene glycol 2,000, 0,0'-Bis[2-(N-Succinimidyl-succinylamino)ethyl]polyethylene glycol 3,000, 0,0'-Bis[2-(N-Succinimidyl-succinylamino)ethyl] polyethylene glycol 10,000, BS(PEG)5 (PEGylated bis (sulfosuccinimidyl)suberate), 4,4'-Diisothiocyanatostilbene-2,2'-disulfonic acid disodium salt hydrate, bromoacetic acid N-hydroxysuccinimide ester, maleimide-PEG2-succinimidyl ester, SBAP (succinimidyl 3-(bromoacetamido)propionate), 5-Azido-2-nitrobenzoic acid N-hydroxysuccinimide ester, etc.; flexible linkers (e.g., $(Gly)_6$ (SEQ ID NO: 30), $(Gly)_8$ (SEQ ID NO: 31), etc.), rigid linkers (e.g., $(EAAAK)_3$ (SEQ ID NO: 32), $A(EAAAK)_4ALEA$ $(EAAAK)_4A$ (SEQ ID NO: 33), PAPAP (SEQ ID NO: 34), etc.) and cleavable linkers (e.g., disulfide, VSQTSKLTR↓A-ETVFPDV (SEQ ID NO: 35), RVL↓AEA (SEQ ID NO: 36); EDVVCC↓SMSY (SEQ ID NO: 37); GGIEGR↓GS (SEQ ID NO: 38); GFLG↓ (SEQ ID NO: 39), etc.) naturally-occurring or synthetic, such as those disclosed in ref 57, are also contemplated herein. The fusion proteins (directly linked) or the or indirectly linked proteins can be encoded in a recombinant expression vector for expression by inserting nucleotide sequences encoding the proteins into the expression vector, with appropriate nucleotide sequences encoding linker sequences, if any, interspersed between the proteins. Expression vectors are described elsewhere herein.

In some embodiments, protein-polymer conjugates (e.g., engineered binding oligomers) are organized into repeating domains. A repeating domain, as used herein, refers to a three-dimensional arrangement of protein-polymer conjugates in which there are adjacent and alternating regions of protein and polymer. Repeating domains of protein-polymer conjugates are organized into units. These units may be on a surface (e.g., a biosensor) or in a solution (e.g., a biological sample). Repeating domains may contain only one type of protein-polymer conjugate, or repeating domains may contain multiple types of protein-polymer conjugates.

In some embodiments, units are arranged in a monolayer. In some embodiments, units are arranged in a three-dimensional film. The film may be on a surface (e.g., a biosensor) or in a solution (e.g., a biological sample). In some embodiments, the film is an ultra-thin film. As used herein, an ultra-thin film is a film whose thickness is less than about 50 nm. In some embodiments, the film is a thin film. As used herein, a thin film is a film whose thickness is between about 50 nm and 1000 nm. In some embodiments, the film is a thick film. As used herein, a thick film is a film whose thickness is greater than 1000 nm.

The spacing between the central portion of repeating domains ("unit spacing") in a film or monolayer affects the size of molecules that can diffuse through the film or monolayer. Unit spacing, as used herein, refers to the distance between the centers of repeating domains of a protein or polymer (e.g., on a surface or in a solution). In some embodiments, the unit spacing in a thin film or monolayer allows large (e.g., greater than 50 kDa) and small (e.g., less than 50 kDa) ligands to diffuse through the thin film or monolayer. In some embodiments, the unit spacing in a thin film or monolayer only allows small (e.g., less than 50 kDa) ligands to diffuse through the thin film or monolayer.

In some embodiments, the unit spacing in a thin film or monolayer is 1 nm-500 nm. In some embodiments, the unit spacing in a thin film or monolayer is 10 nm-250 nm. In some embodiments, the unit spacing in a thin film or monolayer is less than 100 nm. In some embodiments, the unit spacing in a thin film or monolayer is less than 90 nm. In some embodiments, the unit spacing in a thin film or monolayer is less than 80 nm. In some embodiments, the unit spacing in a thin film or monolayer is less than 70 nm. In some embodiments, the unit spacing in a thin film or monolayer is less than 60 nm. In some embodiments, the unit spacing in a thin film or monolayer is less than 50 nm. In some embodiments, the unit spacing in a thin film or monolayer is less than 40 nm. In some embodiments, the unit spacing in a thin film or monolayer is less than 30 nm. In some embodiments, the unit spacing in a thin film or monolayer is less than 20 nm. In some embodiments, the unit spacing in a thin film or monolayer is less than 10 nm. In some embodiments, the unit spacing in a thin film or monolayer is at least 1 nm, at least 2 nm, at least 3 nm, at least 4 nm, at least 5 nm, at least 6 nm, at least 7 nm, at least 8 nm, at least 9 nm, or at least 10 nm.

In some embodiments, the unit spacing in a thin film or monolayer limits the size of ligands that can diffuse through the thin film or monolayer. Small ligands (e.g., less than 50 kDa) may diffuse in a thin film monolayer with large or small unit spacing, while large ligands (e.g., greater than 50 kDa) may have limited diffusion in a thin film or monolayer with small unit spacing.

In some embodiments, the molecular weight of the ligand of interest is 1 kDa-500 kDa. In some embodiments, the molecular weight of the ligand of interest is 10 kDa-250 kDa. In some embodiments, the molecular weight of the ligand of interest is less than 100 kDa. In some embodiments, the molecular weight of the ligand of interest is less than 90 kDa. In some embodiments, the molecular weight of the ligand of interest is less than 80 kDa. In some embodiments, the molecular weight of the ligand of interest is less than 70 kDa. In some embodiments, the molecular weight of the ligand of interest is less than 60 kDa. In some embodiments, the molecular weight of the ligand of interest is less than 50 kDa. In some embodiments, the molecular weight of the ligand of interest is less than 40 kDa. In some embodiments, the molecular weight of the ligand of interest is less than 30 kDa. In some embodiments, the molecular weight of the ligand of interest is less than 20 kDa. In some embodiments, the molecular weight of the ligand of interest is less than 10 kDa. In some embodiments, the molecular weight of the ligand of interest is at least 1 kDa, at least 2 kDa, at least 3 kDa, at least 4 kDa, at least 5 kDa, at least 6 kDa, at least 7 kDa, at least 8 kDa, at least 9 kDa, or at least 10 kDa.

Polymer Block

According to some aspects, the protein-polymer conjugates provided herein comprise an engineered binding protein conjugated to a polymer block (polymer). As used herein, polymer block or polymer refer to two or more monomers clustered together to form repeating patterns. In some embodiments, the polymer comprises a poly(N-isoproprylacrylamide) (PNIPAM) block. PNIPAM is a stimulus-responsive polymer consisting of amide (CONH) and propyl (CH(CH$_3$)$_2$) moieties. PNIPAM is temperature-responsive, and, when heated above 32° C., it undergoes a phase transition from a swollen hydrated state to a shrunken, dehydrated state as it loses about 90% of its volume. Since PNIPAM expels its liquid contents at a temperature near that of the human body, it is has been extensively investigated for possible applications in biosensing, tissue engineering, and drug delivery.

Polymers of PNIPAM monomers pack into predictable two-dimensional or three-dimensional forms based upon the method of polymer synthesis. For example, PNIPAM polymers are synthesized to enhance end-conjugation of moieties, to include water, thus forming PNIPAM microgels, and to ensure responsiveness to stimuli such as temperature and/or pH. Thus, conjugating a molecule such as small protein to a PNIPAM polymer will enhance the functional immobilization of the protein along a surface. This is particularly advantageous in the manufacture of biosensors, wherein a surface which is densely populated by functionally immobilized protein yields significant technical advantages.

In some embodiments, the polymer is generated with a functionalized end to facilitate conjugation to a protein. A functionalized polymer contains a desired group at a specified position on the polymer. Functionalized polymers are generated either as part of the polymer synthesis reaction or as a separate step after the polymer is generated. In some embodiments, the polymer block is PNIPAM functionalized with a maleimide group (PNIPAM-MA) to facilitate conjugating the PNIPAM block to a protein. Maleimide is an electrophilic compound with high reactivity towards thiol groups, which are present in cysteine residues of proteins and peptides. The maleimide group reacts with a thiol group in cysteine at pH 6.5-7.5, forming a thioether linkage that is not reversible.

In some embodiments, the polymer block is any water-soluble polymer that can be conjugated to protein. In some embodiments, the polymer block is a poly(hydroxypropyl acrylate) (PHPA) polymer. In some embodiments, the polymer block is a poly(oligoethylene glycol acrylate) (POEGA) polymer. In some embodiments, the polymer block is a poly(3-[N-(2-methacroyloyethyl-N,N-dimethylammonio] propane sulfonate (PDMAPS) polymer.

Ligands

As described herein, a ligand or ligand of interest refers to any molecule that can bind to the engineered binding protein, such as the engineered rcSso7d ligand-binding protein described herein. In some embodiments, the ligand binds to the engineered binding protein immobilized on the surface of a biosensor. In some embodiments, a ligand is in an aqueous environment. In some embodiments, the ligand is in a biological fluid or tissue. In other embodiments, the ligand is a marker of disease. In some embodiments, a ligand is an exogenous ligand, an endogenous ligand, or a neo-ligand (e.g., viral ligand, a tumor ligand, etc.). In some embodiments, the ligand or ligand of interest is a streptavidin molecule. Streptavidin is a 53 kDa protein purified from bacteria which forms homotetramers. In some embodiments, the ligand or ligand of interest is a monomeric streptavidin molecule. Monomeric streptavidin is a 15.6 kDa protein purified from bacteria. The affinity of streptavidin for biotin is one of the strongest non-covalent interactions known. Streptavidin is extensively utilized in molecular biology and biotechnology due to the resistance of the streptavidin-biotin complex to organic solvents, denaturants, detergents, proteolytic enzymes, and extremes of both temperature and pH.

In some embodiments, the engineered rcSso7d ligand-binding protein includes a motif which recognizes and/or binds to a specific ligand of interest. In some embodiments, the engineered rcSso7d ligand-binding protein which recognizes and/or binds to the ligand of interest comprises an amino acid sequence that recognizes and/or binds to streptavidin (e.g., rcSso7d.SA), such as the amino acid sequence

```
                                              (SEQ ID NO: 6)
MATVKFTYQGEEKQVDISKIKIVARDGQYIDEKYDEGGGAYGYGWVSEKD
APKELLQMLEKQ.
```

Additional non-limiting examples of engineered rcSso7d ligand-binding protein variants that bind to streptavidin are listed in Table A.

sine amino acid residues, modification of tryptophan amino acid residues, or modifications at the N- or C-terminus of a protein. Additionally, some bioconjugation strategies employ a unique functional group, such as a ketone or aldehyde, incorporated into a protein, such as a ketone or aldehyde, which is then conjugated to a biomolecule.

A common bioconjugation strategy is to utilize a maleimide group to conjugate to the thiol group of a cysteine amino acid residue in a protein or peptide. Maleimides are highly electrophilic compounds which specifically conjugate to thiol groups when the pH is between 6.5 and 7.5, or to primary amino groups at a pH greater than 8.5. Maleimides can be joined to small molecules such as fluorescent dyes, polymers, oligonucleotides, or proteins. The maleimide group can be added to the polymer, such as in the maleimide end-functionalized PNIPAM polymer exemplified herein.

In some aspects of the present disclosure, the engineered binding protein is conjugated to a maleimide group on a PNIPAM polymer. This conjugation reaction occurs spontaneously in the presence of a reagent which reduces the thiol group of a cysteine. For proteins that do not contain a cysteine residue, one or more cysteine residues can be added to the protein (preferably at the N-terminus or C-terminus) or oligomer thereof by expressing a nucleic acid molecule that encodes the protein, which nucleic acid molecule is modified to also include one or more cysteines. See, for example, the engineered N-Cys-rcSso7d. SA protein exemplified herein (see, e.g., FIG. 1).

In some embodiments, there is a molar excess of polymer to engineered binding protein in the bioconjugation reaction, such as a 1.5-fold molar excess, 2-fold molar excess, 3-fold molar excess, 4-fold molar excess, 5-fold molar excess, 6-fold molar excess, 7-fold molar excess, 8-fold molar excess, 9-fold molar excess, 10-fold molar excess, 11-fold molar excess, 12-fold molar excess, 13-fold molar excess, 14-fold molar excess or 15-fold molar excess. In some embodiments, there is a 2-fold molar excess of polymer to engineered binding protein. In some embodiments, there is a 5-fold molar excess of polymer to engineered binding

TABLE A

Engineered rcSso7d ligand-binding protein variants that bind to streptavidin

| rcSso7d Variant | SEQ ID NO | Amino Acid Sequence (N-terminus to C-terminus) |
|---|---|---|
| SA-AF647 | 7 | MATVKFTYQGEEKQVDISKIKYVYRWGHYIYFWYDEGGGASGWGWVSEKDAPKELLQ |
|  | 8 | MATVKFTYQGEEKQVDISKIKHVRRWGQWIYFIYDEGGGARGNGYVSEKDAPKELLQ |
|  | 9 | MATVKFTYQGEEKQVDISKIKRVRRYGQWIAFHYDEGGGAAGWGYVSEKDAPKELLQ |
|  | 10 | MATVKFTYQGEEKQVDISKIKWVWRGGQGIIFWYDEGGGARGYGRVSEKDAPKELLQ |
|  | 11 | MATVKFTYQGEEKQVDISKIKRVIRIGQYIYFWYDEGGGARGWGYVSEKDAPKELLQ |
|  | 12 | MATVKFTYQGEEKQVDISKIKWVHRWGQRIRFWYDEGGGAAGNGKVSEKDAPKELLQ |
|  | 13 | MATVKFTYQGEEKQVDISKIKWVIRWGQWIWFKYDEGGGASGWGYVSEKDAPKELLQ |
|  | 14 | MATVKFTYQGEEKQVDISKIKRVRRWGQWIYFRYDEGGGAYGSGYVSEKDAPKELLQ |
|  | 15 | MATVKFTYQGEEKQVDISKIKYVYRWGQWIYFWYDEGGGAWGRGYVSEKDAPKELLQ |

Additional non-limiting examples of ligands of interest include antibodies, peptides, etc. In some embodiments, the ligand of interest is PSA, troponin, tau protein, IP-10, Schistosome GST, CA-125, or ospA.

Bioconjugation

Also disclosed herein are methods of conjugating a protein to a polymer, a process also known as bioconjugation. Bioconjugation, as used herein, refers to the chemical joining through a covalent link of one molecule (e.g., protein) to another (e.g., polymer). Various bioconjugation strategies are utilized, including coupling to lysine, cysteine, or tyroprotein. In some embodiments, there is a 10-fold molar excess of polymer to engineered binding protein.

Biosensors

Also disclosed herein are biosensors which detect binding of the ligand to the protein-polymer conjugate. A biosensor is an analytical device which is used for the detection of a ligand, which combines a biological component along with a chemical detector. Biosensors typically consist of three components: the component (e.g., the protein) that binds the analyte (e.g., the ligand) and produces a signal upon binding; a detector which is typically an electrical interface; and a reader device, which displays the results of analyte binding. Common applications of biosensors are in lateral flow assays, microfluidics, and microarrays.

The material that comprises the surface of a biosensor can be selected depending upon the application for which the biosensor will be utilized. The material that comprises that surface must allow not only the immobilization of a protein, but also the detection of ligand binding. For example, when ligand binding detection involves fluorescence, common biosensor surfaces are quartz and semiconductor materials (e.g., silicon). Other examples of commonly utilized biosensor surfaces include glass, paper, cellulose, or nitrocellulose. In some embodiments, the protein-polymer conjugate of the current disclosure is immobilized on a surface that is a semi-conductor material. In some embodiments, the surface is silicon.

Biosensors utilized in each of the above applications comprise proteins immobilized on a surface. The sensitivity of biosensors is enhanced when the proteins are densely packed along the surface in orientations which allow free access of the ligands to the protein binding sites. An additional strategy for the immobilization of a protein on a surface is to conjugate the protein to a polymer which will drive the packing of the protein-polymer conjugate into a nanostructure.

A nanostructure, as used herein, refers to the three-dimensional conformation adopted by the protein-polymer conjugate on a surface. Nanostructures in which the protein-polymer conjugate adopts an ordered conformation comprise increased ligand binding sites compared to nanostructures in which the protein-polymer conjugate adopts a disordered conformation. Ordered conformation, as used herein, refers to a regularly spaced organization of protein-polymer conjugates. Disordered conformation, as used herein, refers to a non-regularly spaced organization of protein-polymer conjugates. In some embodiments, engineered binding protein oligomers in the protein-polymer conjugate adopt an ordered conformation. In some embodiments, engineered binding protein monomers in the protein-polymer conjugate adopt a disordered conformation. In some embodiments, protein-polymer conjugates with engineered binding protein oligomers have more ligand binding sites than protein-polymer conjugates with engineered binding protein monomers. A monolayer nanostructure is formed by the deposition of a single layer of proteins on a surface. In some embodiments, engineered binding protein monomers form monolayer nanostructures. A lamellar nanostructure is a highly ordered conformation in which the layers which comprise the three-dimensional structure are organized in sheets. In some embodiments, engineered binding protein oligomers form lamellar nanostructures. In some embodiments, engineered binding protein monomers form monolayer nanostructures. In some embodiments, there are more protein binding sites on a surface comprising protein-polymer conjugate in a lamellar nanostructure compared to the number of protein binding sites on a surface comprising protein in a monolayer nanostructure. In some embodiments, there are at least 2-fold, at least 5-fold, at least 10-fold, at least 20-fold, at least 30-fold, at least 40-fold, at least 50-fold, at least 60-fold, at least 70-fold, at least 80-fold, at least 90-fold, or 100-fold more binding sites on a surface comprising protein-polymer conjugate in a lamellar nanostructure compared to the number of protein binding sites on a surface comprising protein in a monolayer nanostructure.

An increase in the number of ligand binding sites on the surface of a biosensor, such as by the oligomerizing the engineered binding protein and linking the resulting oligomer to a polymerincrease the limit of detection of the biosensor. The limit of detection of a biosensor, as used herein, is the lowest quantity or concentration of analyte (e.g., ligand) that can be reliably detected by a component (e.g., protein) immobilized on a surface. Therefore, the lower the limit of detection of a biosensor, the better its ability to detect analyte (e.g., ligand) binding relative to a biosensor with a higher limit of detection.

In some embodiments, the disclosure provides a biosensor with a limit of detection for binding by the protein between 5 nM and 300 nM. In some embodiments, the disclosure provides a biosensor with a limit of detection for binding by the protein between 100 nM and 200 nM. In some embodiments, the disclosure provides a biosensor with a limit of detection for binding by the protein of at least 5 nM, at least 10 nM, at least 20 nM, at least 30 nM, at least 40 nM, at least 50 nM, at least 60 nM, at least 70 nM, at least 80 nM, at least 90 nM, or at least 100 nM. In some embodiments, the disclosure provides a biosensor with a limit of detection for binding by the protein of at least 110 nM, at least 120 nM, at least 130 nM, at least 140 nM, at least 150 nM, at least 160 nM, at least 170 nM, at least 180 nM, at least 190 nM, or at least 200 nM. In some embodiments, the disclosure provides a biosensor with a limit of detection for binding by the protein of at least 210 nM, at least 220 nM, at least 230 nM, at least 240 nM, at least 250 nM, at least 260 nM, at least 270 nM, at least 280 nM, at least 290 nM, or at least 300 nM.

In some aspects, the disclosure provides the immobilization of a protein-polymer conjugate on a surface. Numerous methods are utilized for immobilizing protein-polymer conjugates on a surface, including passive absorption, wherein the protein-polymer conjugates bind to the surface without additional chemicals; passive absorption followed by cross-linking, wherein the cross-linking prevents diffusion of the protein-polymer conjugates from the surface; and passivation of the surface by a silane molecule, such as aminosilane or (3-aminopropyl) triethoxysilane, prior to immobilization of the protein-polymer conjugate. Commonly utilized cross-linking agents include aldehydes, such as glutaraldehyde and formaldehyde, and ultraviolet light in concert with a cross-linking agent such as $Ru(BiPy)_3^{+2}$ or photoreactive diazirine analogs of leucine and methionine.

In some aspects, the disclosure provides the immobilization of protein-polymer conjugates on a surface in a biosensor. In some embodiments, the protein-polymer conjugate immobilized on a surface forms a thin-film. In some embodiments, the polymer is PNIPAM conjugated to an engineered binding protein. In some embodiments, the engineered binding protein is rcSso7d or rcSso7d-SA.

In some embodiments, the protein-polymer conjugate immobilization is in the presence of a cross-linking agent. In some embodiments, the cross-linking agent is glutaraldehyde. In some embodiments, the cross-linking agent is ultra-violet light with $Ru(BiPy)_3^{+2}$.

The protein-polymer conjugate described herein can be exemplified by the use of the rcSso7d-PNIPAM-MA protein-polymer conjugate bound to a surface (e.g., silicon, quartz, glass, cellulose-containing substrate, such as a chromatography paper (e.g., Whatman® Grade 1 Qualitative Filtration Paper), etc.) to form a biosensor. The biosensor can be contacted with a sample, such as a biological sample (e.g., urine), obtained from a subject, that contains a ligand of interest. The ligand of interest can be a urine-based biomarker obtained from a subject that has or is suspected of having a contagious disease, which, in some instances, may be used to determine whether the subject has the contagious disease.

Expression of Engineered Binding Protein

Also disclosed herein are nucleic acids that encode for any of the engineered binding protein proteins described herein, libraries that contain any of the nucleic acids and/or engineered binding proteins described herein, and compositions that contain any of the nucleic acids and/or engineered binding proteins described herein. It should be appreciated that libraries containing nucleic acids or proteins can be generated using methods known in the art. A library containing nucleic acids can contain fragments of genes and/or full-length genes and can contain wild-type sequences and mutated sequences. A library containing proteins can contain fragments of proteins and/or full length proteins and can contain wild-type sequences and mutated sequences.

The development and selection of a ligand-binding protein described herein, such as the rcSso7d.SA, can be produced by methods disclosed in Miller et al.[39]. Briefly, a ligand-binding protein, such as rcSso7d. SA is selected from a yeast surface display library based on the reduced-charge Sso7d scaffold (rcSso7d). The yeast library can be generated using trinucleotide oligo synthesis and in vivo homologous recombination with a linearized plasmid, such as the pCTcon2 plasmid.[42] Methods of isolation, such as the highly-avid magnetic bead sorting[48] and fluorescence-activated cell sorting (FACS)[49] can be employed to select binders against a ligand of interest, such as streptavidin, and stringency increased over rounds of FACS-based library screening, after which a sub-library can be sequenced and the ligand-binding protein that binds the ligand of interest (e.g., rcSso7d.SA) can be selected for further characterization, such as robust expression in a system, such as a bacterial system, for downstream applications. Additional methods for creating a yeast surface display library include methods known to one of ordinary skill in the art.

In some embodiments, one or more of the engineered binding proteins, ligands, etc. disclosed herein are expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA (RNA).

A nucleic acid molecule that encodes a bifunctional fusion protein or antigen or any other molecule disclosed herein can be introduced into a cell or cells using methods and techniques that are standard in the art. For example, nucleic acid molecules can be introduced by standard protocols such as transformation including chemical transformation and electroporation, transduction, particle bombardment, etc.

Any type of cell that can be engineered to recombinantly express genes can be used in the methods described herein, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp. (*e.g., S. cerevisiae*), *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Other examples of fungi include *Aspergillus* spp., *Penicillium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell, or a plant cell.

Ligand Detection

In some aspects, methods for detecting a ligand of interest are also provided herein. In some embodiments, the methods include contacting any of the protein-polymer conjugates described herein with a surface for a time sufficient for the protein-polymer conjugate to bind to the surface; contacting the protein-polymer conjugate bound to the surface with a sample comprising a ligand of interest; and detecting the ligand of interest bound by the engineered binding protein, such as the reduced charge Sso7d protein exemplified herein (e.g., rcSso7d-SA). In some embodiments, the methods include obtaining a biosensor comprising any of the protein-polymer conjugates described bound to a surface of the biosensor; contacting the protein-polymer conjugate bound to the surface with a sample comprising a ligand of interest; and detecting the ligand of interest bound by the engineered binding protein, such as the reduced charge Sso7d protein exemplified herein (e.g., rcSso7d-SA).

In some embodiments, the method includes contacting any of the protein-polymer conjugates described herein with a sample comprising a ligand of interest, wherein the ligand of interest binds to the protein-polymer conjugate and forms a complex; contacting the complex with a surface for a time sufficient for the complex to bind to the surface; and detecting the ligand of interest bound by the engineered binding protein, such as the reduced charge Sso7d ligand-binding protein exemplified herein.

In some embodiments, the protein-polymer conjugate or the complex is in solution. In some embodiments, the solution includes a buffer, such as a buffer known to one of ordinary skill in the art. The protein-polymer conjugate may be in solution at a desired concentration. In some embodiments, the protein-polymer conjugate is at a desired concentration of or about 5 µM, of or about 10 µM, of or about 15 µM, of or about 20 µM, of or about 25 µM, of or about 30 µM, of or about 35 µM, of or about 40 µM, of or about 45 µM, of or about 50 µM, of or about 60 µM, of or about 70 µM, of or about 80 µM, of or about 90 µM, of or about 100 µM, of or about 200 µM, of or about 300 µM, or of or about 400 µM.

In some embodiments, the protein-polymer conjugate described herein is contacted with the surface for about 5 seconds, about 15 seconds, about 20 seconds, about 30 seconds, about 35 seconds, about 40 seconds, about 45 seconds, about 1 minute, about 1.5 minutes, about 2 minutes, about 2.5 minutes, about 3 minutes, about 4 minutes, about 5 minutes, about 7 minutes, about 10 minutes, about 15 minutes, about 20 minutes, about 30 minutes, or about 1 hour.

In some embodiments, the protein-polymer conjugate bound to the surface is contacted with a sample that contains a ligand of interest. In some embodiments, the protein-polymer conjugate described herein is contacted with a sample comprising a ligand of interest, wherein the ligand of interest binds to the protein-polymer conjugate and forms a complex; the complex is then contacted with a surface for a time sufficient for the complex to bind to the surface.

In some embodiments, the sample is a biological sample. The biological sample may be obtained from a subject. As described herein, the term "biological sample" is used to generally refer to any biological material obtained from a subject. The biological sample typically is a fluid sample. Solid tissues may be made into fluid samples using routine methods in the art. In some embodiments, the biological sample is tissue, feces, or a cell obtained from a subject. In some embodiments, the biological sample comprises a bodily fluid from a subject. The bodily fluids can be fluids isolated from anywhere in the body of the subject, preferably a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, intra-organ system fluid, ascitic fluid, tumor cyst fluid, amniotic fluid or combinations thereof.

In some embodiments, the surface is composed of a semi-conductor material (e.g., silicon). In certain embodiments, the semi-conductor material is modified in an oxidizing chemical bath to yield covalent chemical linkage of the protein to the substrate, passivated with a blocking agent[58,59] to reduce non-specific protein adsorption to the substrate, or pre-incubated with a stabilizing species such as trehalose in order to improve assay functionality and stability. In certain embodiments, the semi-conductor material is not modified (unmodified). In some embodiments, the semi-conductor material is an unmodified semi-conductor material, such as a Wafer World P-type Silicon with boron as dopant, (100) orientation, single-side polished. In some embodiments, the semi-conductor material is sequentially rinsed with acetone, methanol, and water, followed by drying and treatment with oxygen plasma for 3 minutes.

Additional non-limiting examples of surfaces contemplated herein include quartz, glass, paper, cellulose, and nitrocellulose.

For instance, a non-limiting example is the use of rcSso7d-PNIPAM-MA protein-polymer conjugate bound to a semi-conductor surface, such as a silicon wafer (e.g., Wafer World P-type Silicon with boron as dopant, (100) orientation, single-side polished) which is contacted with a sample that contains a ligand of interest, such as an urine-based biomarker of a contagious disease obtained from a subject that has or is suspected of having a contagious disease, which, in some instances, may be used to determine whether the subject has the contagious disease.

In some embodiments, the antigen of interest is streptavidin.

In some embodiments, at least or about 0.1 micromole, at least or about 0.2 micromoles, at least or about 0.3 micromoles, at least or about 0.4 micromoles, at least or about 0.5 micromoles, at least or about 0.6 micromoles, at least or about 0.7 micromoles, at least or about 0.8 micromoles, at least or about 0.9 micromoles, at least or about 1 micromole, at least or about 1.1 micromoles, at least or about 1.2 micromoles, at least or about 1.3 micromoles, at least or about 1.4 micromoles, at least or about 1.5 micromoles, at least or about 1.6 micromoles, at least or about 1.7 micromoles, at least or about 1.8 micromoles, at least or about 1.9 micromoles, at least or about 2 micromoles, at least or about 2.1 micromoles, at least or about 2.2 micromoles, at least or about 2.3 micromoles, at least or about 2.4 micromoles, at least or about 2.5 micromoles, at least or about 2.6 micromoles, at least or about 2.7 micromoles, at least or about 2.8 micromoles, at least or about 2.9 micromoles, at least or about 3 micromoles, at least or about 3.5, at least or about 4 micromoles, at least or about 4.5 micromoles, or at least or about 5 micromoles of any of the protein-polymer conjugates described herein are attached to a silicon surface per gram of silicon of the silicon-containing substrate.

In some embodiments, at least or about 1 µM, at least or about 25 µM, at least or about 50 µM, at least or about 60 µM, at least or about 70 µM, at least or about 80 µM, at least or about 90 µM, at least or about 100 µM, at least or about 150 µM, at least or about 200 µM, at least or about 250 µM, at least or about 300 µM, at least or about 350 µM, at least or about 400 µM, at least or about 500 µM, at least or about 550 µM, at least or about 600 µM, at least or about 650 µM, at least or about 700 µM, at least or about 750 µM, at least or about 800 µM, at least or about 850 µM, at least or about 900 µM, at least or about 950 µM, at least or about 1 mM, at least or about 1.5 mM, at least or about 2 mM, at least or about 2.5 mM, at least or about 3 mM, at least or about 3.5 mM, at least or about 4 mM, at least or about 4.5 mM, at least or about 5 mM of volume-average concentrations any of the protein-polymer conjugates described herein are attached to a surface.

In some aspects, the molar abundance or molar excess of the engineered binding protein in the protein-polymer conjugate, such as an rcSso7d oligomer, relative to the ligand of interest allows the rapid capture and, in some embodiments, efficient and complete depletion of the ligand of interest from a sample.

In some embodiments, at least or about a 10-fold molar excess of the protein-polymer conjugate or engineered binding protein completely depletes a ligand of interest from a sample or solution. In some embodiments, at least or about a 10-fold volume-average concentration excess leads to rapid capture and/or immobilization of a protein-polymer conjugate or engineered binding protein.

In some embodiments, the protein-polymer conjugate is in molar excess of the ligand of interest. In some embodiments, the protein-polymer conjugate is in at least or about 2-fold molar excess, at least or about 3-fold molar excess, at least or about 4-molar excess, at least or about 5-fold molar excess, at least or about 6-fold molar excess, at least or about 7-fold molar excess, at least or about 8-fold molar excess, at least or about 9-fold molar excess, at least or about 10-fold molar excess, at least or about 15-fold molar excess, at least or about 20-fold molar excess, at least or about 25-fold molar excess, at least or about 30-fold molar excess, at least or about 35-fold molar excess, at least or about 40-fold molar excess, at least or about 45-fold molar excess, at least or about 50-fold molar excess, at least or about 60-fold molar excess, at least or about 65-fold molar excess, at least or about 70-fold molar excess, at least or about 80-fold molar excess, at least or about 90-fold molar excess, at least or about 100-fold molar excess, at least or about 200-fold molar excess, at least or about 300-fold molar excess, at least or about 400-fold molar excess, at least or about 500-fold molar excess, at least or about 600-fold molar excess, at least or about 700-fold molar excess, at least or about 800-fold molar excess, at least or about 900-fold molar excess, at least or about 1000-fold molar excess, at least or about 1500-fold molar excess, or at least or about 2000-fold molar excess relative to the ligand of interest in the sample.

In some embodiments, the protein-polymer conjugate is in such excess that the ligand of interest is depleted from the sample. In some embodiments, about or at least 10%, about or at least 20%, about or at least 30%, about or at least 40%, about or at least 50%, about or at least 55%, about or at least 60%, about or at least 65%, about or at least 70%, about or at least 75%, about or at least 80%, about or at least 81%, about or at least 82%, about or at least 83%, about or at least 84%, about or at least 85%, about or at least 86%, about or at least 87%, about or at least 88%, about or at least 89%, about or at least 90%, about or at least 91%, about or at least 92%, about or at least 93%, about or at least 94%, about or at least 95%, about or at least 95.5%, about or at least 96%, about or at least 96.5%, about or at least 97%, about or at least 97.5%, about or at least 98%, about or at least 98.5%, about or at least 99%, about or at least 99.5%, or about 100% of the ligand of interest is depleted from the sample, such as a biological sample.

In some aspects, standard curves can be prepared given the advantageous properties of the disclosure in which complete or near-complete depletion of a ligand of interest can be achieved from a sample or solution. The abundance of the captured ligand can be detected and measured or determined using a readout, such as a fluorescent readout or a colorimetric readout.

In some embodiments, the surface-immobilized concentration of the engineered binding protein (e.g., rcSso7d-PNIPAM) is quantified using a protein assay, such as a micro bicinchoninic acid (BCA) assay. A standard curve can be prepared by evaporating known quantities of protein onto cellulose test zones, depositing these test zones into the wells of a micro BCA assay, and quantifying the signal development in this format. The same procedure is followed for the experimental samples (following the substrate washing step), and the associated signal for each sample is then mapped to this standard curve in order to determine the mass of immobilized rcSso7d-PNIPAM.

In some embodiments, the sample is a biological sample from a subject. A subject includes, but is not limited to, any mammal, such as a human, a primate, a mouse, a rat, a dog, a cat, a horse, or agricultural stocks (e.g., fish, pigs, cows, sheep, and birds—particularly chickens). In certain embodiments, the subject is a human. In some embodiments, the sample is a solution, such as a buffer solution.

In some embodiments, the surface is rinsed with a buffer solution before detecting the ligand of interest bound to the engineered reduced charge Sso7d engineered binding protein (e.g., rcSso7d). In some embodiments, the buffer is phosphate buffered saline (PBS) or another buffer known to one of ordinary skill in the art that provides a stable environment for a macromolecule, such as a protein, protein complex, ligand, etc.

In some embodiments, the method further includes detecting the ligand of interest bound by the engineered reduced charge Sso7d engineered binding protein (e.g., rcSso7d) in the protein-polymer conjugate. In some embodiments, the ligand of interest bound to the protein-polymer conjugate is contacted with a surface in which the protein-polymer conjugate binds the surface (e.g., silicon such as Wafer World P-type Silicon with boron as dopant, (100) orientation, single-side polished). The method allows for the separation or isolation of the ligand of interest from any other molecules that may be present in a sample, such as a biological sample (e.g., urine). In some embodiments, the presence or amount of the ligand of interest is determined or measured using a signal-generating reagent that specifically recognizes the ligand of interest and generates a signal. In some embodiments, protein-polymer conjugate (e.g., rcSso7d-PNIPAM) would be immobilized on a semi-conductor surface (e.g., silicon wafer, etc.), and would then be brought into contact with the solution/biological sample bearing the ligand of interest (either forced convection to draw the fluid across or through the test zone, or soluble co-incubation of the protein-polymer conjugate and the ligand). This immobilized complex would then be contacted with a second, epitope-specific variant of rcSso7d (not conjugated to PNIPAM, but fused instead to a biotin acceptor sequence, or modified with a fluorophore). The second species (e.g., rcSso7d) would bind to a second epitope of the captured ligand. This second species would be conjugated to a means of transducing this binding reaction; several examples are outlined below. All of these steps could be done directly on the semi-conductor surface. Non-limiting examples of signal-generating that can be fused to the engineered binding protein (e.g., rcSso7d) include, without limitation, gold nanoparticles, enzymes (expressed as fusion partners or indirectly bound to rcSso7d) which yield a colorimetric response, enzymes which yield an amperometric or impedometric signal (e.g., glucose oxidase), a macrophotoinitiator which can initiate a polymerization reaction, cellulose nanobeads, other metallic nanoparticles, dye-filled liposomes, DNA which can be amplified enzymatically, RNA which can be expressed for the production of a color-producing enzyme, etc. The presence or amount of the signal-generating reagent can be detected using an imaging device, such as a digital imager. Additional non-limiting examples of detecting the signal-generating reagent include gold nanoparticles, which can be used in a point-of-care setting, and are the reagents used in traditional pregnancy tests. The spatial localization of gold nanoparticles, mediated by the ligand-binding interaction, concentrates the optical signal (which is also amplified by the occurrence of surface plasmon resonance). This can be detected by the naked eye. Polymerization-based amplification would use the localization of a macrophotoinitiator in order to yield a rapid, durable polymerization response following incubation with a monomer solution and irradiation with the appropriate wavelength of light. Entrained phenolphthalein yields a high-contrast colorimetric readout following the application of a basic solution, which can be detected with the naked eye. An amperometric method, such as fusing glucose oxidase to the second rcSso7d species and contacting the tests with gold probes and a glucose solution, would allow for smart phone based detection. Enzymatic methods can also be used, and rely upon a fusion of the second species (e.g., rcSso7d) to an enzyme and contacting the tests with a labile substrate which becomes colored following enzymatic cleavage. Impedometric means of detecting the signal generating reagent are also possible, and can be achieved using smartphone-compatible adaptors.

In some aspects, provided herein are also methods for enhancing the sensitivity of an assay. The method includes binding of a ligand to a engineered binding protein, which includes conjugating an engineered binding protein that binds to a ligand of interest to a polymer. Any engineered binding protein that can be conjugated to a polymer can benefit from its favorable properties; the high immobilized abundance of protein-polymer conjugate results in high molar abundance of the binding species, thereby allowing, in some instances, depletion of a ligand of interest and a high local concentration of this species, thereby allowing, in some instances, rapid capture of a ligand of interest. In some embodiments, the ligand of interest is in solution. In contrast to traditional immunoassays in which the immobilized binding partner is the limiting reagent and the ligand of interest is captured slowly and incompletely, the present disclosure allows for the ligand capture/detection to rapidly proceed to completion. Additionally, because the protein-polymer conjugate, and thus the engineered binding protein, is at a high local abundance, this allows the use of higher sample volumes containing higher amounts of ligand, which would be captured and depleted, in some instances, to provide high signal over a method previously available in the art in which the engineered binding protein is actually the limiting reagent, reducing the amount of ligand that can be captured and detected at a given point. This could be applied to any binding scaffold by conjugating the binding scaffold to a polymer.

Diseases and Conditions

The protein-polymer conjugates, compositions, methods and kits described herein can be used to detect the presence of molecules, such as ligands, that are generated in response to various diseases or conditions. Non-limiting examples of diseases or conditions that generate molecules, such as ligands, which can be detected include a disease or condition that releases a ligand of interest, such as cancer, cardiovascular diseases, infectious diseases, liver diseases, such as liver failure, Alzheimer's disease, Parkinson's disease, or autoimmune diseases. Any condition which has an associated biochemical signature can theoretically be detected.

The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g., small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In some embodiments, the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

Infectious diseases can be caused by bacteria, viruses, fungi, or parasites. Bacteria are responsible for illnesses such as strep throat, urinary tract infections and tuberculosis. Viruses cause a multitude of diseases, ranging from the common cold to AIDS. Fungi cause several skin diseases, such as ringworm and athlete's foot, or can also affect the lungs and/or nervous system. Parasites can cause diseases such as malaria.

Autoimmune disease is a class of diseases in which an subject's own antibodies react with host tissue or in which immune effector T cells are autoreactive to endogenous self-peptides and cause destruction of tissue. Thus, an immune response is mounted against a subject's own antigens, referred to as self-antigens. Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjögren's syndrome, insulin resistance, and autoimmune diabetes mellitus.

In some embodiments, the disease or condition is prostate cancer and the antigen that can be detected is PSA. In some embodiments, the disease or condition is cardiac arrest and the antigen of interest that can be detected is troponin. In some embodiments, the disease or condition is Alzheimer's disease and the antigen of interest that can be detected is tau protein. In some embodiments, the disease or condition is HIV and the antigen of interest that can be detected is IP-10. In some embodiments, the disease or condition is Schistomiasis and the antigen of interest that can be detected is Schistosome GST. In some embodiments, the disease or condition is ovarian cancer and the antigen of interest that can be detected is CA-125. In some embodiments, the disease or condition is lyme disease and the antigen of interest that can be detected is ospA.

In some embodiments, ligands or ligands of interest produced by vector-borne diseases (e.g., chikungunya, Chagas, Ebola, bubonic plague, Lyme disease, brucellosis, encephalitis, etc.) are also contemplated herein; by food/water-borne illness (e.g., diarrhea, cholera, schistomiasis, bovine spongiform encephalopathy (prion), etc.) are also contemplated herein; by patient-to-patient transmitted infectious disease (e.g., tuberculosis (ESAT-6/CFP-10/Rv1656/LAM), HIV (CD32a), influenza (HA), rhinitis, pneumonia, bronchitis, syphilis, gonorrhea, hepatitis AB/C, HPV, etc.) are also contemplated herein; by chronic diseases (diabetes/pre-diabetes (glycated hemogloblin), anemia (hemoglobin), liver cirrhosis, cardiac arrest (troponin), Alzheimer's disease, autoimmune disease, etc.) are also contemplated herein. General health assays (protein urine analysis, etc.), livestock assays, companion diagnostics for cancer therapeutics are also contemplated herein.

Compositions

In some aspects, compositions of the protein-polymer conjugate described herein are also provided. In some embodiments, the composition includes any of the protein-polymer conjugate described herein bound to a surface. In some embodiments, the surface comprises a semi-conductor material (e.g., silicon). In certain embodiments, the semi-conductor material is modified in an oxidizing chemical bath to yield covalent chemical linkage of the protein to the substrate, passivated with a blocking agent[58,59] to reduce non-specific protein adsorption to the substrate, or pre-incubated with a stabilizing species such as trehalose in order to improve assay functionality and stability. In certain embodiments, the semi-conductor material is not modified (unmodified). In some embodiments, the semi-conductor material is an unmodified semi-conductor material, such as a Wafer World P-type Silicon with boron as dopant, (100) orientation, single-side polished. In some embodiments, the semi-conductor material is sequentially rinsed with acetone, methanol, and water, followed by drying and treatment with oxygen plasma for 3 minutes. Additional non-limiting examples of surfaces contemplated herein include quartz, glass, paper, cellulose, and nitrocellulose.

In some embodiments, at least or about 0.1 micromole, at least or about 0.2 micromoles, at least or about 0.3 micromoles, at least or about 0.4 micromoles, at least or about 0.5 micromoles, at least or about 0.6 micromoles, at least or about 0.7 micromoles, at least or about 0.8 micromoles, at least or about 0.9 micromoles, at least or about 1 micromole, at least or about 1.1 micromoles, at least or about 1.2 micromoles, at least or about 1.3 micromoles, at least or about 1.4 micromoles, at least or about 1.5 micromoles, at least or about 1.6 micromoles, at least or about 1.7 micromoles, at least or about 1.8 micromoles, at least or about 1.9 micromoles, at least or about 2 micromoles, at least or about 2.1 micromoles, at least or about 2.2 micromoles, at least or about 2.3 micromoles, at least or about 2.4 micromoles, at least or about 2.5 micromoles, at least or about 2.6 micromoles, at least or about 2.7 micromoles, at least or about 2.8 micromoles, at least or about 2.9 micromoles, at least or about 3 micromoles, at least or about 3.5 micromoles, at least or about 4 micromoles, at least or about 4.5 micromoles, or at least or about 5 micromoles of any of the protein-polymer conjugates described herein are attached to a silicon surface per gram of silicon of the silicon-containing substrate.

In some embodiments, at least or about 1 μM, at least or about 25 μM, at least or about 50 μM, at least or about 60 μM, at least or about 70 μM, at least or about 80 μM, at least or about 90 μM, at least or about 100 μM, at least or about 150 μM, at least or about 200 μM, at least or about 250 μM, at least or about 300 μM, at least or about 350 μM, at least or about 400 μM, at least or about 500 μM, at least or about 550 μM, at least or about 600 μM, at least or about 650 μM, at least or about 700 μM, at least or about 750 μM, at least or about 800 μM, at least or about 850 μM, at least or about 900 μM, at least or about 950 μM, at least or about 1 mM, at least or about 1.5 mM, at least or about 2 mM, at least or about 2.5 mM, at least or about 3 mM, at least or about 3.5 mM, at least or about 4 mM, at least or about 4.5 mM, at least or about 5 mM of volume-average concentration of any of the protein-polymer conjugates described herein are attached to a surface.

Kits

In some aspects, the protein-polymer conjugates and compositions described herein are provided in a kit. In some embodiments, the kit is used to assess the presence or amount of a molecule, such as a ligand or a ligand of interest and includes a container containing any of the protein-polymer conjugates described herein.

In some embodiments, the kit further comprises a surface. In some embodiments, the protein-polymer conjugate is bound to a surface comprising a semi-conductor material (e.g., silicon). In some embodiments, at least or about 0.1 micromole, at least or about 0.2 micromoles, at least or about 0.3 micromoles, at least or about 0.4 micromoles, at least or about 0.5 micromoles, at least or about 0.6 micromoles, at least or about 0.7 micromoles, at least or about 0.8 micromoles, at least or about 0.9 micromoles, at least or about 1 micromole, at least or about 1.1 micromoles, at least or about 1.2 micromoles, at least or about 1.3 micromoles, at least or about 1.4 micromoles, at least or about 1.5 micromoles, at least or about 1.6 micromoles, at least or about 1.7 micromoles, at least or about 1.8 micromoles, at least or about 1.9 micromoles, at least or about 2 micromoles, at least or about 2.1 micromoles, at least or about 2.2 micromoles, at least or about 2.3 micromoles, at least or about 2.4 micromoles, at least or about 2.5 micromoles, at least or about 2.6 micromoles, at least or about 2.7 micromoles, at least or about 2.8 micromoles, at least or about 2.9 micromoles, at least or about 3 micromoles, at least or about 3.5, at least or about 4 micromoles, at least or about 4.5 micromoles, or at least or about 5 micromoles of any of the protein-polymer conjugates described herein are attached to a silicon surface per gram of silicon of the silicon-containing substrate.

In some embodiments, at least or about 1 μM, at least or about 25 μM, at least or about 50 μM, at least or about 60 μM, at least or about 70 μM, at least or about 80 μM, at least or about 90 μM, at least or about 100 μM, at least or about 150 μM, at least or about 200 μM, at least or about 250 μM, at least or about 300 μM, at least or about 350 μM, at least or about 400 μM, at least or about 500 μM, at least or about 550 μM, at least or about 600 μM, at least or about 650 μM, at least or about 700 μM, at least or about 750 μM, at least or about 800 μM, at least or about 850 μM, at least or about 900 μM, at least or about 950 μM, at least or about 1 mM, at least or about 1.5 mM, at least or about 2 mM, at least or about 2.5 mM, at least or about 3 mM, at least or about 3.5 mM, at least or about 4 mM, at least or about 4.5 mM, at least or about 5 mM of volume-concentration of any of the protein-polymer conjugates described herein are attached to a surface.

In some embodiments, the composition includes any of the protein-polymer conjugate described herein bound to a surface. In some embodiments, the surface comprises a semi-conductor material (e.g., silicon). In certain embodiments, the semi-conductor material is modified in an oxidizing chemical bath to yield covalent chemical linkage of the protein to the substrate, passivated with a blocking agent[58,59] to reduce non-specific protein adsorption to the substrate, or pre-incubated with a stabilizing species such as trehalose in order to improve assay functionality and stability. In certain embodiments, the semi-conductor material is not modified (unmodified). In some embodiments, the semi-conductor material is an unmodified semi-conductor material, such as a Wafer World P-type Silicon with boron as dopant, (100) orientation, single-side polished. In some embodiments, the semi-conductor material is sequentially rinsed with acetone, methanol, and water, followed by drying and treatment with oxygen plasma for 3 minutes. Additional non-limiting examples of surfaces contemplated herein include quartz, glass, paper, cellulose, and nitrocellulose

EXAMPLES

Materials and Methods
Synthesis.

Figure 8:
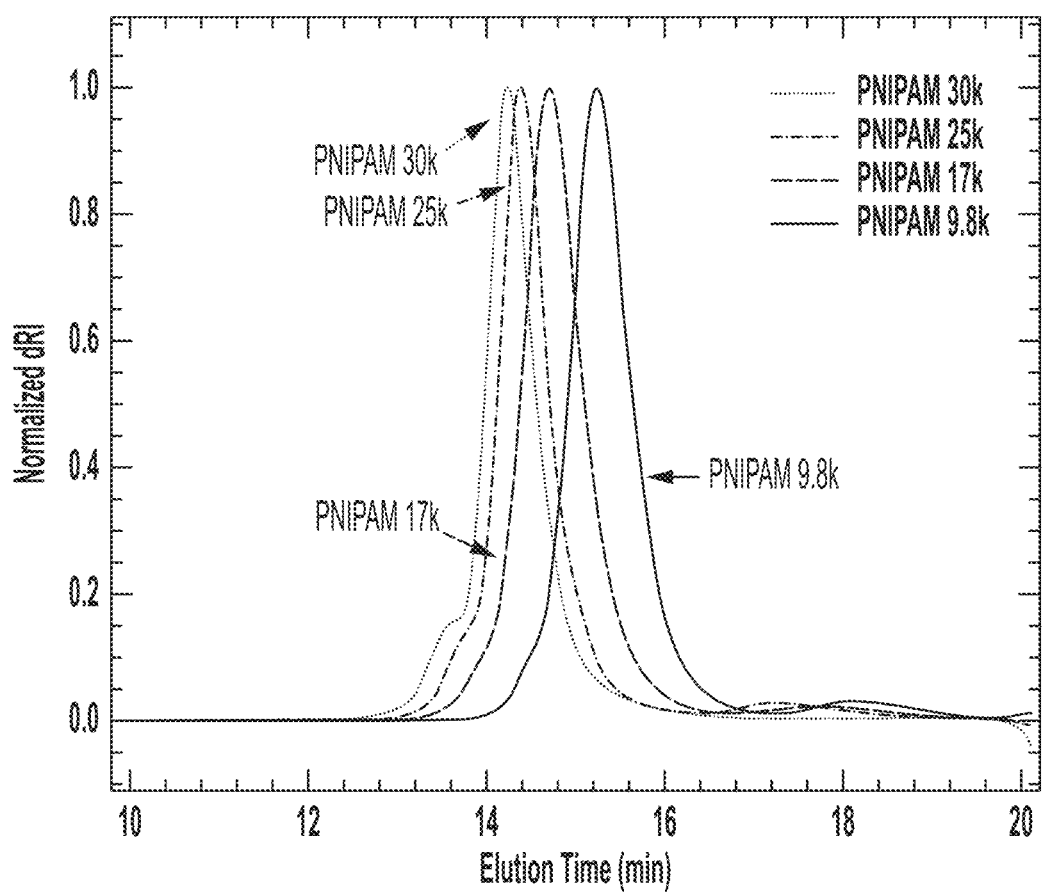
FIG. 8. Normalized differential refractive index signals from gel permeation chromatography of PNIPAM samples. The small shoulder at earlier elution times corresponding to twice the peak molecular weight in some samples results from slight reactivity of the double bond in the furan-protected maleimide of the CTA, as reported previously.[21]

Poly(N-isopropylacrylamide) (PNIPAM) functionalized with a maleimide group was synthesized by reversible addition-fragmentation chain transfer (RAFT) polymerization, as described previously.[21] Polymer molecular weight and dispersity were characterized by gel permeation chromatography performed on an Agilent 1260 LC system equipped with two columns (ResiPore, 300×7.5 mm, up to 500k Da, Agilent Technologies, CA) in series, a Wyatt miniDAWN TREOS multi-angle light scattering detector, and a Wyatt Optilab T-rEX diffractometer (FIG. 8). DMF with 0.02 LiBr was used as the mobile phase with a flow rate of 1 mL/min at 70° C.

Figure 9A:
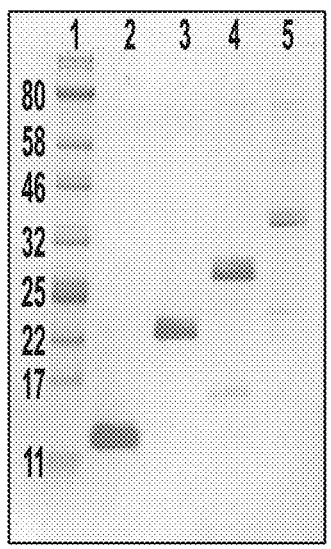
FIGS. 9A-9C. Denaturing protein gels of (FIG. 9A) Sso7d.SA oligomers and (FIG. 9B) bioconjugates, and (FIG. 9C) native protein gel of bioconjugates. Lanes 1-5 in (FIG. 9A) represent ladder and 1×rcSso7d.SA, 2×rcSso7d.SA, 3×rcSso7d.SA, and 4×rcSso7d.SA, respectively. Lanes 1-5 in (FIG. 9B) and (FIG. 9C) represent ladder, 1×SP9.8k, 2×SP17k, 3×SP25k, and 4×SP30k, respectively. All ladders represent molecular weight in kDa. Minor impurities in denaturing gel (FIG. 9B) are primarily the result of hydrolysis of an ester linkage between protein and PNIPAM during heating of samples; integration of the bands in native gel (FIG. 9C) reveals that all conjugate samples are >98% pure.
Figure 10B:
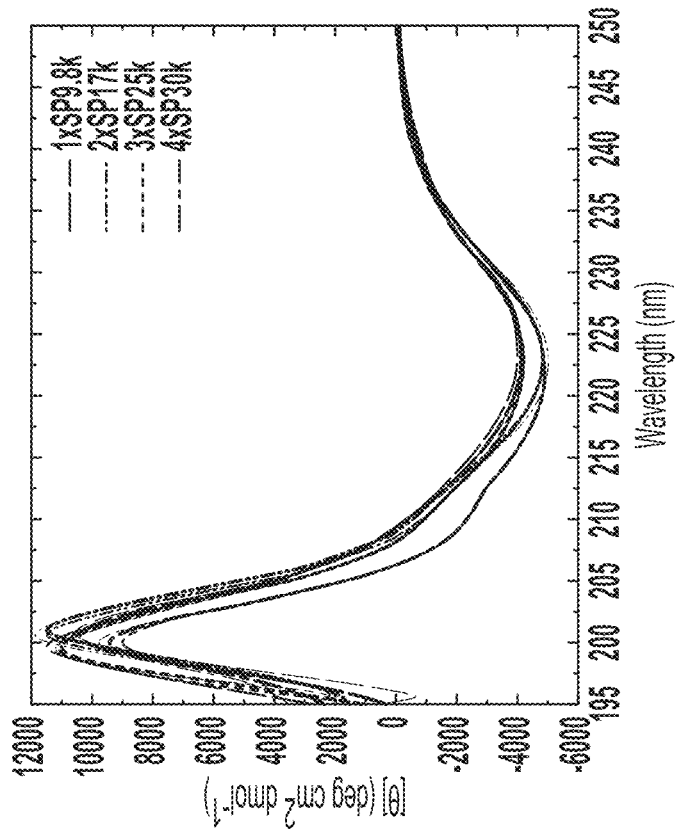
FIGS. 10A-10B. Circular dichroism spectroscopy of (FIG. 10A) rcSso7d.SA oligomers and (FIG. 10B) rcSso7d.SA-PNIPAM conjugates before dehydration and after rehydration of solid conjugate pellets confirm minimal change in secondary structure. In (FIG. 10B) light lines represent the corresponding unconjugated rcSso7d. SA oligomer, dashed lines represent conjugates before dehydration, and dark lines represent conjugates after rehydration. All rcSso7d.SA oligomers were measured in 50 mM Tris buffer, 100 mM NaCl, 0.25 mM TCEP, pH 7.4. Conjugates were measured in MilliQ water. Measurements were performed at 25° C.
Figure 10A:
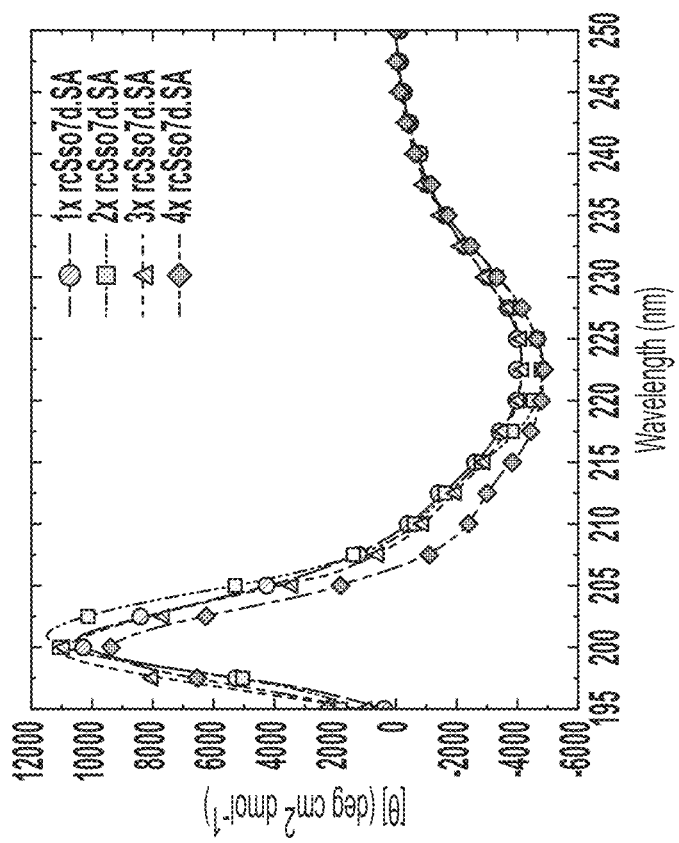
Figure 11:
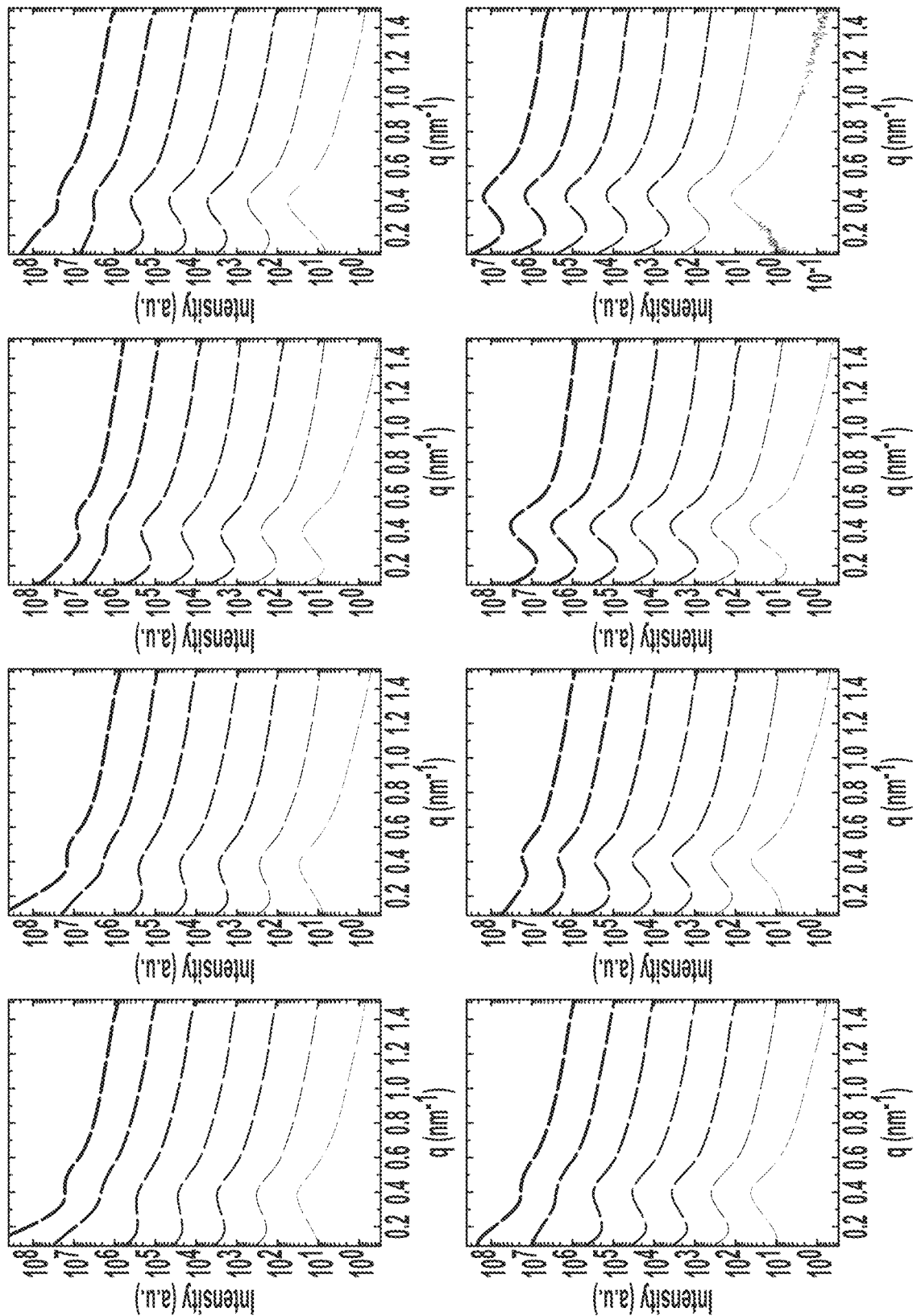
FIG. 11. Radially averaged SAXS patterns for 1×SP9.8k. Top row (left to right): 30 wt. %, 35 wt. %, 40 wt. %, 45 wt. %. Bottom row (left to right): 50 wt. %, 60 wt. %, 70 wt. %, 100 wt. %. Curves are offset vertically for clarity. The seven curves in each plot correspond to temperatures of 10° C. to 40° C. in 5° C. intervals, from bottom to top.
Figure 12:
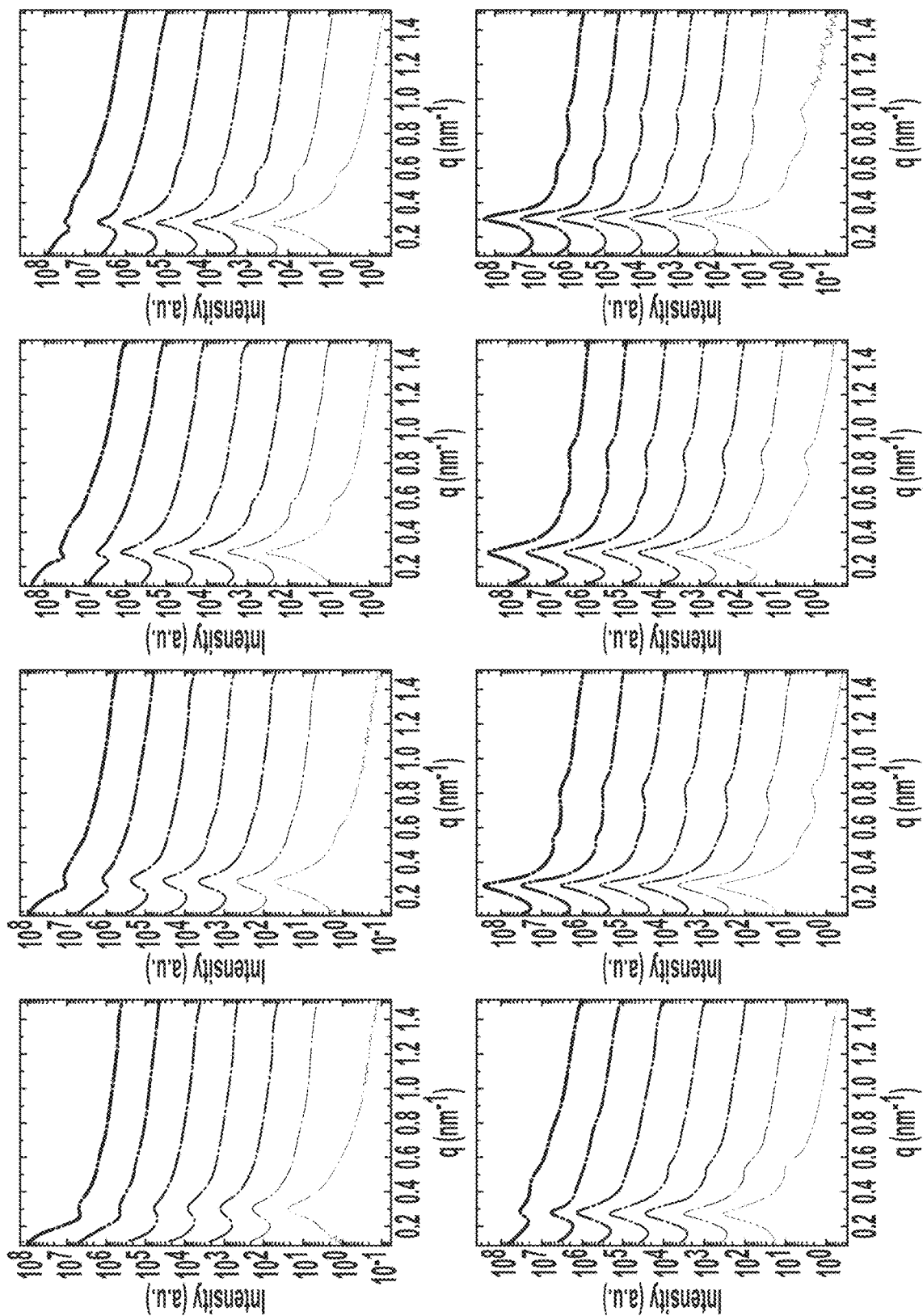
FIG. 12. Radially averaged SAXS patterns for 2×SP17k. Top row (left to right): 30 wt. %, 35 wt. %, 40 wt. %, 45 wt. %. Bottom row (left to right): 50 wt. %, 60 wt. %, 70 wt. %, 100 wt. %. Curves are offset vertically for clarity. The seven curves in each plot correspond to temperatures of 10° C. to 40° C. in 5° C. intervals, from bottom to top.
Figure 13:
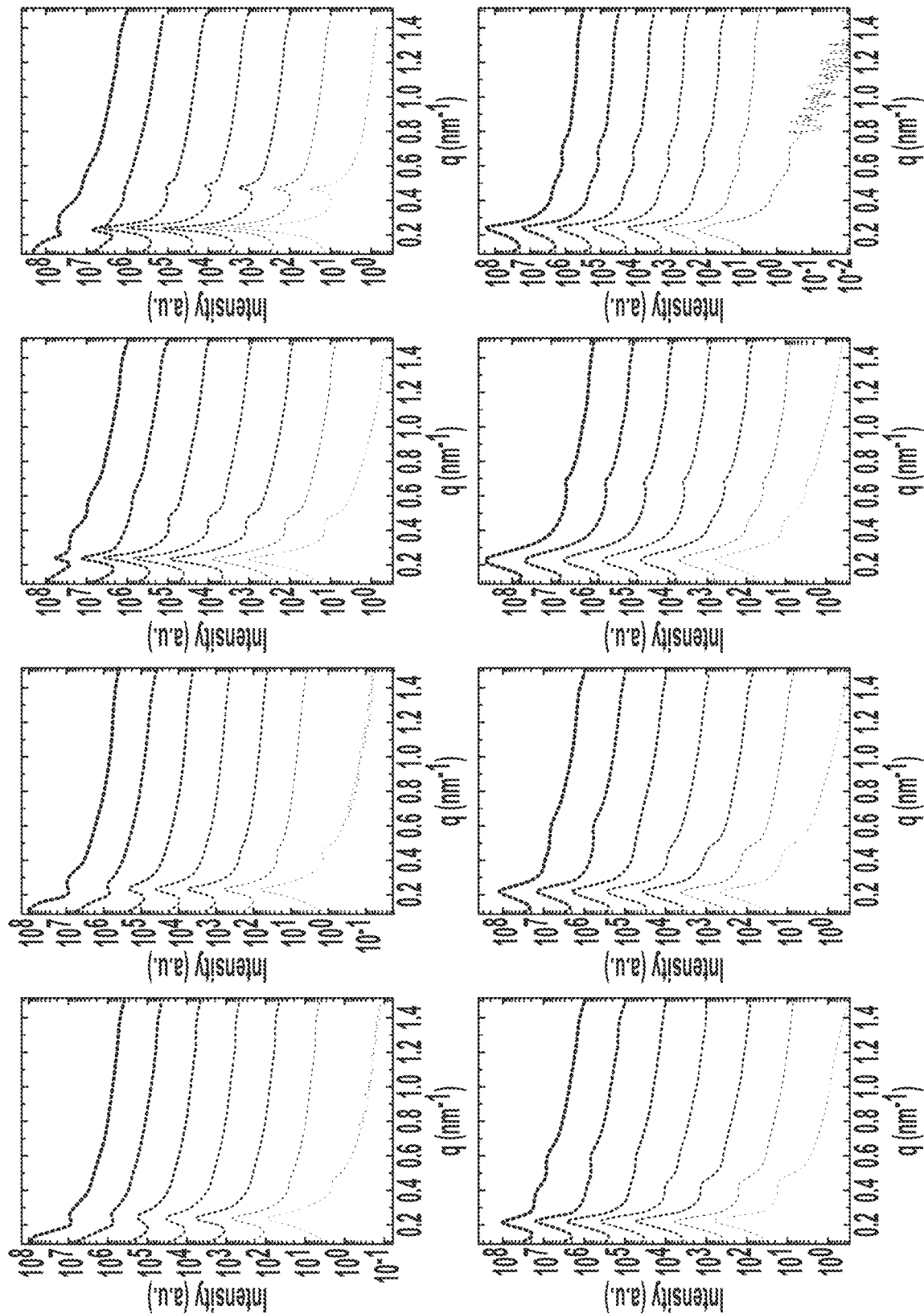
FIG. 13. Radially averaged SAXS patterns for 3×SP25k. Top row (left to right): 30 wt. %, 35 wt. %, 40 wt. %, 45 wt. %. Bottom row (left to right): 50 wt. %, 60 wt. %, 70 wt. %, 100 wt. %. Curves are offset vertically for clarity. The seven curves in each plot correspond to temperatures of 10° C. to 40° C. in 5° C. intervals, from bottom to top.
Figure 14:
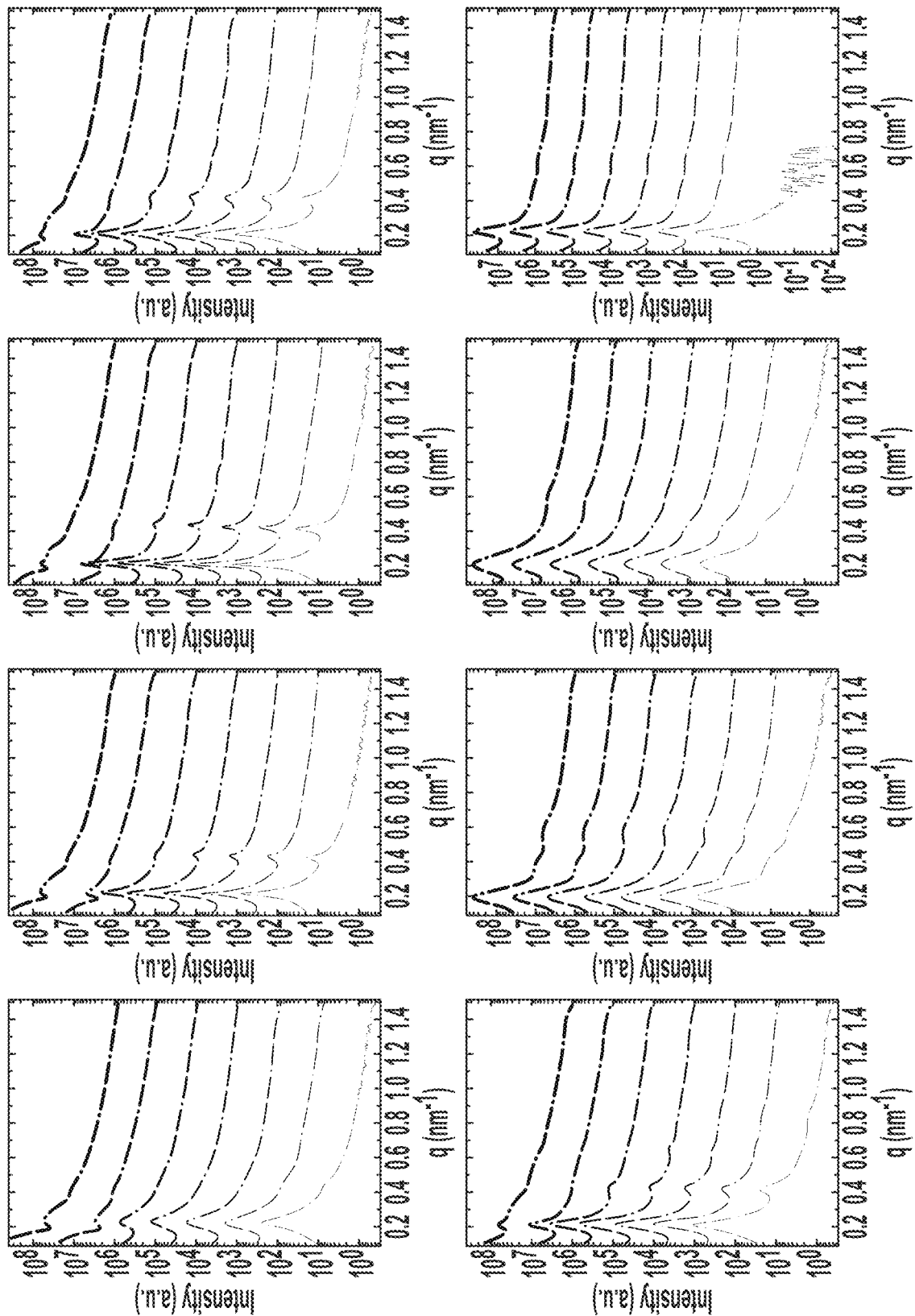
FIG. 14. Radially averaged SAXS patterns for 4×SP30k. Top row (left to right): 30 wt. %, 35 wt. %, 40 wt. %, 45 wt. %. Bottom row (left to right): 50 wt. %, 60 wt. %, 70 wt. %, 100 wt. %. Curves are offset vertically for clarity. The seven curves in each plot correspond to temperatures of 10° C. to 40° C. in 5° C. intervals, from bottom to top.
Figure 15A:
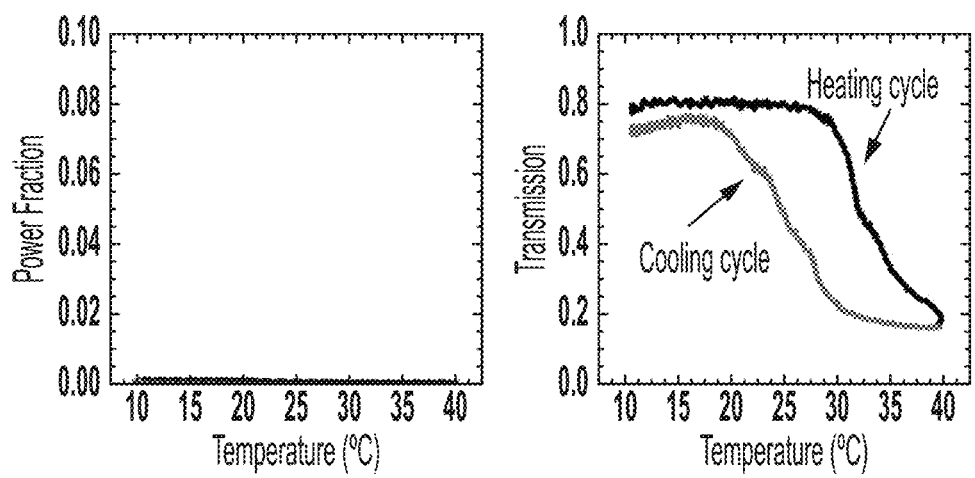
FIGS. 15A-15H. DPLS and turbidimetry heating/cooling cycles for 1×SP9.8k at (FIG. 15A) 30 wt. %, (FIG. 15B) 35 wt. %, (FIG. 15C) 40 wt. %, (FIG. 15D) 45 wt. %, (FIG. 15E) 50 wt. %, (FIG. 15F) 60 wt. %, (FIG. 15G) 70 wt. % and (FIG. 15H) 100 wt. %. The curves represent the heating cycle, the cooling cycle, and the 10-minute equilibration at the end of the heating cycle before cooling.
Figure 15B:
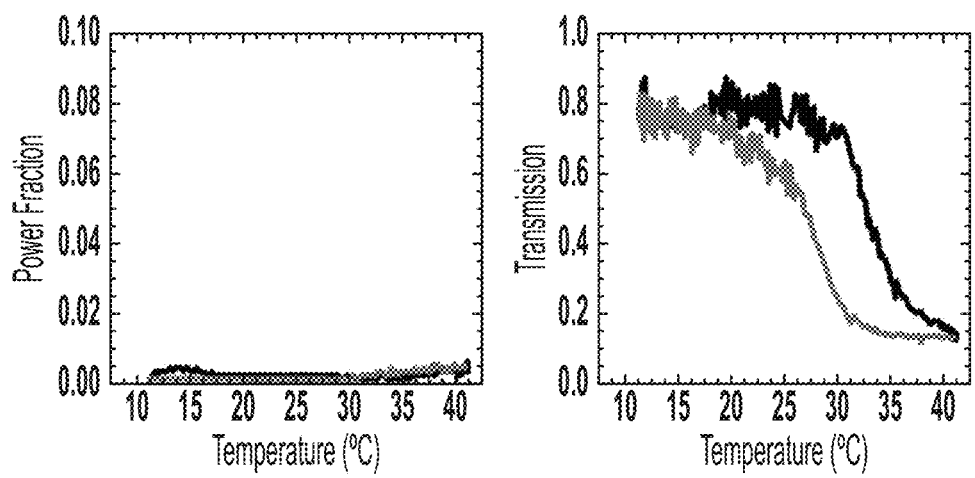
Figure 15C:
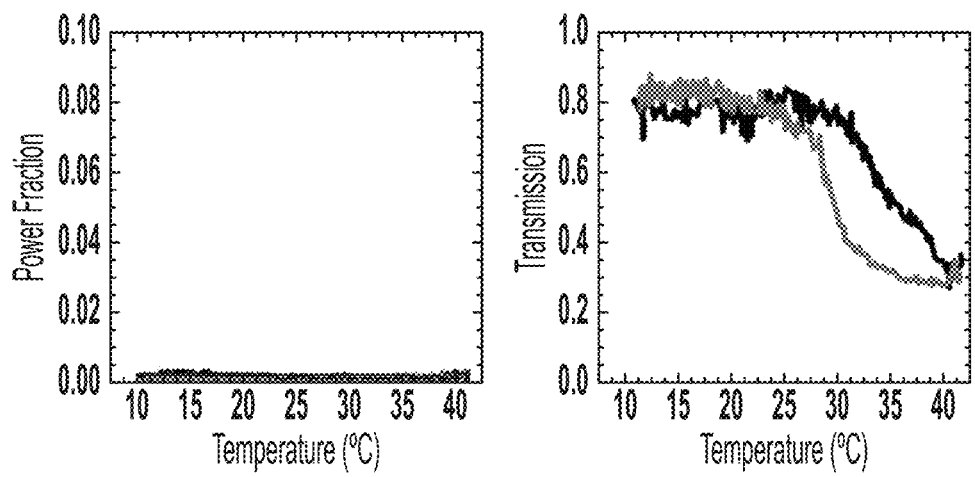
Figure 15D:
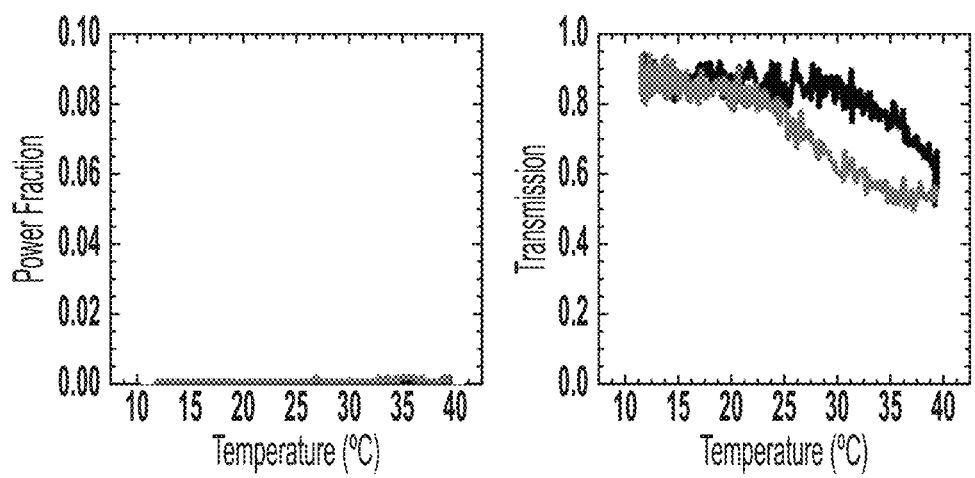
Figure 15E:
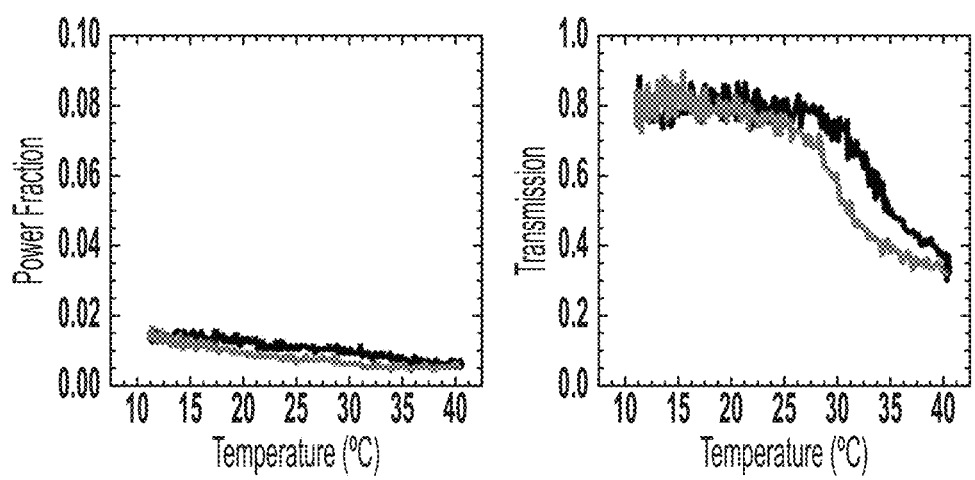
Figure 15F:
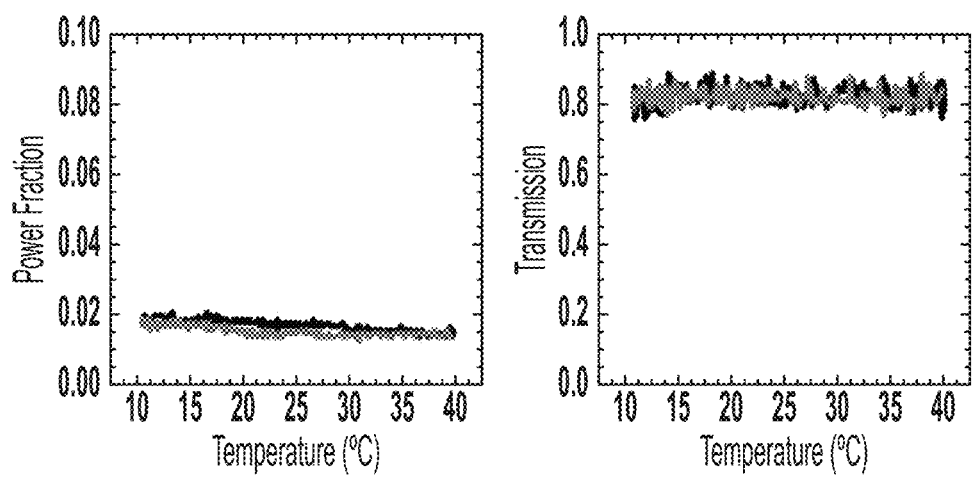
Figure 15G:
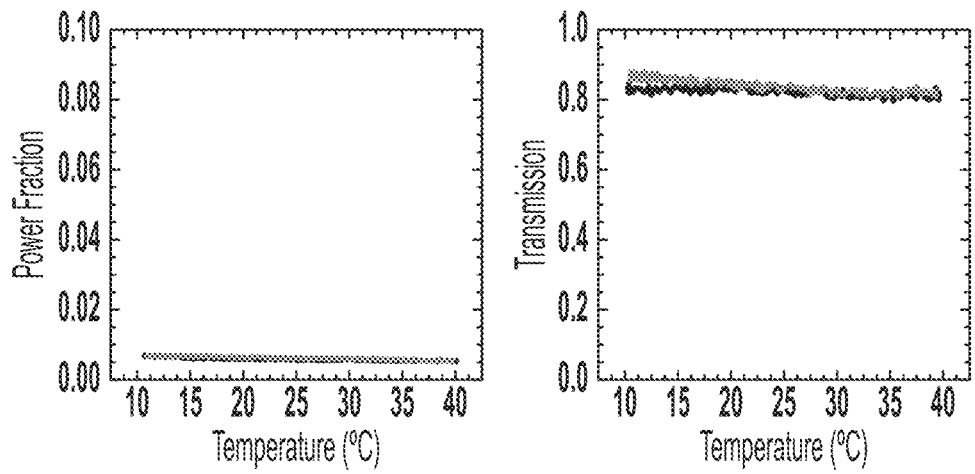
Figure 15H:
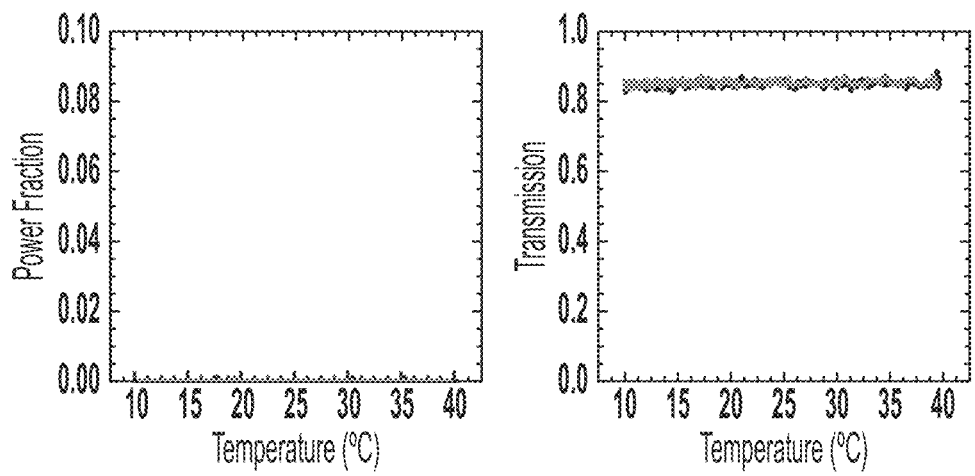
Figure 16A:
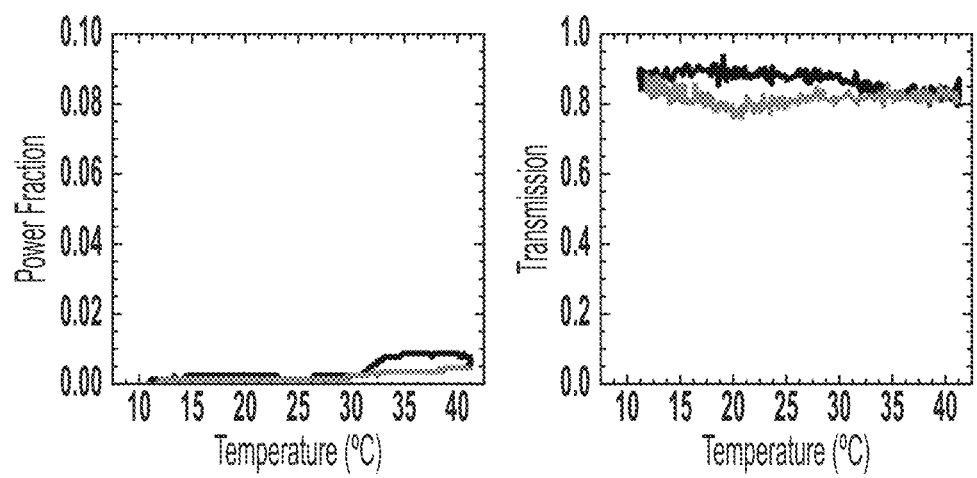
FIGS. 16A-16H. DPLS and turbidimetry heating/cooling cycles for 2×SP17k at (FIG. 16A) 30 wt. %, (FIG. 16B) 35 wt. %, (FIG. 16C) 40 wt. %, (FIG. 16D) 45 wt. %, (FIG. 16E) 50 wt. %, and (FIG. 16F) 60 wt. %, (FIG. 16G) 70 wt. % and (FIG. 16H) 100 wt. %. The curves represent the heating cycle, the cooling cycle, and the 10-minute equilibration at the end of the heating cycle before cooling.
Figure 16B:
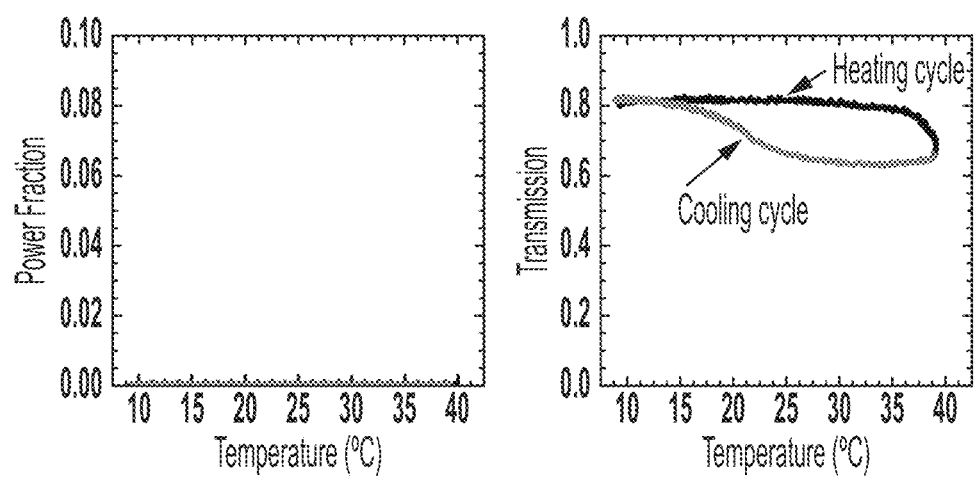
Figure 16C:
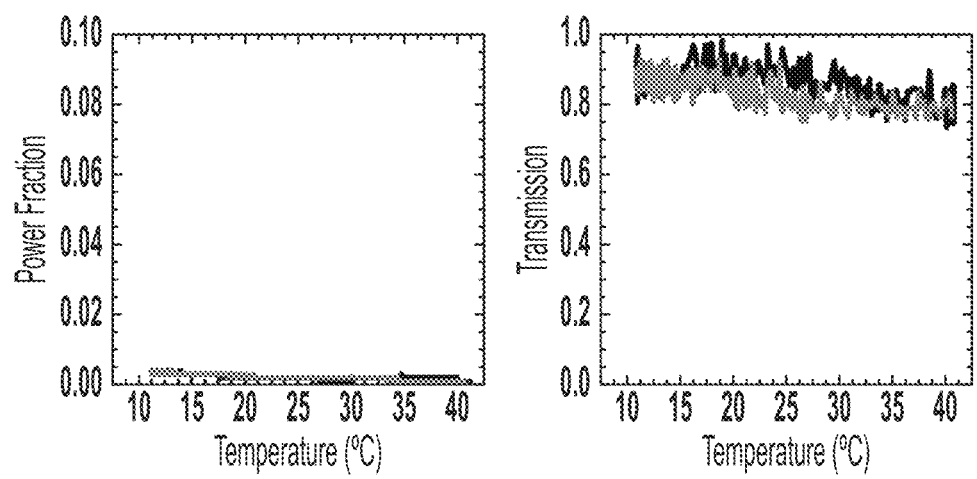
Figure 16D:
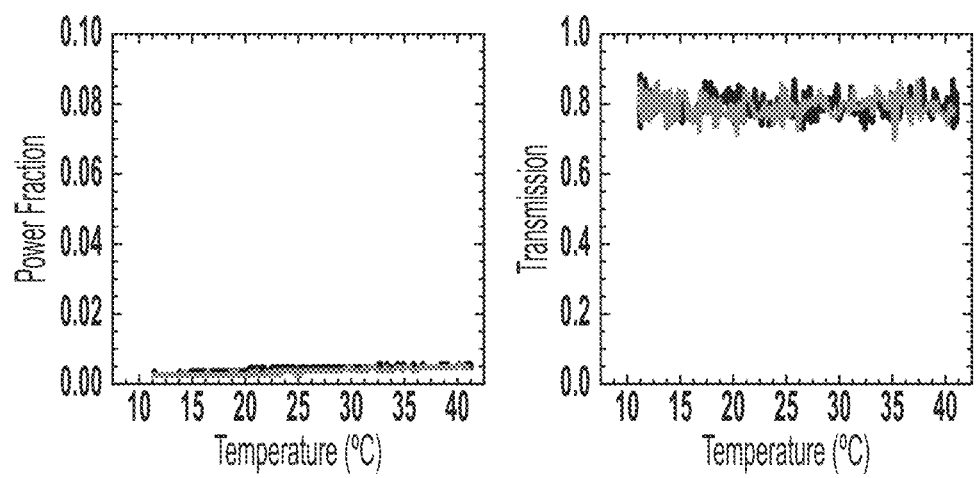
Figure 16E:
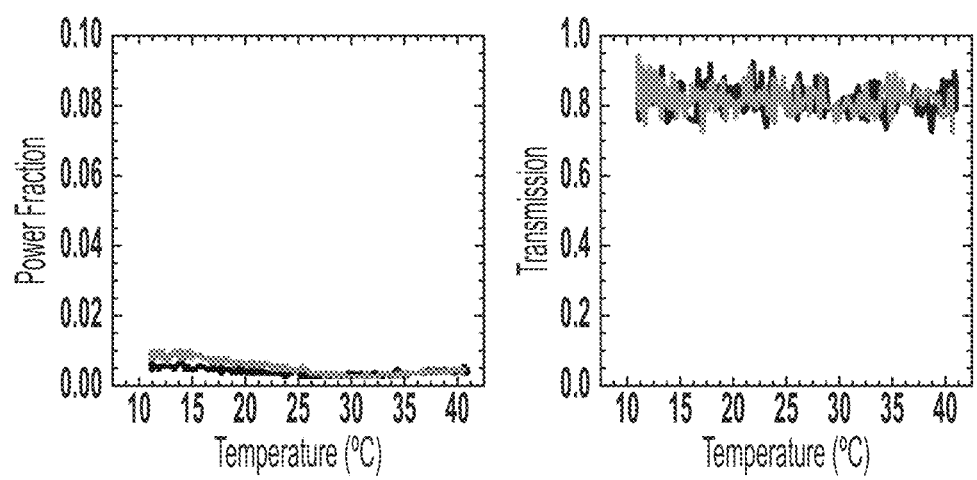
Figure 16F:
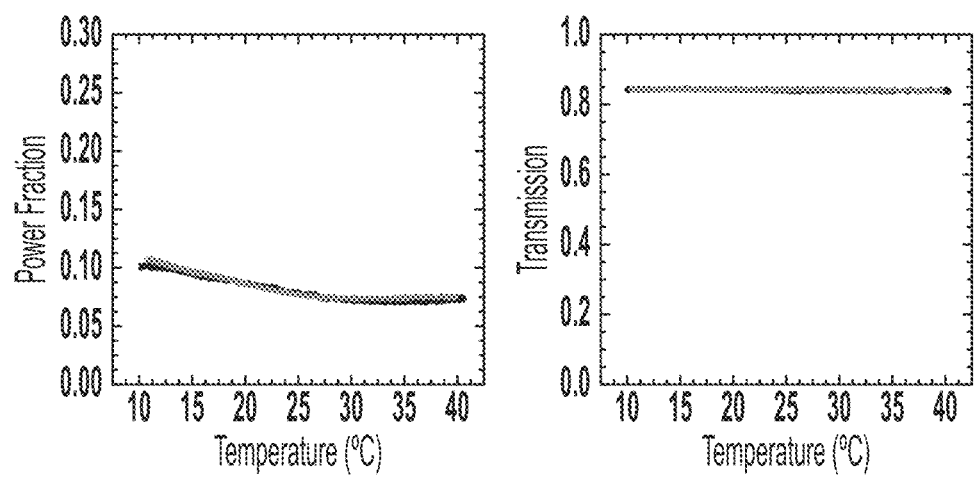
Figure 16G:
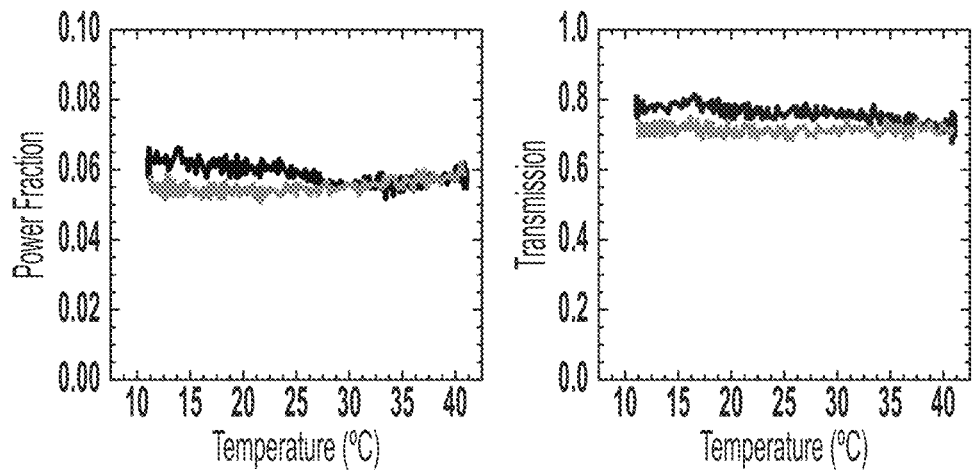
Figure 16H:
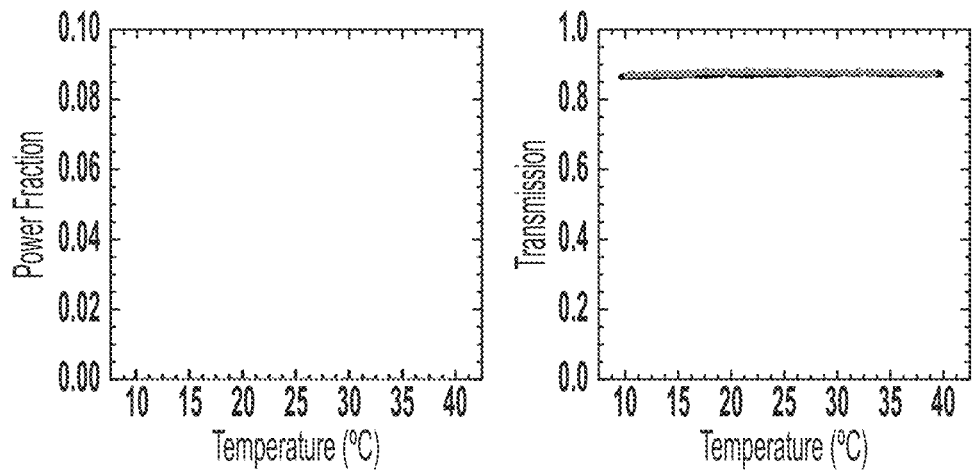
Figure 17A:
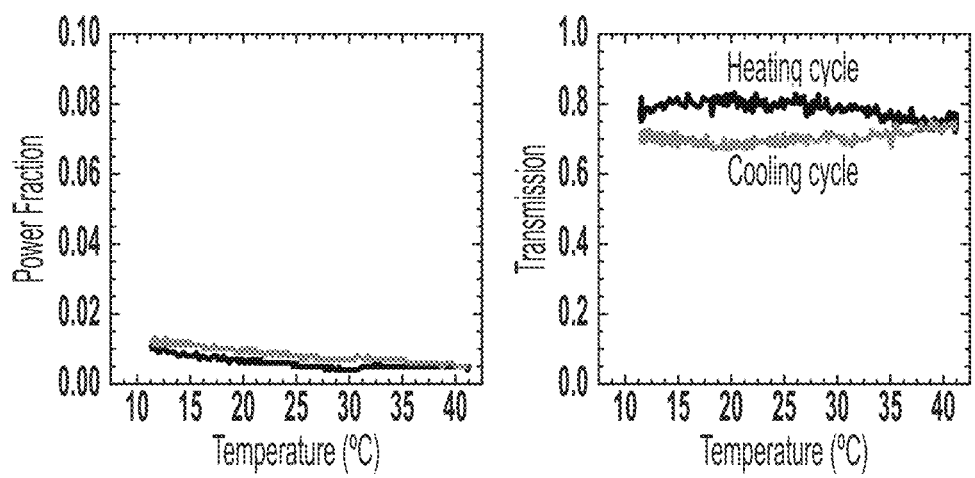
FIGS. 17A-17H. DPLS and turbidimetry heating/cooling cycles for 3×SP25k at (FIG. 17A) 30 wt. %, (FIG. 17B) 35 wt. %, (FIG. 17C) 40 wt. %, (FIG. 17D) 45 wt. %, (FIG. 17E) 50 wt. %, (FIG. 17F) 60 wt. %, (FIG. 17G) 70 wt. % and (FIG. 17H) 100 wt. %. The curves represent the heating cycle, the cooling cycle, and the 10-minute equilibration at the end of the heating cycle before cooling.
Figure 17B:
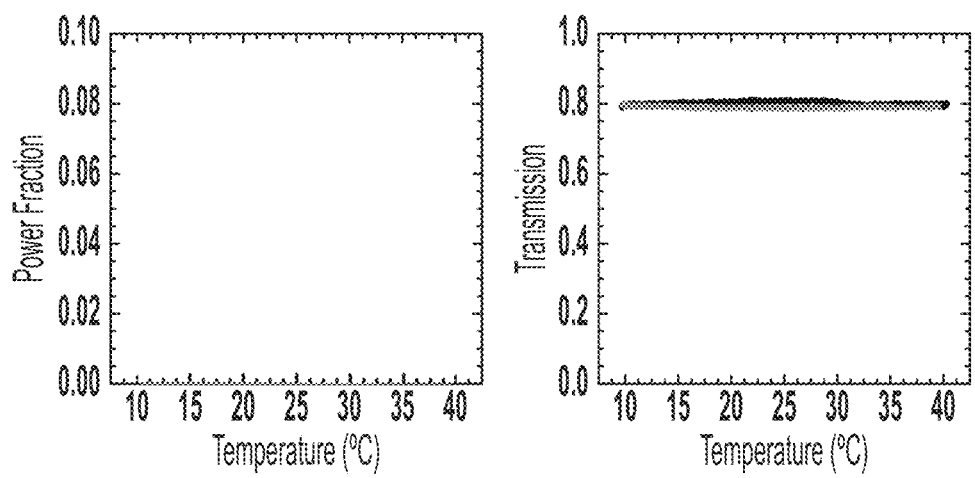
Figure 17C:
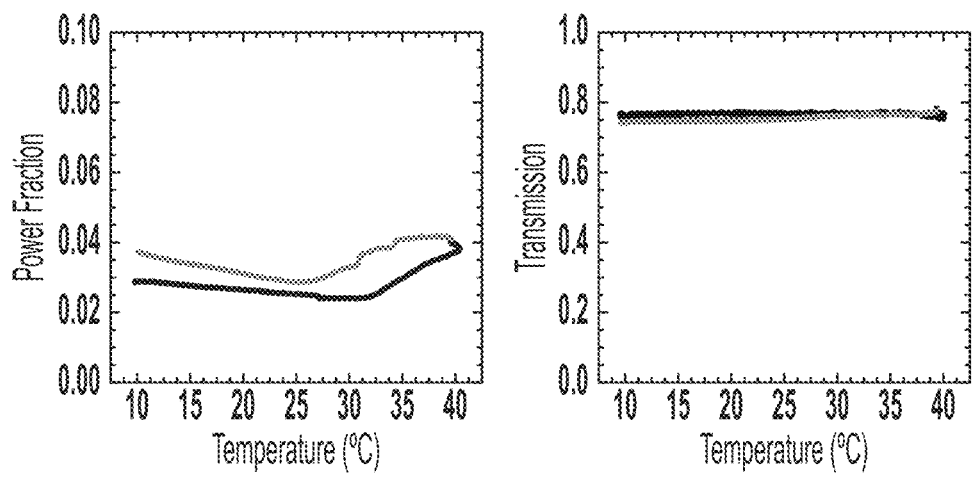
Figure 17D:
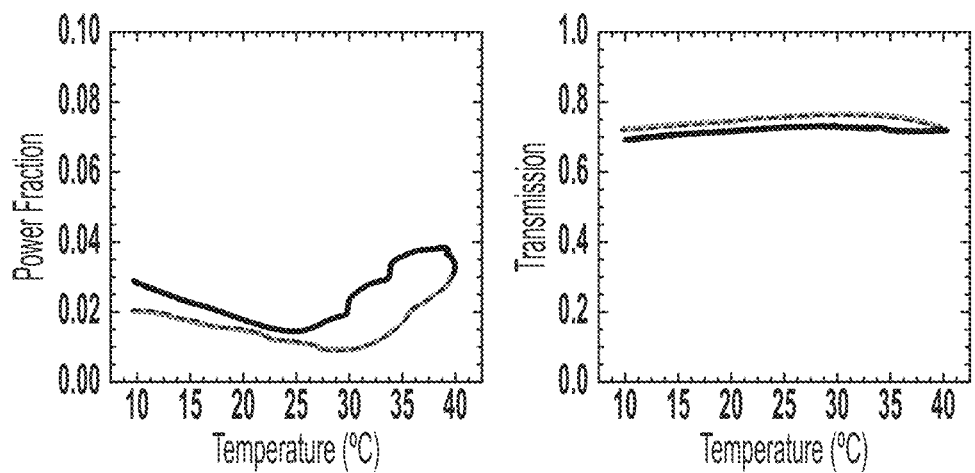
Figure 17E:
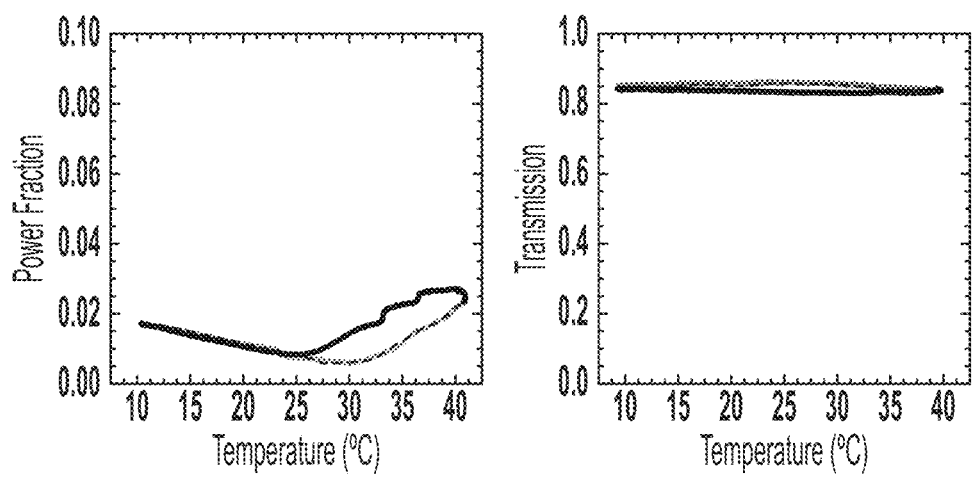
Figure 17F:
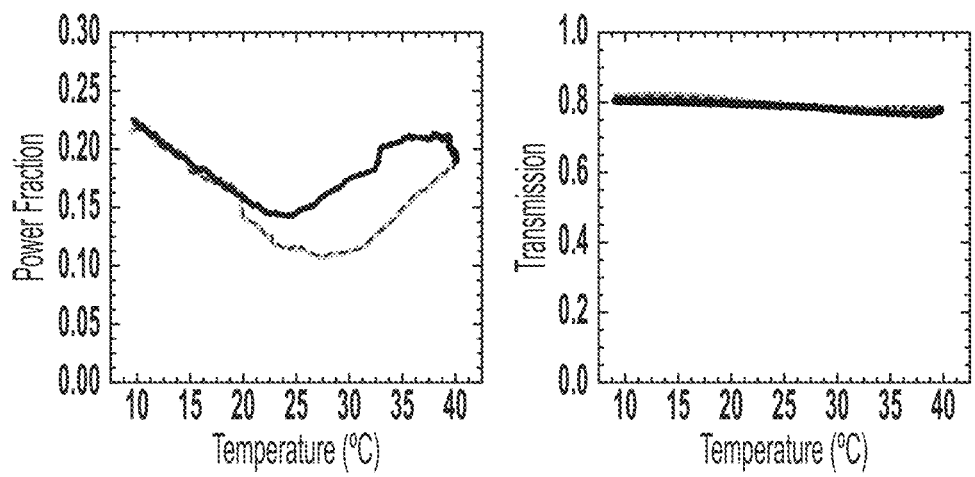
Figure 17G:
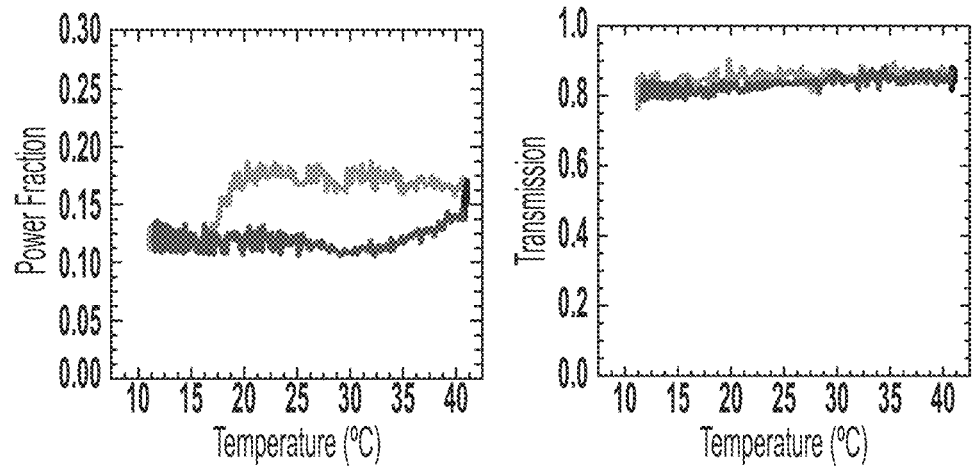
Figure 17H:
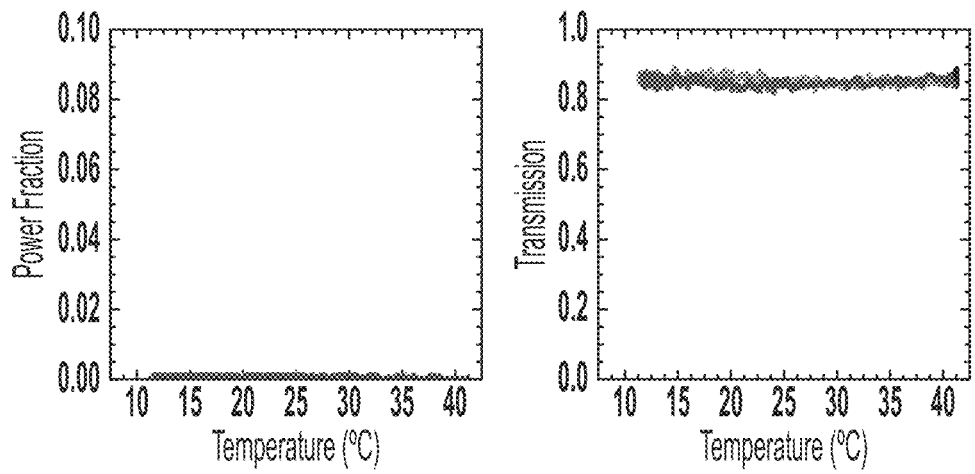
Figure 18A:
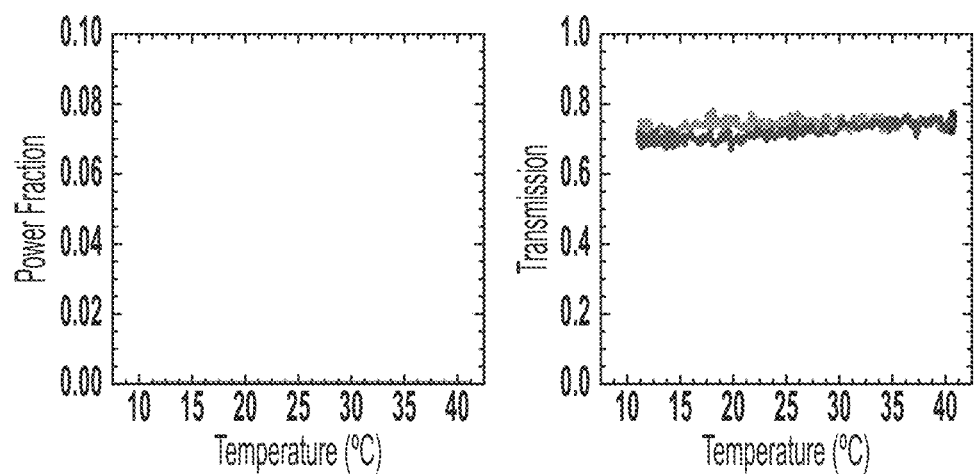
FIGS. 18A-18H. DPLS and turbidimetry heating/cooling cycles for 4×SP30k at (FIG. 18A) 30 wt. %, (FIG. 18B) 35 wt. %, (FIG. 18C) 40 wt. %, (FIG. 18D) 45 wt. %, (FIG. 18E) 50 wt. %, and (FIG. 18F) 60 wt. %, (FIG. 18G) 70 wt. % and (FIG. 18H) 100 wt. %. The curves represent the heating cycle, the cooling cycle, and the 10-minute equilibration at the end of the heating cycle before cooling.
Figure 18B:
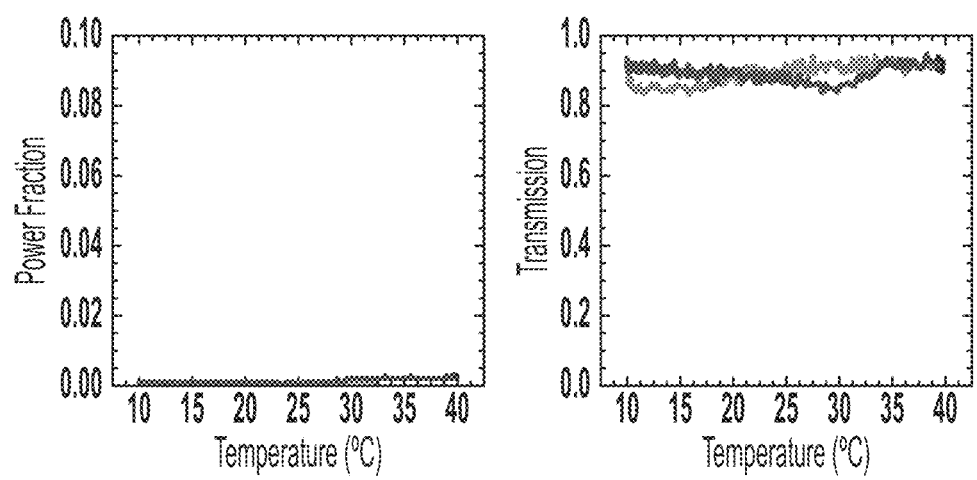
Figure 18C:
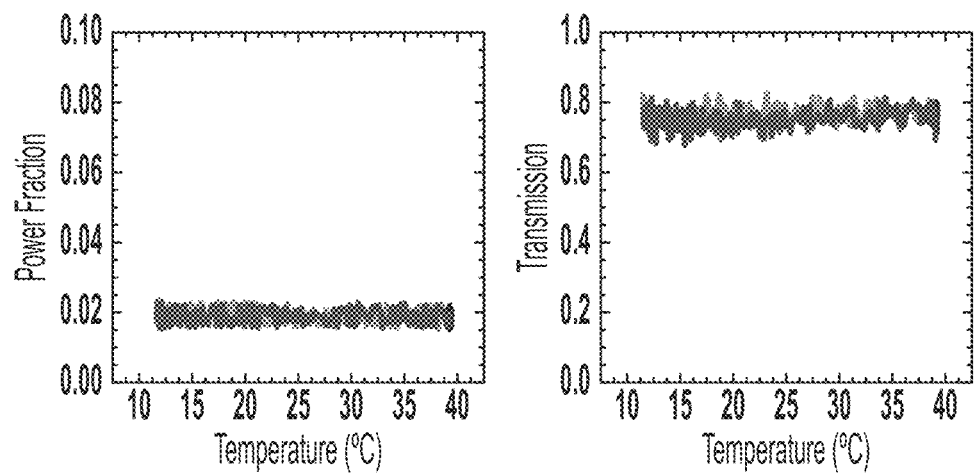
Figure 18D:
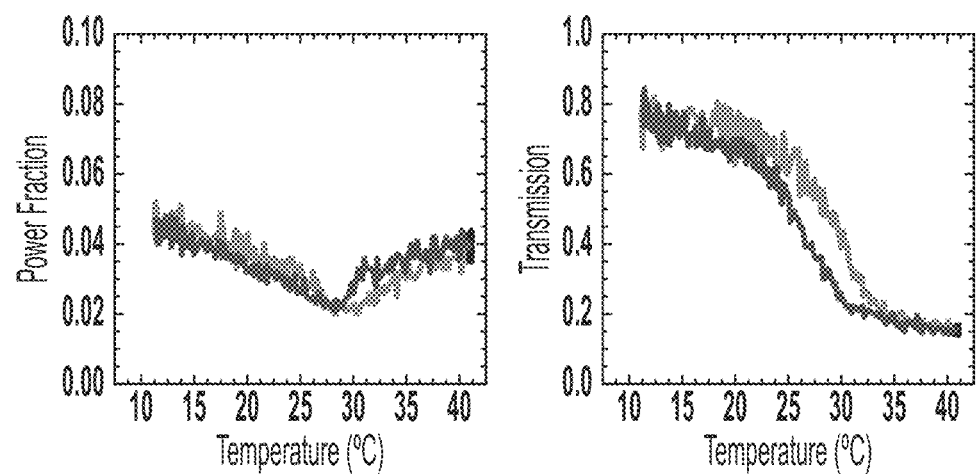
Figure 18E:
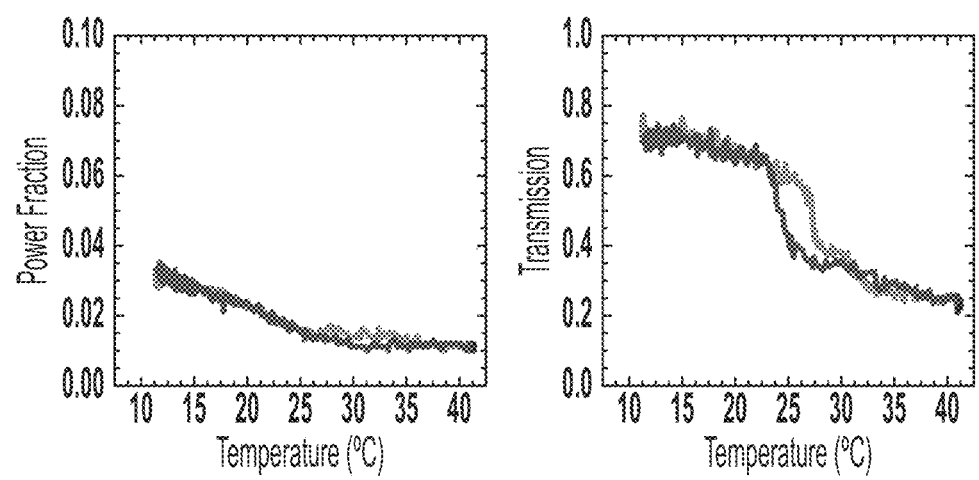
Figure 18F:
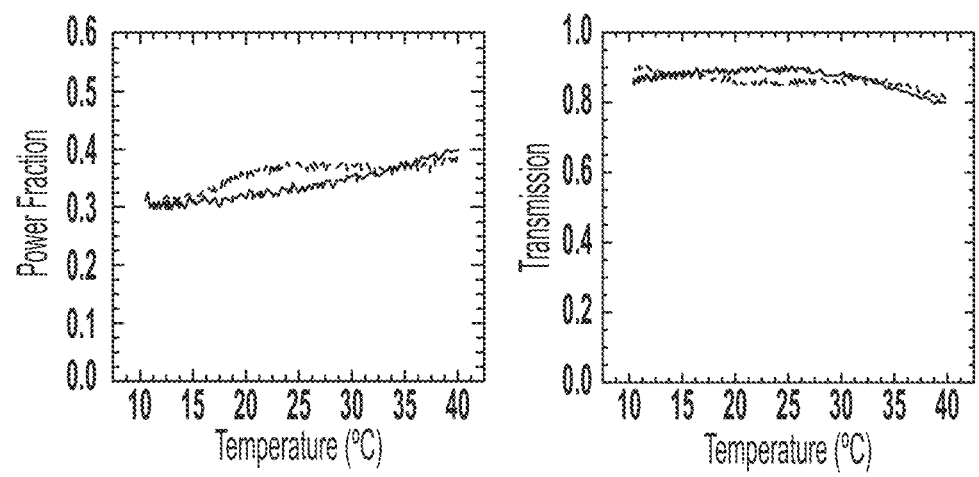
Figure 18G:
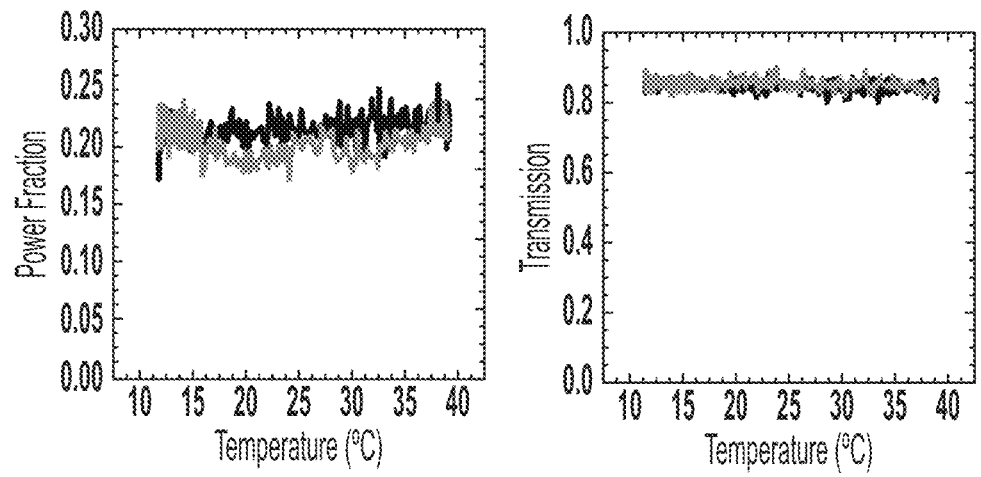
Figure 18H:
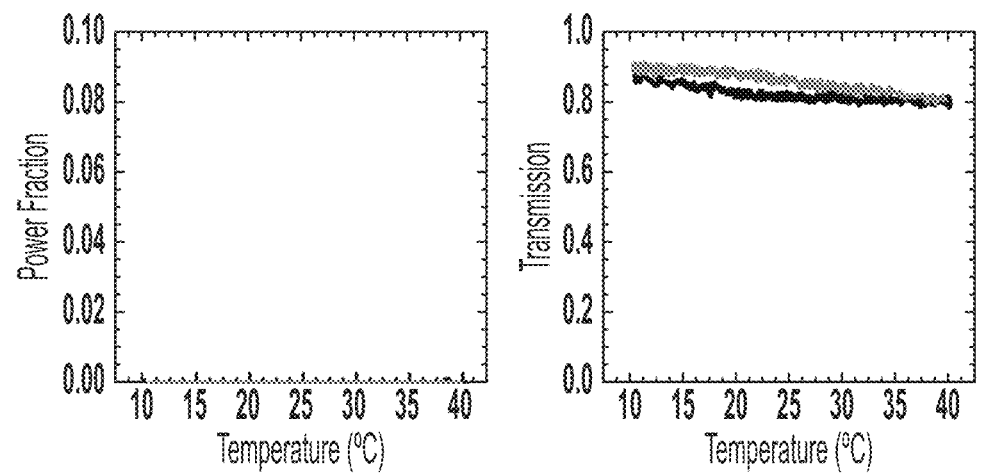
Figure 19A:
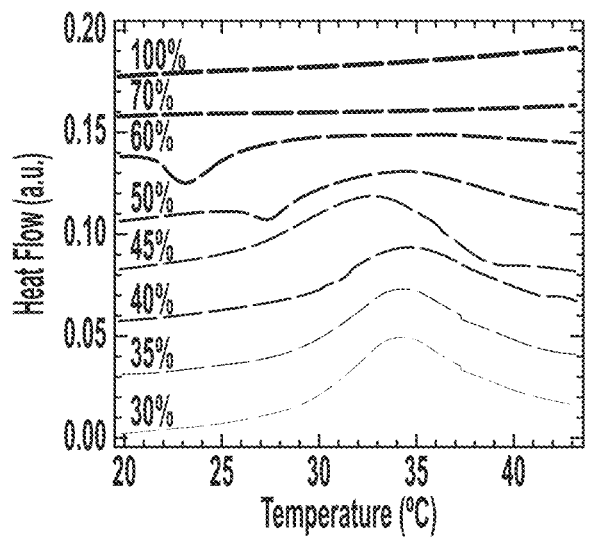
FIGS. 19A-19D. DSC curves of (FIG. 19A) 1×SP9.8k, (FIG. 19B) 2×SP17k, (FIG. 19C) 3×SP25k, and (FIG. 19D) 4×SP30k at varying concentrations. Curves are offset for clarity.
Figure 19B:
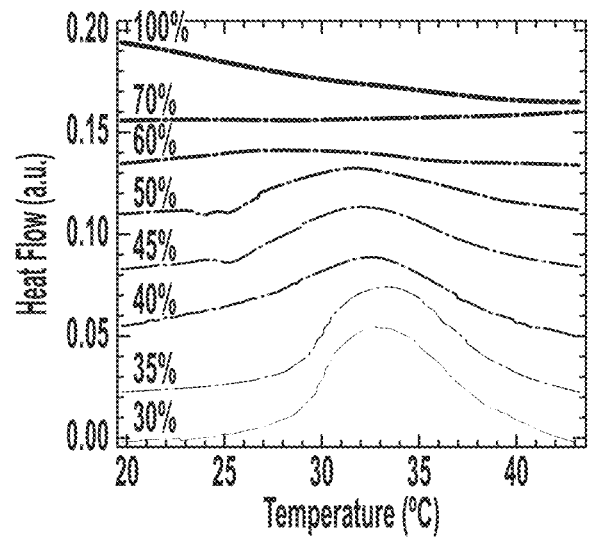
Figure 19C:
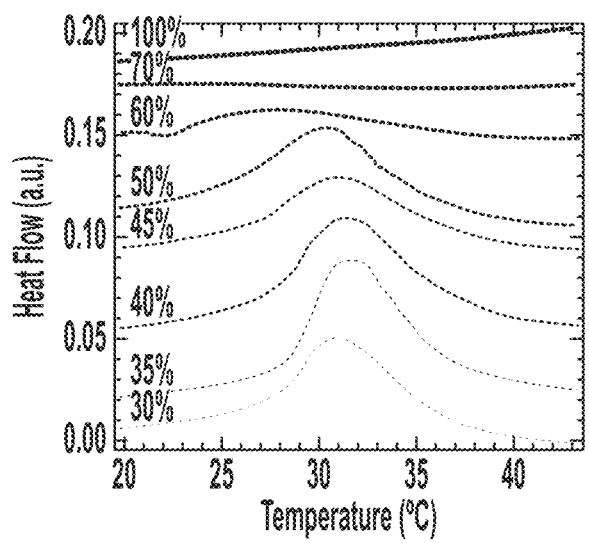
Figure 19D:
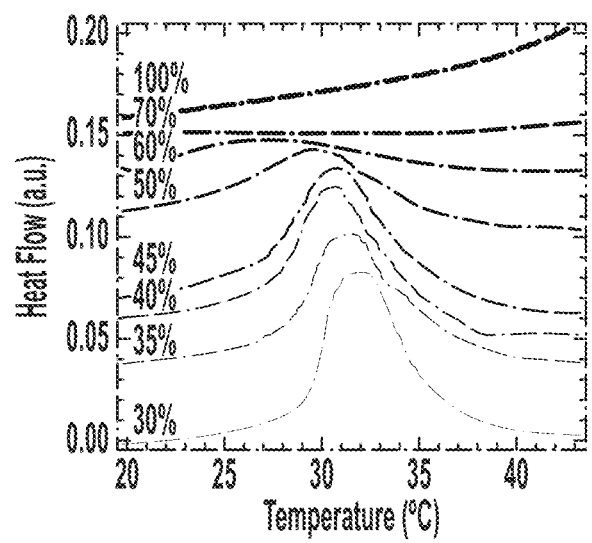

Details for the construction of genes for monomeric, dimeric, trimeric, and tetrameric rcSso7d.SA each containing an N-terminal Cys residue are provided below. Each gene was inserted into a pET28b(+) vector, which encodes an N-terminal 6×His tag, and transformed into BL21(de3) *E. coli* cells. Each protein was expressed in 1 L of Terrific Broth at 37° C. inoculated with 5 mL of overnight culture and induced with 1 mM isopropyl-β-D-1-thiogalactopyranoside (IPTG) at an $OD_{600}$ of 0.8-1.0. After induction the cells were cultured at 20° C. for 18-20 hours and harvested. The cells were resuspended in lysis buffer (50 mM $NaH_2PO_4$, 300 mM NaCl, 10 mM imidazole, 10 mM β-mercaptoethanol (BME), pH 8.0) and frozen at −80° C. overnight. After thawing, the cells were lysed by ultrasonication. The lysate was clarified by centrifugation, and the protein was purified using Ni-NTA metal affinity chromatography. Throughout the purification, 10 mM BME was used in all buffers. Elution fractions containing purified protein were immediately exchanged into resuspension buffer (50 mM Tris buffer, 100 mM NaCl, 0.25 mM tris(2-carboxyethyl)phosphine (TCEP), pH 7.4) by performing a 1000× buffer exchange in Millipore-Ultra 15 centrifugal filters (molecular weight cutoff of 3 kDa for monomeric rcSSo7d.SA or 10 kDa for rcSso7d.SA oligomers). The purity of the protein was confirmed by denaturing gel electrophoresis (SDS-PAGE) (FIG. 9A). Protein concentration was determined by performing a reducing-agent compatible BCA assay, and proper secondary structure folding of the proteins was assessed using circular dichroism (CD) (FIG. 10A). The typical yields of purified protein for the monomeric, dimeric, trimeric, and tetrameric rcSso7d.SA species were 120, 160, 75, and 40 mg per liter of culture, respectively.

Bioconjugation and Preparation of Bulk Samples.

Figure 9B:
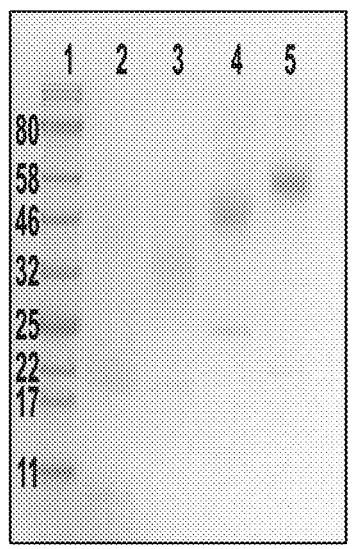
Figure 9C:
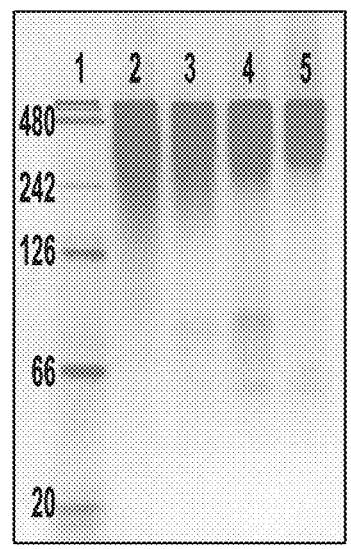

Bioconjugations between rcSso7d.SA oligomers and maleimide-functionalized PNIPAM were performed in resuspension buffer. Solutions of rcSso7d.SA oligomers were diluted to approximately 5 mg/mL, and a 5× molar excess of PNIPAM was added. After complete dissolution of PNIPAM, samples were incubated at 4° C. for 24 h. Ammonium sulfate was then added to a concentration of 1.0 M to remove unconjugated protein. Following centrifugation, the supernatant was discarded and the precipitates were resuspended in resuspension buffer to approximately 5 mg/mL. Two additional ammonium sulfate precipitations were performed, after which the resulting solution was purified by Ni-NTA chromatography to remove unconjugated PNIPAM. Purified protein-PNIPAM conjugates were dialyzed against MilliQ water. Bioconjugate purity was confirmed using SDS-PAGE and Native PAGE (FIGS. 9B, 9C), and retention of protein secondary structure was assessed using CD (FIG. 10B). Conjugate solution was concentrated to approximately 100 mg/mL using Millipore-Ultra 15 centrifugal filters (molecular weight cutoff of 10 kDa). Bulk solid samples were prepared by drop-casting aliquots of this concentrated solution onto Teflon sheets and drying under vacuum to a final pressure of 5 Torr (ramp rate 50 Torr/h) at room temperature. Samples were then collected and stored at 4° C. until future use. Typical yields after purification ranged from 50% with monomeric rcSso7d.SA to 25% with tetrameric rcSso7d.SA.

Solution-Phase Sample Preparation and Characterization.

Dehydrated samples were rehydrated in MilliQ water at 4° C. to the desired concentration immediately prior to use. The concentrated solution phase behavior of rcSso7d.SA-PNIPAM conjugates was characterized using small-angle X-ray scattering (SAXS) (FIGS. 11-14), depolarized light scattering (DPLS) and turbidimetry (FIGS. 15-18-S16), and differential scanning calorimetry (DSC) (FIG. 19). Details of the sample preparation and measurement conditions for these techniques are provided below.

Thin Film Preparation.

Silicon wafers (Wafer World, P-type Silicon with boron as dopant, (100) orientation, single-side polished) were cut into 0.9 cm-by-5 cm sections and sequentially and thoroughly rinsed with acetone, methanol, and water. Wafers were then dried under a filtered air flow and treated with oxygen plasma for 3 minutes. Immediately following plasma cleaning, conjugate samples rehydrated to 10 wt. % in MilliQ water were flow coated onto the silicon wafers in a chamber maintained at 60% relative humidity, as described previously.[60] To stabilize thin films against dissolution in water, the cast films were preheated to 40° C. and immersed in a 1.4 wt. % aqueous solution of glutaraldehyde at 40° C. for 20 s to lightly crosslink the protein nanodomains. Immediately following immersion, thin films were thoroughly rinsed with water until the surfaces became hydrophilic, indicating complete removal of unlinked glutaraldehyde. Films were dried under filtered airflow and stored at ambient conditions until use. Film thickness was determined using a Woolam M-2000D spectroscopic ellipsometer using a single incidence angle of 70°. Curves were fit using a three-layer model consisting of a 0.4 mm bottom silicon substrate, a native silicon oxide layer of 18 Å, and a top conjugate layer fit using a Cauchy model. rcSso7d.SA monolayers were prepared by coupling protein activated by 1-Ethyl-3-(3-dimethylaminopropyl)carbodiimide/N-hydroxysuccinimide (EDC/NHS) with amine-functionalized silicon wafers using literature methods.[60-61]

Fluorescent Assays.

Figure 33:
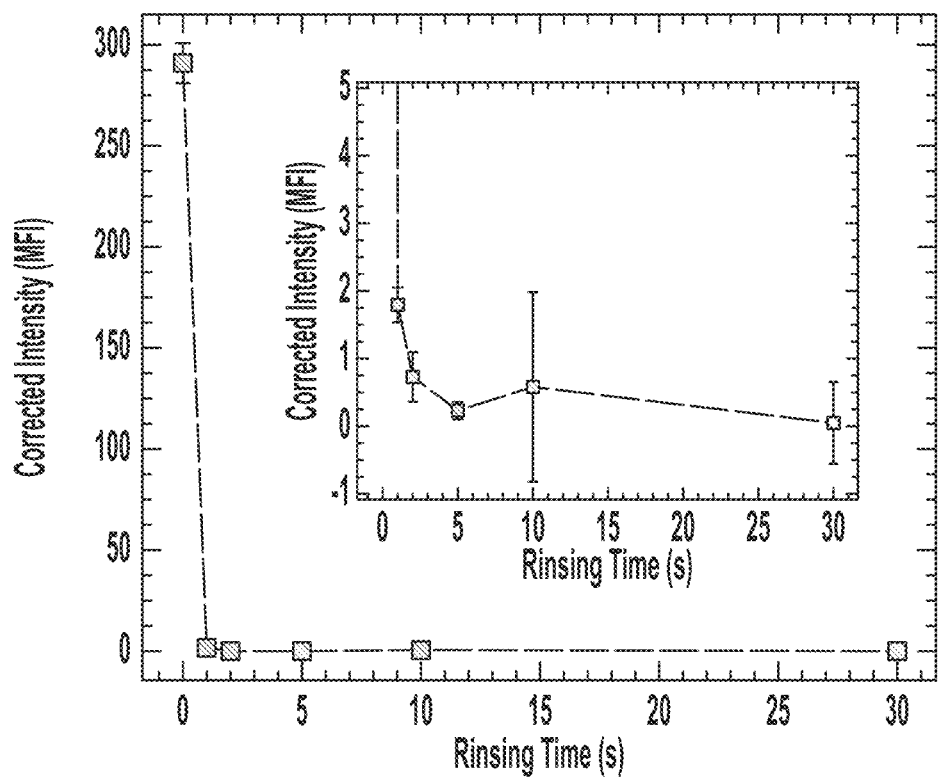
FIG. 33. Fluorescent intensity of BSA labeled with Alexa Fluor 488 retained in 3×SP77.6k thin film after various rinsing times. Inset shows enlarged view of low intensity data. The film was 144 nm thick and exposed to a 10 µM solution of BSA. Error bars represent the standard deviation of three replicates.

The binding function of rcSso7d.SA oligomer-PNIPAM thin films was measured using fluorescently-labeled monomeric streptavidin (mSA2) and fluorescently-labeled streptavidin (SA). Details for the expression, purification, and fluorescent labeling of mSA2 are provided below. Samples were prepared by serial dilution of SA or mSA2 in PBS (pH 7.4), human urine (diluted to 50% v/v in PBS, pH 7.4), or blood serum (obtained as the supernatant by centrifuging whole blood at 1500×g for 10 minutes, then diluted to 50% v/v in PBS, pH 7.4). 0.5 μL drops of solutions containing serially diluted fluorescent mSA2 and fluorescent SA samples in PBS (pH 7.4) were gently applied to the surface of each bioconjugate thin film. Films were incubated in a sealed chamber saturated with water vapor at room temperature to prevent to prevent drying of the applied fluorescent samples. After 1 hour, films were thoroughly rinsed with water for 10 seconds (a time determined to be sufficient to remove unbound molecules from the film, see FIG. 33, dried under filtered airflow, and immediately analyzed for fluorescent signal. Fluorescence microscopy images were acquired at 4× magnification using a Cy5 filter set and exposure time of 5000 ms on an Olympus IX-81 inverted fluorescence microscope with an AxioCam HRC CCD camera. Fluorescent intensity was calculated using ImageJ software[67] by determining the average fluorescent signal in a rectangular area of the fluorescent image free of defects and occupying no less than half of the full sample application area.

Gene Construction

Figure 7B:
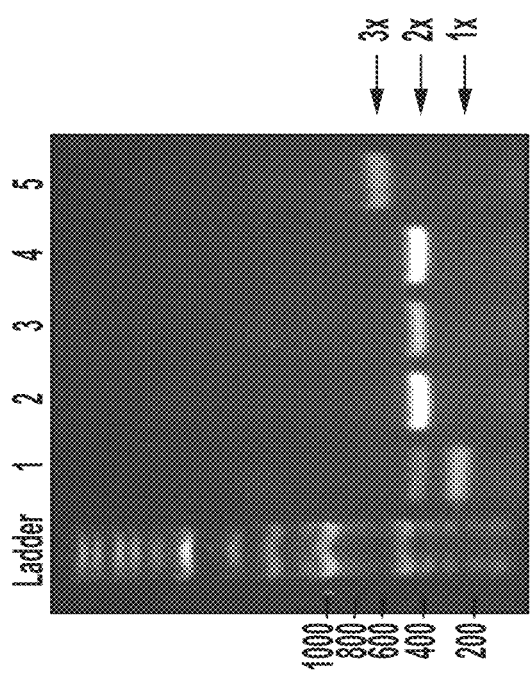
FIGS. 7A-7B.
Figure 7A:
Figure 7A:
Figure 7A:
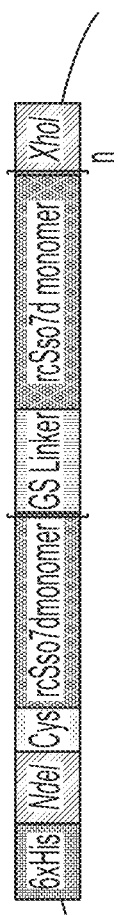

Genetic constructs encoding the rcSso7d oligomers were produced via Golden Gate assembly, using the Type IIS restriction endonuclease BsaI to create a diverse library of scarless oligomers in a single reaction (FIG. 7A). An acceptor plasmid was first generated by appending a pair of opposing BsaI sites with unique overhang motifs to the 3' side of the monomeric rcSso7d.SA gene. This was done via standard PCR, conducted using the N-Cys-rcSso-for and rcSso-Mult-Acc-rev primers (Table 1) at an annealing temperature of 59.2° C. This construct was then integrated into a pET28b(+) vector via an NdeI/XhoI double digest and overnight ligation, as previously described.[39]

TABLE 1

Oligonucleotide Sequences of Primers Used in Oligomer Generation

| Oligo Name | DNA Sequence, 5'-3' (NdeI, XhoI, and BsaI sites) | SEQ ID NO | Annealing Temperature (° C.) |
| --- | --- | --- | --- |
| N-Cys rcSso7d-for | AGGCAGTCT<u>CATATG</u>TGTGCAACCGTGAAAT TCAC | 24 | 64.2 |
| rcSso-Mult-Acc-rev | ATTGAC<u>CTCGAG</u>TTATCCACCCGAGACCACT GGGTCTCACACCTTGCTTTTCCAGCATCT | 25 | 71.7 |
| rcSso-Mult-Ins-for | ATTTAAGGTCTCCGGTGGTGGTGGTAGCGG TGGTGGCGGTTCAATGGCAACCGTGAAATT | 26 | 73.2 |
| rcSso-Mult-Ins-rev | ATTTAAGGTCTCACACCTTGCTTTTCCAGCA TCTGCAGC | 27 | 66 |
| T7-for | TAATACGACTCACTATAGGG | 28 | 47.5 |
| T7-rev | GCTAGTTATTGCTCAGCGG | 29 | 53.4 |

In a separate reaction, an insertion product was produced by modifying the rcSso7d.SA gene with a 5'-(G4S)$_2$ (SEQ ID NO: 40) flexible linker sequence. BsaI sites with cleavage overhangs complementary to those in the acceptor plasmid were appended on either end of the insertion product. PCR was conducted using the rcSso-Mult-Ins-for and rcSso-Mult-Ins-rev primers at an annealing temperature of 61° C. Following preparative-scale 1% agarose gel electrophoresis and gel extraction, each of these constructs was incubated for one hour at 37° C. in a separate BsaI restriction digest reaction, followed by an hour-long incubation with Antarctic phosphatase and a ten-minute 65° C. hold for enzymatic inactivation. The products were once again gel-purified and extracted, and a 20 ligation reaction was prepared using 40 ng of digested acceptor plasmid, with the digested insertion product comprising the remainder of the available reaction volume. This ligation reaction was incubated overnight at 16° C., and was purified using a Zymoprep Clean and Concentrator kit. Purified ligation product was eluted in 12 µL of molecular-grade water, and 4 µL of this ligation mixture was transformed into DH5a E. coli.

To screen the resultant library of clones for the desired oligomer products, selected colonies were subjected to colony PCR. Flanking primers were used rather than rcSso7d-specific primers, because rcSso7d-specific primers would primarily yield monomeric product bands, regardless of the actual degree of oligomerization. Individual colonies were re-suspended in 50 µL of molecular-grade water, and 1 µL of each cell suspension was taken for the PCR mixture. Each PCR mix also contained 2 µL of 5× Phusion HF polymerase buffer, 0.25 µL of dNTP mix (10 mM of each base), 0.6 µL each of the T7-for and T7-rev primers at a concentration of 10 µM, 0.2 µL of Phusion HF polymerase, and 5.35 µL of molecular-grade water, for a final reaction volume of 10 µL. The thermocycling profile featured an initial denaturation at 95° C. for 6 minutes, followed by 35 cycles of (i) denaturation at 95° C. for 30 seconds, (ii) primer annealing at 41° C. for 30 seconds, and (iii) extension at 72° C. for 30 seconds, with a final extension step at 72° C. for 10 minutes. Following PCR, the reaction mixtures were visualized via analytical-scale 1% agarose gel electrophoresis (FIG. 7B). Colonies corresponding to PCR products at the predicted amplicon lengths were sequence-verified using the T7-for and T7-rev sequencing primers.

Sample Preparation and Characterization

Small-angle X-ray scattering (SAXS) samples were loaded into 1 mm thick aluminum washers and sealed with Kapton tape. After loading, samples were incubated at 37° C. for 10 minutes to remove any effects of shear alignment when loading the samples. All bioconjugates were measured at the National Synchrotron Light Source II (NSLS-II) at Beamline 11-BM. Samples were equilibrated for 10 minutes at each measured temperature prior to data collection. SAXS data were corrected for empty cell and dark field scattering, and acquisition times were minimized to prevent beam damage. All observed transitions were reversible with temperature.

GISAXS experiments were conducted at beamline 8-ID-E at Argonne National Laboratory using X-rays with energy 10.915 keV. Samples were measured at incident angles of 0.105° for analysis of surface morphology and 0.140° for bulk morphology. All measurements for a given sample were collected at the same position on the film, which was exposed to X-rays for a time totaling no more than 30 seconds to prevent beam damage. Films were loaded into a sealed chamber and exposed to room temperature air at 95% relative humidity (RH). Film thickness was continuously measured using a Filmetrics F20-UV thin film analyzer. GISAXS measurements of swollen films were collected after 15 minutes of exposure to 95% RH air, at which time the air within the chamber had reached 95% RH and the film thickness had stabilized.

Turbidimetry and depolarized light scattering (DPLS)[64-65] were performed on samples loaded into a 1 mm thick Teflon mold and sealed between two quartz disks. After loading, samples were incubated at 37° C. for 10 minutes to remove any effects of shear alignment when loading the samples. A Coherent OBIS LX660 laser was used with wavelength λ=662 nm and continuous wave output power 10 mW. Samples were equilibrated at 10° C. for 10 minutes and then heated at 1° C./min. to 40° C., allowed to equilibrate for 10 minutes, and then cooled at 1° C./min. to 10° C. The static depolarized light scattering signal was corrected for transmission and dark field background. For turbidimetry measurements, the same apparatus was used without the rear polarizer to enable measurement of sample transmission. Macrophase separation transitions were defined as the temperatures $T_t$ corresponding to a 10% reduction in the initial sample transmittance, according to literature methods.[66] Transitions were reproducible for at least 5 repeated heating/cooling cycles, and data analysis was performed on the first heating cycle.

Differential scanning calorimetry (DSC) samples were loaded into a hermetically sealed aluminum pan. Data were acquired using a TA Instruments Discovery differential scanning calorimeter at the Institute for Soldier Nanotechnologies (ISN) at MIT. Each sample was equilibrated at 5° C. for 5 minutes, followed by two cycles of ramping to 45° C. at 5° C./min., holding isothermally for 2 minutes, cooling at 5° C./min to 5° C., and holding isothermally for 2 minutes. Both measurement cycles were found to overlap for all conjugates, and temperature transition values were extracted from the onset point in the initial heating cycle.

Circular dichroism (CD) spectroscopy was performed using a JASCO Model J-1500 CD spectrometer to measure far UV CD spectroscopy between 195 and 250 nm in a 0.1 cm path length quartz cuvette. All unconjugated proteins were measured in 50 mM Tris buffer, 100 mM NaCl, 0.25 mM TCEP, pH 7.4. All conjugates were measured in MilliQ water. Measurements were collected at 25° C.

Expression, Purification, and Fluorescent Labeling of mSA2

The gene for mSA2 containing a C-terminal FLAG tag and N-terminal 6×His and MBP tags separated from the mSA2 sequence by a TEV protease recognition site, pET-MBP-mSA2, was a gift from Sheldon Park (Addgene plasmid #52319). Prior to expression, the plasmid was transformed into BL21(de3) *E. coli* cells. The protein was expressed in 1 L of Terrific Broth at 37° C. inoculated with 5 mL of overnight culture and induced with 1 mM isopropyl-β-D-1-thiogalactopyranoside (IPTG) at an $OD_{600}$ of 0.8-1.0. After induction the cells were cultured at 20° C. for 18-20 hours and harvested. The cells were resuspended in lysis buffer (50 mM $NaH_2PO_4$, 300 mM NaCl, 10 mM imidazole, 10 mM β-mercaptoethanol (BME), pH 8.0) and frozen at −80° C. overnight. After thawing, the cells were lysed by ultrasonication. The lysate was clarified by centrifugation, and the protein was purified using Ni-NTA metal affinity chromatography. Throughout the purification, 10 mM BME was used in all buffers. Elution fractions containing purified mSA2 with an MBP solubility tag were dialyzed against 50 mM Tris buffer (pH 8.5). The N-terminal 6×His and MBP tags were cleaved using AcTEV protease (Invitrogen) by incubating at 20° C. for 48 hours. The cleavage mixture was incubated with Ni-NTA at 4° C. overnight, after which the mixture was loaded into a column, and the filtrate was collected. The resin was rinsed with 15 column volumes of wash buffer (50 mM Tris buffer, 300 mM NaCl, 10 mM imidazole, 10 mM BME, pH 7.4). The elution fractions were combined with the initial filtrate and dialyzed against 20 mM Tris buffer (pH 7.2) and subsequently purified using a HiTrap Q HP anion exchange chromatography column (GE Healthcare). Fractions containing pure mSA2 were combined, dialyzed against PBS (pH 7.4), and stored at 4° C. until further use.

mSA2 in PBS was concentrated to approximately 2 mg/mL. 300 μL of concentrated mSA2 solution was then adjusted to pH 8.0 by adding 1M sodium bicarbonate. 1 mg of Alexa Fluor 647 NHS ester (Thermo Fisher Scientific) was then dissolved in 100 μL of amine-free, anhydrous DMF (Alfa Aesar), and 38 μL of this solution was immediately added to the mSA2 solution. The reaction was incubated in the dark at 4° C. for 24 hours. After incubation the solution was added to a NAP-10 column (GE Healthcare) and eluted with PBS (pH 7.4) to remove unconjugated dye molecules. The fractions containing dye-labeled mSA2 were combined and stored in the dark at 4° C. until further use.

Derivation of Expression for Fluorescent Binding Assay Curve-Fitting

Consider a solution of analyte added to a thin film of protein-polymer conjugates. Since the analyte can exist either in solution with concentration [A] or bound to the protein-polymer conjugate with concentration [A–P], a site balance can be written for the total concentration of the analyte $[A]_T$ as follows:

$$[A]+[A-P]=[A]_T, \qquad (1)$$

which can be solved for [A] to yield:

$$[A]=[A]_T-[A-P]. \qquad (2)$$

The protein-polymer conjugate can also exist in either the unbound state with concentration [P] or bound to the analyte with concentration [A–P], so a site balance can similarly be written for the total concentration of protein-polymer conjugate $[P]_T$ as follows:

$$[P]+[A-P]=[P]_T, \qquad (3)$$

which can be solved for [P] to yield:

$$[P]=[P]_T-[A-P]. \qquad (4)$$

By assuming the binding between the analyte and protein-polymer conjugate reaches equilibrium, a dissociation constant $K_d$ can be defined for the binding interaction:

$$K_d = \frac{[A][P]}{[A-P]}. \qquad (5)$$

Equations (2) and (4) can be substituted into equation (5) and solved for [A–P] to give the following equation:

$$[A-P] = \frac{([A]_T+[P]_T+K_d) \pm \sqrt{([A]_T+[P]_T+K_d)^2 - 4[A]_T[P]_T}}{2}. \qquad (6)$$

Since [A–P] must be less than both $[A]_T$ and $[P]_T$, only the negative root in equation (6) gives a physically reasonable solution:

$$[A-P] = \frac{\beta - \sqrt{\beta^2 - 4\gamma}}{2}, \qquad (7)$$

where β is defined as the sum of $[A]_T$, $[P]_T$, and $K_d$, and γ is defined as the product of $[A]_T$ and $[P]_T$. By assuming that the observed mean fluorescent intensity (MFI) from a fluorescent binding assay is proportional to the total number of binding events by some proportionality constant α such that α represents the average MFI per binding event, the MFI can be related to [A-P] by MFI=a[A-P], which can be substituted into equation (7) to give:

$$MFI = \frac{\alpha}{2}\left(\beta - \sqrt{\beta^2 - 4\gamma}\right). \quad (8)$$

where α is the average MFI per binding event and β and γ are defined as follows:

$$\beta = [A]_T + [P]_T + K_d, \quad (9)$$

$$\gamma = [A]_T[P]_T, \quad (10)$$

where $[A]_T$ represents the concentration of analyte molecules, $[P]_T$ is the total concentration of binding sites, and $K_d$ is the dissociation constant describing the binding equilibrium between analyte and binding sites. Thus, using the known concentration of analyte applied to the sensor surface $[A]_T$, the MFI can be expressed in terms of a, $[P]_T$, and $K_d$.

```
                               Sequences

SEQ ID NO: 16 1x rcSso7d.SA DNA Sequence
ATGGGCAGCATCCATCATCATCATCATCACAGCAGCGGCCTGGTGCCGCGCGGCAGCCATATGTGTGCAACCGTG
AAATTCACATACCAAGGCGAAGAAAAACAGGTGGATATTAGCAAAATCAAGATCGTGGCTCGTGACGGCCAGTAC
ATTGACTTTAAATATGATGAAGGTGGTGGTGCCTATGGTTATGGTTGGGTGAGCGAAAAAGATGCACCGAAAGAA
CTGCTGCAGATGCTGGAAAAGCAATAA SEQ ID NO: 17 1x rcSso7d.SA Amino Acid Sequence
MGSIHHHHHHSSGLVPRGSHMCATVKFTYQGEEKQVDISKIKIVARDGQYIDFKYDEGGGAYGYGWVSEKDAPKE
LLQMLEKQ SEQ ID NO: 18 2x rcSso7d.SA DNA Sequence
ATGGGCAGCAGCCATCATCATCATCATCACAGCAGCGGCCTGGTGCCGCGCGGCAGCCATATGTGTGCAACCGTG
AAATTCACATACCAAGGCGAAGAAAAACAGGTGGATATTAGCAAAATCAAGATCGTGGCTCGTGACGGCCAGTAC
ATTGACTTTAAATATGATGAAGGTGGTGGTGCCTATGGTTATGGTTGGGTGAGCGAAAAAGATGCACCGAAAGAA
CTGCTGCAGATGCTGGAAAAGCAAGGTGGTGGTGGTAGCGGTGGTGGCGGTTCAATGGCAACCGTGAAATTCACA
TACCAAGGCGAAGAAAAACAGGTGGATATTAGCAAAATCAAGATCGTGGCTCGTGACGGCCAGTACATTGACTTT
AAATATGATGAAGGTGGTGGTGCCTATGGTTATGGTTGGGTGAGCGAAAAAGATGCACCGAAAGAACTGCTGCAG
ATGCTGGAAAAGCAAGGTGGATAA SEQ ID NO: 19 2x rcSso7d.SA Amino Acid Sequence
MGSSHHHHHHSSGLVPRGSHMCATVKFTYQGEEKQVDISKIKIVARDGQYIDFKYDEGGGAYGYGWVSEKDAPKE
LLQMLEKQGGGGSGGGGSMATVKFTYQGEEKQVDISKIKIVARDGQYIDFKYDEGGGAYGYGWVSEKDAPKELLQ
MLEKQGG SEQ ID NO: 20 3x rcSso7d.SA DNA Sequence
ATGGGCAGCAGCCATCATCATCATCATCACAGCAGCGGCCTGGTGCCGCGCGGCAGCCATATGTGTGCAACCGTG
AAATTCACATACCAAGGCGAAGAAAAACAGGTGGATATTAGCAAAATCAAGATCGTGGCTCGTGACGGCCAGTAC
ATTGACTTTAAATATGATGAAGGTGGTGGTGCCTATGGTTATGGTTGGGTGAGCGAAAAAGATGCACCGAAAGAA
CTGCTGCAGATGCTGGAAAAGCAAGGTGGTGGTGGTAGCGGTGGTGGCGGTTCAATGGCAACCGTGAAATTCACA
TACCAAGGCGAAGAAAAACAGGTGGATATTAGCAAAATCAAGATCGTGGCTCGTGACGGCCAGTACATTGACTTT
AAATATGATGAAGGTGGTGGTGCCTATGGTTATGGTTGGGTGAGCGAAAAAGATGCACCGAAAGAACTGCTGCAG
ATGCTGGAAAAGCAAGGTGGTGGTGGTAGCGGTGGTGGCGGTTCAATGGCAACCGTGAAATTCACATACCAAGGC
GAAGAAAAACAGGTGGATATTAGCAAAATCAAGATCGTGGCTCGTGACGGCCAGTACATTGACTTTAAATATGAT
GAAGGTGGTGGTGCCTATGGATATGGTTGGGTGAGCGAAAAAGATGCACCGAAAGAACTGCTGCAGATGCTGGAA
AAGCAAGGTGGATAA SEQ ID NO: 21 3x rcSso7d.SA Amino Acid Sequence
MGSSHHHHHHSSGLVPRGSHMCATVKFTYQGEEKQVDISKIKIVARDGQYIDFKYDEGGGAYGYGWVSEKDAPKE
LLQMLEKQGGGGSGGGGSMATVKFTYQGEEKQVDISKIKIVARDGQYIDFKYDEGGGAYGYGWVSEKDAPKELLQ
MLEKQGGGGSGGGGSMATVKFTYQGEEKQVDISKIKIVARDGQYIDFKYDEGGGAYGYGWVSEKDAPKELLQMLE
KQGG SEQ ID NO: 22 4x rcSso7d.SA DNA Sequence
ATGGGCAGCAGCCATCATCATCATCATCACAGCAGCGGCCTGGTGCCGCGCGGCAGCCATATGTGTGCAACCGTG
AAATTCACATACCAAGGCGAAGAAAAACAGGTGGATATTAGCAAAATCAAGATCGTGGCTCGTGACGGCCAGTAC
ATTGACTTTAAATATGATGAAGGTGGTGGTGCCTATGGTTATGGTTGGGTGAGCGAAAAAGATGCACCGAAAGAA
CTGCTGCAGATGCTGGAAAAGCAAGGTGGTGGTGGTAGCGGTGGTGGCGGTTCAATGGCAACCGTGAAATTCACA
TACCAAGGCGAAGAAAAACAGGTGGATATTAGCAAAATCAAGATCGTGGCTCGTGACGGCCAGTACATTGACTTT
AAATATGATGAAGGTGGTGGTGCCTATGGTTATGGTTGGGTGAGCGAAAAAGATGCACCGAAAGAACTGCTGCAG
ATGCTGGAAAAGCAAGGTGGTGGTGGTAGCGGTGGTGGCGGTTCAATGGCAACCGTGAAATTCACATACCAAGGC
GAAGAAAAACAGGTGGATATTAGCAAAATCAAGATCGTGGCTCGTGACGGCCAGTACATTGACTTTAAATATGAT
GAAGGTGGTGGTGCCTATGGTTATGGTTGGGTGAGCGAAAAAGATGCACCGAAAGAACTGCTGCAGATGCTGGAA
AAGCAAGGTGGTGGTGGTAGCGGTGGTGGCGGTTCAATGGCAACCGTGAAATTCACATACCAAGGCGAAGAAAAA
CAGGTGGATATTAGCAAAATCAAGATCGTGGCTCGTGACGGCCAGTACATTGACTTTAAATATGATGAAGGTGGT
GGTGCCTATGGTTATGGTTGGGTGAGCGAAAAAGATGCACCGAAAGAACTGCTGCAGATGCTGGAAAAGCAATAA
```

-continued

Sequences

SEQ ID NO: 23 4x rcSso7d.SA Amino Acid Sequence
MGSSHHHHHHSSGLVPRGSHMCATVKFTYQGEEKQVDISKIKIVARDGQYIDFKYDEGGGAYGYGWVSEKDAPKE
LLQMLEKQGGGGSGGGGSMATVKFTYQGEEKQVDISKIKIVARDGQYIDFKYDEGGGAYGYGWVSEKDAPKELLQ
MLEKQGGGGSGGGGSMATVKFTYQGEEKQVDISKIKIVARDGQYIDFKYDEGGGAYGYGWVSEKDAPKELLQMLE
KQGGGGSGGGGSMATVKFTYQGEEKQVDISKIKIVARDGQYIDFKYDESGGAYGYGWVSEKDAPKELLQMLEKQ Sandwich Assays Bioconjugate thin films and rcSso7d.SA monolayers were cut into 0.25 cm-by-0.25 cm pieces and securely fastened to the bottom of Falcon polystyrene 12-well plates using double-sided carbon tape. Each well was submerged in 1 mL of 1% BSA in Milli-Q water, and the 12-well plate was incubated at 37° C. for 30 minutes. The wells were rinsed twice by adding 2 mL of Milli-Q water and gently shaking the well plate at 70 rpm for 5 minutes. 1 mL of streptavidin diluted in PBS, urine, or blood serum (prepared as described in the Fluorescent Assays section) containing 0.1% BSA was then added to each well, and the well plate was shaken at 70 rpm for 4 hours at room temperature. Wells were rinsed twice with 2 mL of Milli-Q water then twice with 2 mL of 0.1% BSA in Milli-Q water by shaking at 70 rpm for 5 minutes. After rinsing, wells were submerged in 1 mL of 200 ng/mL biotin-HRP in Milli-Q water containing 0.1% BSA, and the well plate was shaken at 70 rpm for 1 hour at room temperature. Wells were then rinsed with water and 0.1% BSA as described previously. 1 mL of solution from a Pierce TMB substrate kit (Thermo Fisher Scientific) was added to each well, and the well plate was shaken vigorously at 125 rpm for 15 minutes at room temperature. 1 mL of 2M H2SO4 was added to each well, and the absorbance at 450 nm was read using a Tecan Infinite M200 PRO plate reader.

Equation for GISAXS Linecut Curve-fitting

GISAXS linecuts were fit using the following model:

$$I(q) = \{Aq^{-4} + Bq^{-2} + C\} + \left\{I_0 \exp\left[\frac{-(q-q_0)^2}{2\sigma^2}\right]\right\}, \quad (11)$$

where the first term in braces accounts for background scattering with individual parameters to capture the scattering in the Porod regime, in the Guinier regime, and from a constant background, and the second term in braces represents a Gaussian fit to the observed peak where $I_0$ is the peak height, $q_0$ is the peak position, and $2\sqrt{2\ln(2)}\sigma$ is the FWHM. For 3xSP77.6k linecuts in which two peaks were observed, the second peak was fit by adding an additional term to the previous equation:

$$I_{0,2}\exp\left[\frac{-(q-2q_0)^2}{2\sigma_2^2}\right], \quad (12)$$

where $I_{0,2}$ represents the height of the second peak, the peak position is fixed at $2q_0$, and $2\sqrt{2\ln(2)}\sigma_2$ is the FWHM of the second peak.

Example 1. Phase Behavior

Figure 1B:
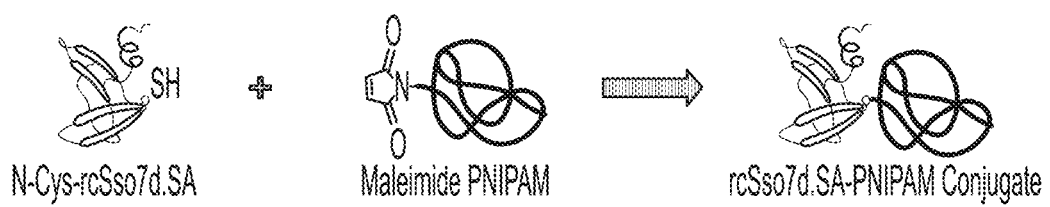

Oligomers of rcSso7d.SA, a modified DNA-binding protein designed to exhibit high-affinity streptavidin binding,[39] linked together by flexible $(Gly_4Ser)_2$ peptides (FIG. 1A),[57] were expressed and conjugated to poly(N-isopropylacrylamide) (PNIPAM) (FIG. 1B). Each oligomer—hereafter referred to as nx rcSso7d.SA, where n is the number of rcSso7d.SA proteins in the oligomer—was conjugated to PNIPAM of comparable molar mass as the oligomer (Table 2). A PNIPAM volume fraction could not be calculated for these protein-polymer block copolymers since the molar volume of the protein is not known, so all conjugates were synthesized with symmetric weight fraction, as this is the approximate condition at which optimal ordering has previously been observed in protein-polymer conjugates.[24]

TABLE 2

Composition of rcSso7d.SA oligomer-PNIPAM Conjugates

| Conjugate | Protein | Protein MW (kDa) | PNIPAM $M_n$ (kDa) | PNIPAM Đ | PNIPAM Weight Fraction |
|---|---|---|---|---|---|
| 1xSP9.8k | 1x rcSso7d.SA | 9.4 | 9.8 | 1.09 | 0.51 |
| 2xSP17k | 2x rcSso7d.SA | 17.1 | 16.8 | 1.10 | 0.50 |
| 3xSP25k | 3x rcSso7d.SA | 24.9 | 24.9 | 1.10 | 0.50 |
| 4xSP30k | 4x rcSso7d.SA | 32.5 | 30.0 | 1.10 | 0.48 |

Analysis of the four studied conjugates in concentrated solution suggests a clear effect of oligomerization (molar mass) on morphology. Phase diagrams are constructed for each conjugate (FIG. 2) using SAXS to determine nanostructure periodicity, DPLS to assess long-range ordering, turbidimetry to determine transitions to macrophase separated states, and DSC to estimate PNIPAM desolvation temperatures (Table 3). While the conjugates are assumed to exhibit equilibrium morphology under most of the studied conditions, 100 wt. % samples created by drying solutions under vacuum at a controlled pressure ramp rate of 50 Torr/h are known to be kinetically trapped in a weakly-ordered morphology.[24]

TABLE 3

Thermal Transitions for rcSso7d.SA Oligomer-PNIPAM Conjugates in Concentrated Solution

| Conjugate | Conc. (wt. %) | $T_{DPLS}^a$ (° C.) | $T_t^b$ (° C.) | $T_{DSC}^b$ (° C.) |
|---|---|---|---|---|
| 1xSP9.8k | 30 | ○ | 30.1 | 29.6 |
|  | 35 | ○ | 30.3 | 29.0 |
|  | 40 | ○ | 30.9 | 28.5 |
|  | 45 | ○ | 34.2 | 27.2 |
|  | 50 | ○ | 31.3 | 25.5 |
|  | 60 | ● | — | 24.8 |
|  | 70 | ○ | — | — |
| 2xSP17k | 30 | ○ | — | 28.7 |
|  | 35 | ○ | — | 28.6 |
|  | 40 | ○ | — | 27.3 |
|  | 45 | ○ | — | 26.1 |
|  | 50 | ○ | — | 25.4 |
|  | 60 | ● | — | — |
|  | 70 | ● | — | — |

TABLE 3-continued

Thermal Transitions for rcSso7d.SA Oligomer-PNIPAM
Conjugates in Concentrated Solution

| Conjugate | Conc. (wt. %) | $T_{DPLS}{}^a$ (° C.) | $T_t{}^b$ (° C.) | $T_{DSC}{}^b$ (° C.) |
|---|---|---|---|---|
| 3×SP25k | 30 | ○ | — | 27.8 |
| | 35 | ○ | — | 28.4 |
| | 40 | ● | — | 28.0 |
| | 45 | ● | — | 26.6 |
| | 50 | ● | — | 26.1 |
| | 60 | ● | — | 23.0 |
| | 70 | ● | — | — |
| 4×SP30k | 30 | ○ | — | 29.4 |
| | 35 | ○ | — | 28.3 |
| | 40 | ● | — | 27.5 |
| | 45 | ● | 26.1 | 26.0 |
| | 50 | ● | 26.7 | 25.4 |
| | 60 | ● | — | 22.1 |
| | 70 | ● | — | — |

$^a$○ denotes samples that never display birefringent behavior within the studied temperature range. ● denotes samples that remain birefringent throughout the entire studied temperature range.
$^b$The symbol "—" signifies that no thermal transition is observed at the given concentration.

Figure 2A:
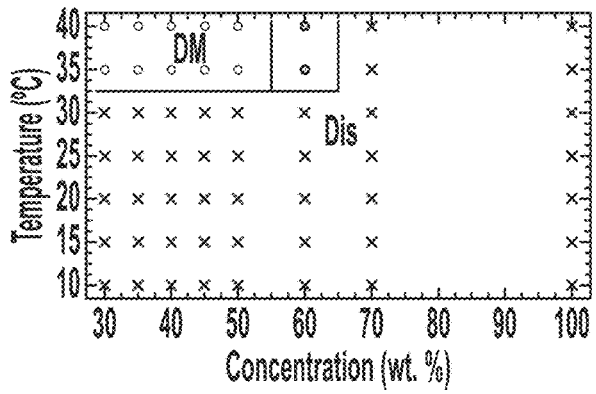
FIGS. 2A-2E. Phase diagrams of (FIG. 2A) 1×SP9.8k, (FIG. 2B) 2×SP17k, (FIG. 2C) 3×SP25k, and (FIG. 2D) 4×SP30k as a function of concentration and temperature. Phases are assigned in the diagrams as disordered (Dis), disordered micellar (DM), or lamellar (Lam) and are also (FIG. 2E) represented schematically. Light colored symbols represent non-birefringent lamellar phases, which are separated by dashed lines from shaded colored symbols representing birefringent lamellar phases. Solid symbols indicate a homogeneous phase, while open symbols indicate a macrophase-separated phase.
Figure 2B:
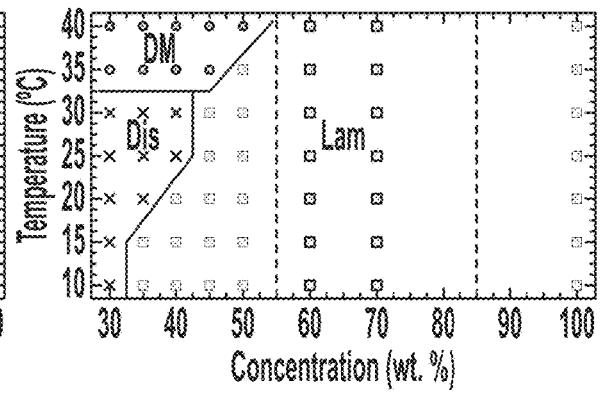
Figure 2C:
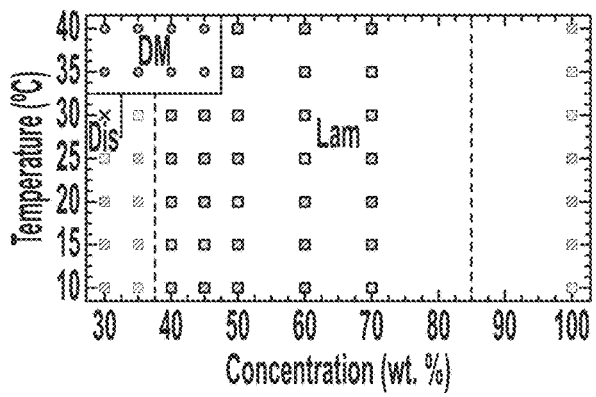
Figure 2D:
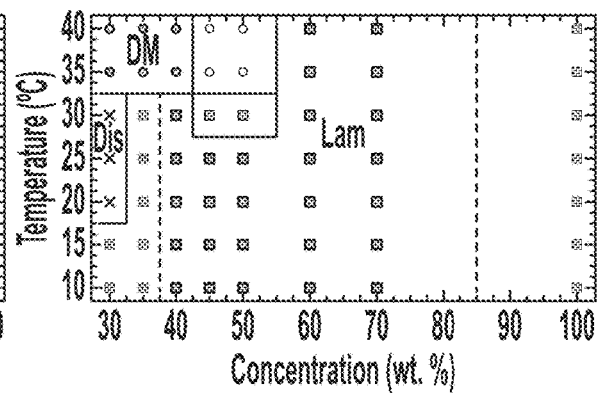
Figure 2E:
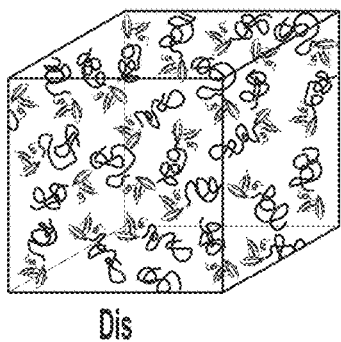
Figure 2E:
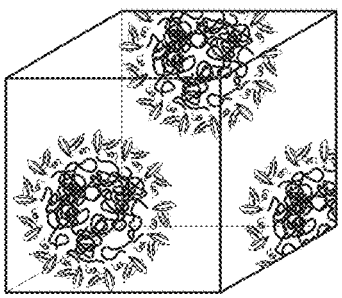
Figure 2E:
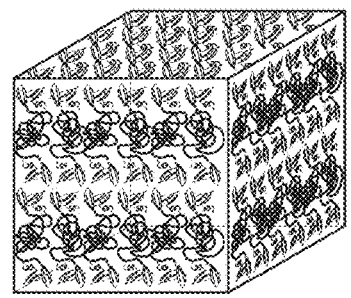

Conjugates containing oligomerized rcSso7d.SA protein blocks are observed to exhibit well-ordered structures. 1×SP9.8k remains disordered under all studied conditions (FIG. 2A), but all oligomer conjugates display lamellar morphology over a wide concentration range (FIGS. 2B-2D). The size of disordered regions in the phase diagrams also generally shrinks with increasing molecular weight of the protein block: 2×SP17k remains disordered up to concentrations of 40 wt. %, whereas 3×SP25k and 4×SP30k only display a disordered phase at 30 wt. %. Accordingly, the order-disorder transition concentration (CoDT) is decreased for higher-order oligomer conjugates, with values of 45, 35, and ≤30 wt. % (only concentrations as low as 30 wt. % were studied) for 2×SP17k, 3×SP25k, and 4×SP30k, respectively. Concentration ranges over which birefringent lamellae can be seen follow a similar trend, as the range expands from 60-70 wt. % for 2×SP17k to 40-70 wt. % for 3×SP25k and 4×SP30k.

Despite the significant differences in ordering between the four oligomer conjugates, their phase diagrams contain many similar attributes. At high temperatures where water is selective for the protein block, PNIPAM blocks collapse inward away from a water-rich phase, resulting in the formation of disordered micelles. As can be seen in the SAXS curves (FIG. 3A), increasing temperature results in a gradual decrease in intensity of the scattering peaks corresponding to periodic nanostructures, but above the PNIPAM transition temperature, these peaks are almost entirely replaced by form factor scattering from the micelles. In 1×SP9.8k and 4×SP30k solutions, macrophase separated regions between conjugate-rich and conjugate-poor phases of disordered micelles exist, and these regions always exist above the PNIPAM thermal transition temperature (Table 3). As concentration increases, the temperature at which this transition to a macrophase separated state occurs also increases, which has been attributed to the ability of the protein domains to accommodate water.[23] Once PNIPAM chains begin to collapse and expel water above their thermal transition temperature, the excess water is initially accommodated through swelling of the protein domains. Above a certain temperature, the excess water can no longer be taken up by the proteins, resulting in the separation of micelles from a water-rich phase. As conjugate concentration increases, more protein is present to accommodate water from collapsed PNIPAM chains, so the macrophase separation transition temperature increases and—at high concentrations—does not occur below 40° C., indicating that the water is fully accepted into the protein domains.

Many similarities also exist between the three conjugates that form ordered phases. Below the thermal transition temperature of PNIPAM where water acts as a good solvent for both blocks, lamellar phases are observed. This strong preference for lamellae is consistent with phase behavior in rod-coil diblock copolymers,[637] which, similar to protein-polymer block copolymers, contain one rigid and one flexible block. Unlike previous work analyzing the self-assembly of protein-PNIPAM conjugates of mCherry and GFP,[28] no hexagonally packed cylinder phase is observed in any of the rcSso7d.SA oligomer conjugates. However, this phase was only seen when PNIPAM represented the minority block in both volume and weight fraction. In this study where only symmetric diblocks were considered, it is likely that the volume fraction of the polymer block is not low enough to thermodynamically favor bending of the protein-polymer interface to form cylindrical nanodomains. Below 45 wt. %, increases in concentration promote the formation of well-defined lamellar phases (FIG. 13B) with increasing birefringence (FIGS. 15-18) for 2×SP17k, 3×SP25k, and 4×SP30k. In highly concentrated solutions, though, ordering worsens as peaks significantly broaden, which is suggestive of the re-entrant order-disorder transition (ODT) behavior that has been previously observed in protein-polymer conjugates.[24-25]

DSC measurements of PNIPAM desolvation temperatures reveal clear trends within and across the studied rcSso7d.SA oligomer-PNIPAM conjugates. All four conjugates display decreasing transition temperatures with increasing concentration, consistent with previous findings in protein-polymer conjugates.[23,28-29] As the molecular weight of the PNIPAM block increases, the transition temperatures at a given concentration also generally decrease. This trend agrees with findings for homopolymer solutions of PNIPAM and other polymers with LCST behavior:[638] as polymer molecular weight increases, the exothermic contribution from polymer solvation decreases relative to the magnitude of the entropic penalty associated with the corresponding decrease in solvent free volume.[639] However, the PNIPAM desolvation temperature appears to be a weaker function of molar mass in the considered block copolymers, presumably a result of both the decreased free volume contribution from chain ends as well as differences in solvent partitioning in block copolymers compared to homopolymer solutions.

Example 2. Ordering Quality

Concentrated Solution.

Figure 4A:
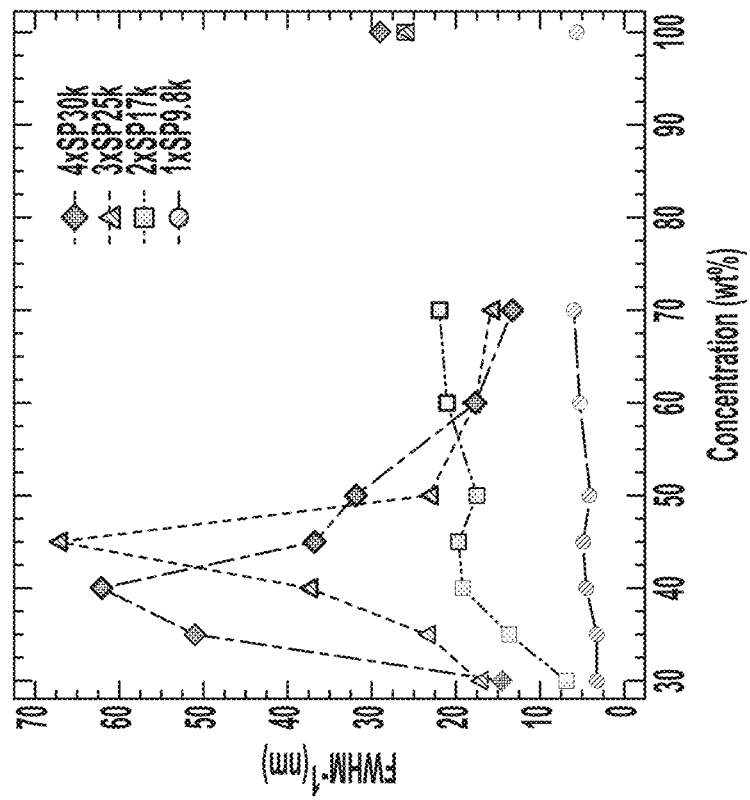
FIGS. 4A-4B. Ordering quality of rcSso7d.SA oligomer-PNIPAM conjugates indicated through (FIG. 4A) SAXS curves and (FIG. 4B) $FWHM^{-1}$ of the primary scattering peak. SAXS curves in (FIG. 4A) are each collected at 25° C., with the curves for 1×SP9.8k, 2×SP17k, and 3×SP25k collected at 45 wt. % and the curve for 4×SP30k collected at 40 wt. %. In graph (FIG. 4B), open symbols represent disordered phases, light symbols represent non-birefringent lamellar phases, and shaded symbols indicate a birefringent lamellar phase. Bulk data are disconnected from concentrated solution data to indicate that the 100 wt. % data are not at equilibrium.

Increased degree of oligomerization in the protein block of rcSso7d.SA oligomer-PNIPAM conjugates produces a significantly enhanced ordering quality in concentrated solution. This improved ordering is apparent by mere visual inspection of the SAXS curves for each conjugate at the concentration where the strongest ordering is observed at 25° C. (FIG. 4A). While 1×SP9.8k shows a single, broad scattering peak indicative of disordered structure, all three conjugates containing oligomerized rcSso7d.SA protein blocks display long-range periodic structures, as signified by the presence of higher-order scattering peaks. As the degree of oligomerization of the protein block increases, scattering peaks narrow, and ordering quality improves.

Figure 4B:
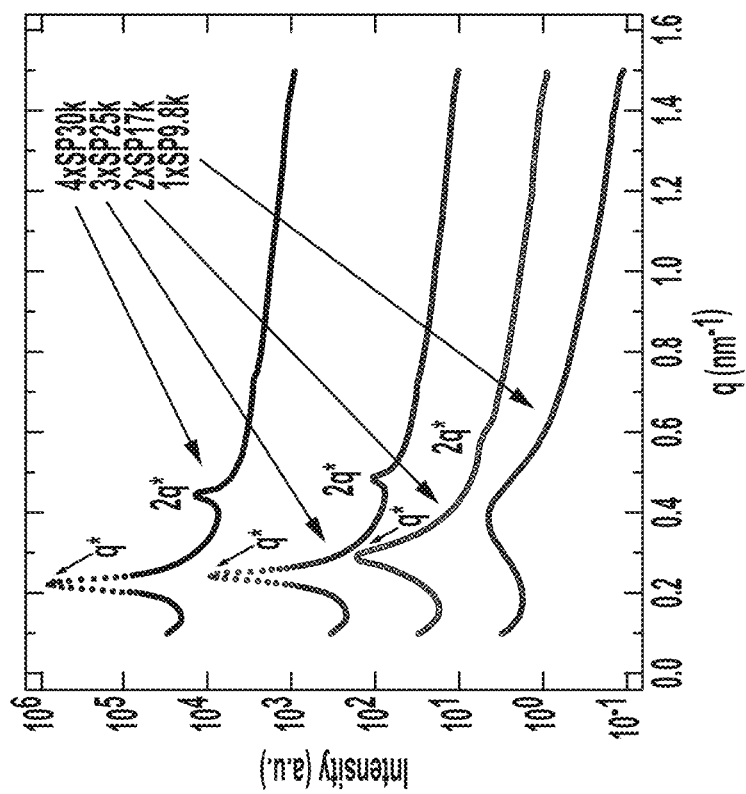

A more quantitative measure of this enriched ordering can be obtained by calculating the full width at half maximum (FWHM) of the primary scattering peak. FWHM were calculated by simultaneously fitting a Lorentzian to the primary scattering peak and a background function to the scattering intensity as follows:

$$I(q) = \{Aq^{-4} + Bq^{-2} + C\} + \left\{I_0\left[\frac{\gamma^2}{(q-q_0)^2 + \gamma^2}\right]\right\}$$

where the first term in braces accounts for background scattering with individual parameters to capture the scattering in the Porod regime, in the Guinier regime, and from a constant background, and the second term in braces represent the Lorentzian fit where his the peak height, $q_0$ is the peak position, and $2\gamma$ is the FWHM. In FIG. 4B, where $FWHM^{-1}$ values are plotted so greater values correspond to stronger ordering, oligomerization of rcSso7d. SA can be seen to produce up to an order of magnitude improvement in these values compared to 1×SP9.8k conjugates, which never achieve a $FWHM^{-1}$ greater than 6 nm. Again, ordering increases with degree of oligomerization of the protein block, with 3×SP25k and 4×SP30k conjugates displaying highly-ordered structures between 40 and 45 wt. %. At concentrations less than 60 wt. %, the $FWHM^{-1}$ value also serves as a very good indicator of phase behavior in these four studied conjugates. For $FWHM^{-1}$ less than 18 nm, conjugates almost exclusively form disordered phases, for $FWHM^{-1}$ between 18 and 23 nm, primarily non-birefringent lamellae are observed, and for $FWHM^{-1}$ greater than 23 nm, conjugates self-assemble into birefringent lamellae. At and above 60 wt. %, however, these phase predictions fail, as all lamellae not in the bulk state are birefringent. This is expected based on previous studies where the materials are shown to transition into a nematic phase as concentration increases out of the lamellar region.[25]

Highly Concentrated Solution.

Phase behavior in highly concentrated solutions (classified here as concentrations greater than or equal to 60 wt. %) deviates significantly from that at lower concentrations. At and above 60 wt. %, 3×SP25k and 4×SP30k conjugates experience a drop in $FWHM^{-1}$ from lower concentrations, suggesting a disordering of lamellar nanophases (FIG. 4B). This observation is in stark contrast to typical phase behavior in concentrated block copolymer solutions, where ordering is predicted[26] and observed[69-70] to strictly increase as a function of concentration, regardless of solvent selectivity. Though uncommon, this type of disordering has previously been observed in block copolymer solutions, typically as re-entrant ODT phase behavior. In polystyrene-b-polyisoprene (PS-PI) diblock copolymers in diethyl phthalate, a strongly selective solvent for PS, a thermotropic re-entrant ODT has been observed at low polymer concentration (0=0.2), where heating causes phase changes from a disordered micellar phase to FCC-arranged micelles and finally to a disordered phase.[71] A lyotropic re-entrant ODT has also been documented in PS-PI solutions in decane (selective for PI) between 10 and 16 wt. % as a BCC phase composed of PS-PI micelles disorders then re-forms the BCC phase.[72] In this latter system, the odd phase behavior has been postulated to be a non-equilibrium effect that results from kinetic trapping of the micelles as the cores become glassy.[70] Re-entrant ODT behavior has been observed in previously-studied protein-polymer conjugates at high concentration as well,[24-25] for which it has been hypothesized that protein-polymer interactions become net attractive at high concentration.[25]

Figure 5A:
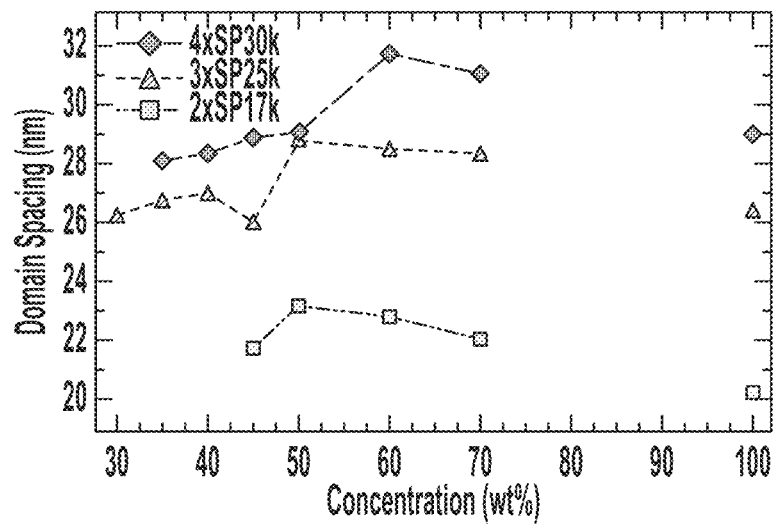
FIGS. 5A-5C.
Figure 5B:
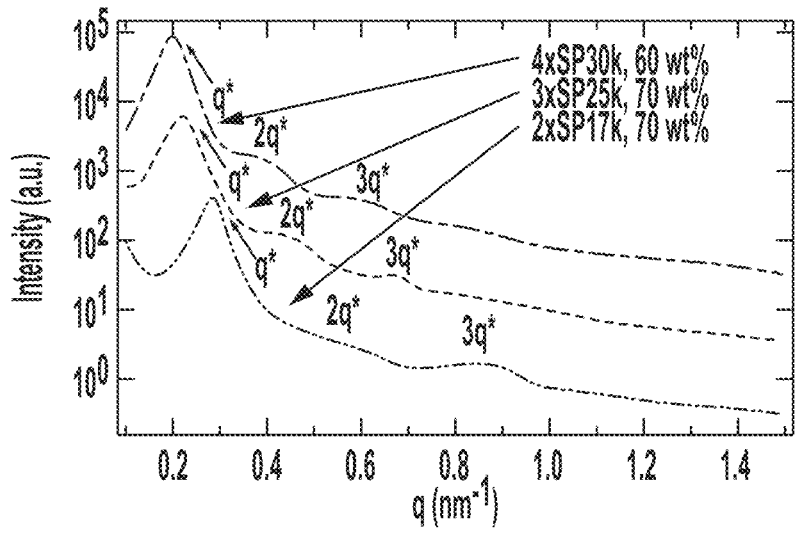
Figure 5C:
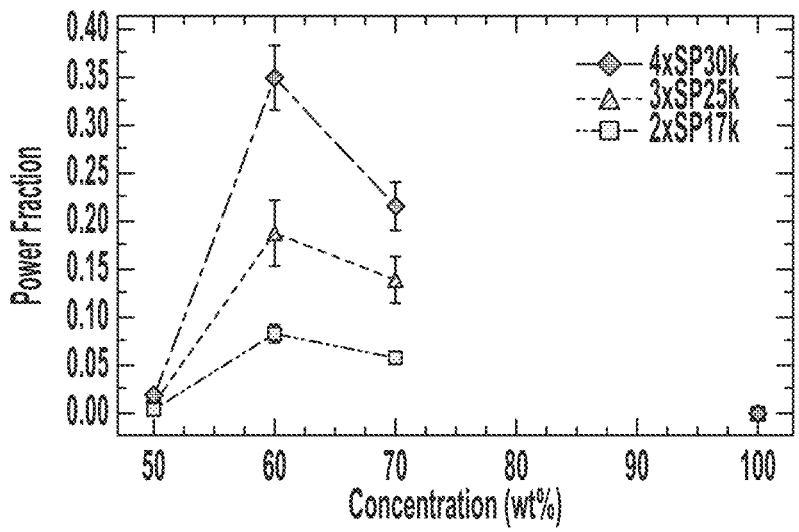
Figure 20A:
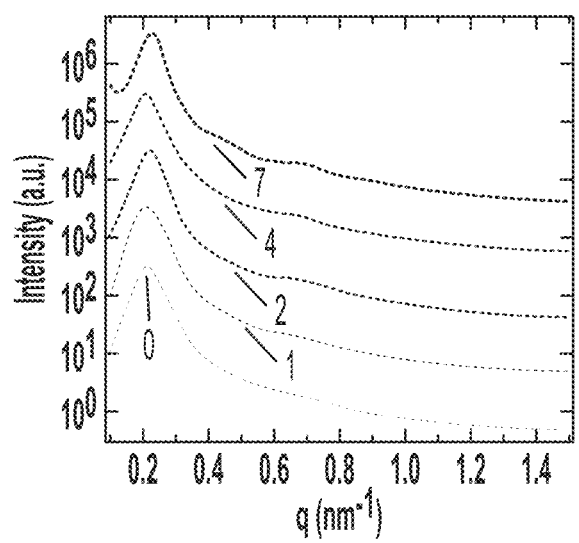
FIGS. 20A-20C. Effect of incubation time on ordering quality in 70 wt. % 3×SP25k samples.
Figure 20B:
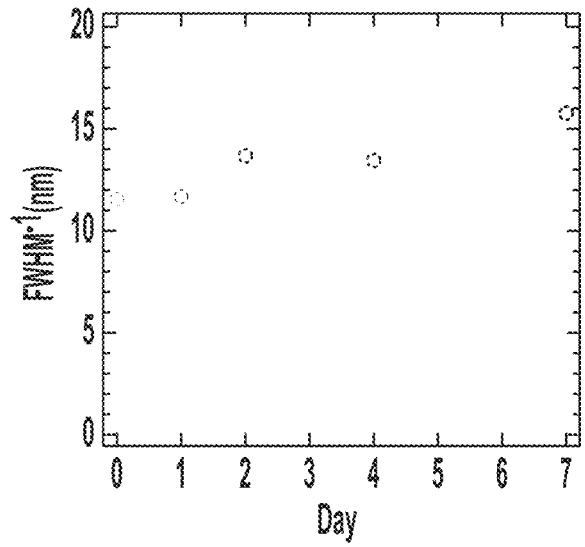
Figure 20C:
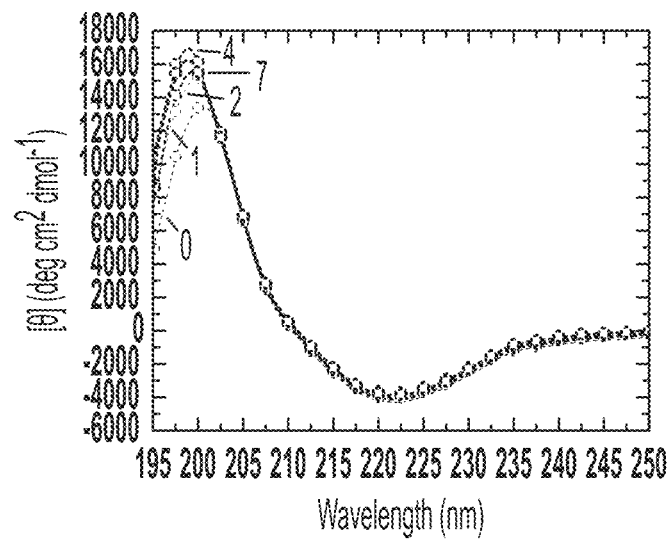

In this study, domain spacing analysis also reveals atypical behavior for block copolymers in highly concentrated solutions. For diblock copolymer solutions, domain spacing analysis can be performed to reveal the selectivity of a solvent towards each block through a power law relationship: domain spacing d scales with polymer volume fraction ϕ according to $d \sim \phi^{-\beta}$, where the value of exponent β is indicative of solvent selectivity.[73] In general for nonselective and weakly selective solvents, β is negative, and domain spacing increases with polymer volume fraction as the solvent slightly preferentially migrates to the interfaces between phases to screen unfavorable interactions between the two blocks.[73-74] Conversely, for strongly selective solvents β becomes positive—as high as unity—as one phase swells with added solvent to minimize interfacial area and therefore unfavorable solvent interactions with the insoluble block. Previously, water has been found to be slightly selective for the PNIPAM block in protein-PNIPAM conjugates,[23] and—accordingly—lamellar domain spacing increases with concentration at relatively low concentrations in the rcSSo7d.SA oligomer conjugates considered here (FIG. 5A). However, in highly concentrated solution, the domain spacing of all lamellae-forming conjugates decreases with increasing concentration, seemingly suggesting that water becomes a selective solvent at high concentration. Similar domain spacing behavior has previously been observed in highly concentrated PS-PI solutions near room temperature,[75-76] for which it was proposed that the decrease in domain spacing resulted primarily from chain swelling effects due to reduced mobility of the polymer chains under these conditions. When incubated at room temperature, the conjugates in this study do in fact show a slight improvement in ordering as incubation time is increased (FIG. 20). While the results here display qualitative agreement with this theory, the PS-PI systems exhibited a continuous change in domain spacing across all compositions whereas the rcSso7d.SA oligomer-PNIPAM conjugates all contain a discontinuity between the regions of increasing and decreasing domain spacing. Thus, even if similar kinetic control of domain spacing is occurring in the studied systems, additional features of the conjugates beyond chain swelling appear to also have a significant effect on the self-assembly dynamics.

The long-range ordering of highly concentrated solutions of the studied bioconjugates exhibits key differences from that at lower concentrations. All lamellae-forming conjugates display q* reflections up to 3q* at concentrations at and above 60 wt. % (FIG. 6B) while only reflections up to 2q* are observed at lower concentrations, indicating retention of lamellar ordering over longer length scales at higher concentration—at least within small grains. Birefringence signals also display substantial increases between 50 wt. % and 60 wt. % in these conjugates (FIG. 6C). It is unlikely that these jumps in birefringence correspond to an improvement in long-range lamellar ordering, however, as 2×SP17k and 3×SP25k bulk samples also display lamellar reflections up to 3q* (FIGS. 12-13) but are not birefringent (FIG. 7C). Indeed, even the 1×SP9.8k conjugates display a weak birefringent signal at 60 wt. % (Table 3, FIG. 15F) despite being highly disordered at this concentration. Instead, the increased birefringence signal is presumably a result of orientational ordering within the sample, similar to the nematic ordering previously observed at 70 and 80 wt. % in mCherry protein-polymer conjugates.[25]

Biosensing Capabilities

Figure 21:
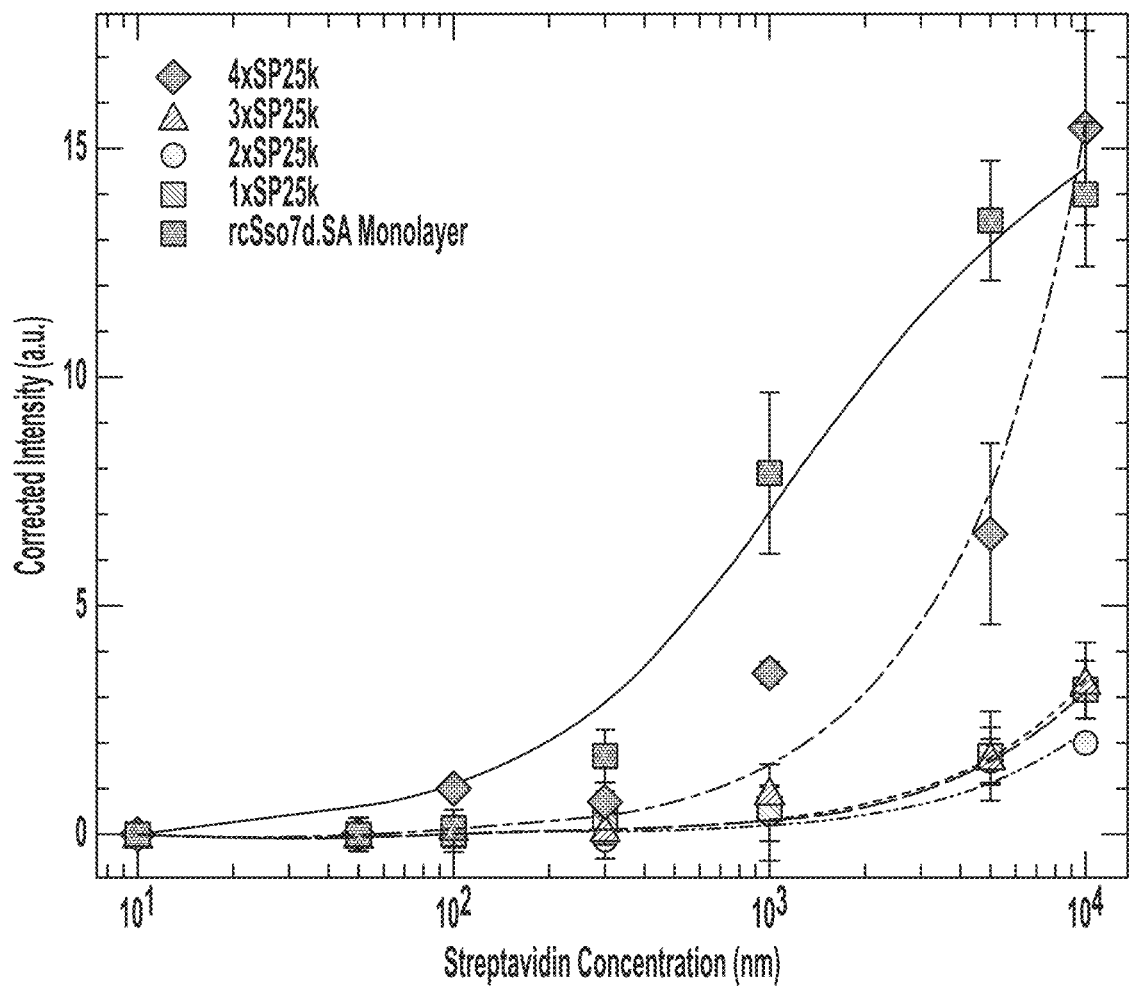
FIG. 21. Comparison of binding curves obtained for each considered conjugate and rcSso7d.SA monolayer using streptavidin labeled with Alexa Fluor 647 as the analyte. All curves are shifted to a background signal of 0 for clarity. Thicknesses for the 1×SP9.8k, 2×SP17k, 3×SP25k, and 4×SP30k films are 120, 90, 80, and 135 nm, respectively. Error bars represent the standard deviation of three replicates.

To confirm the sensing capabilities of rcSso7d.SA in oligomerized states, binding assays were performed. It has previously been demonstrated that protein-polymer block copolymers display size-exclusion properties in which molecular diffusion into the conjugates is controlled by diffusion through the polymer nanodomains, as only molecules of sufficiently lower molecular weight than the polymer block can diffuse into the matrix.[31] Correspondingly, diffusion experiments using streptavidin—the biomolecule which rcSso7d.SA was genetically modified to bind—as the analyte displayed weak binding strength relative to an rcSso7d.SA monolayer (FIG. 21). It was reasoned that due to the large molar mass of streptavidin (53 kDa), very large (~100 kDa) PNIPAM molecules would need to be synthesized and conjugated to the rcSso7d.SA oligomers to permit free diffusion. With a much higher polymer weight fraction, conjugates of these high-$M_n$ PNIPAM molecules would represent a significant departure in ordering behavior from the symmetric weight fraction conjugates studied here. Because streptavidin is a tetrameric species, it was assumed that a smaller, monomeric streptavidin variant (14 kDa) would display only a slightly weaker binding strength to rcSso7d.SA due to the lack of multivalent binding effects[76-77-6] but experience little resistance to diffusion even in low molecular weight PNIPAM blocks. Thus, a monomeric form of streptavidin, mSA2,[78-79] was selected as the analyte for assays.

Figure 6A:
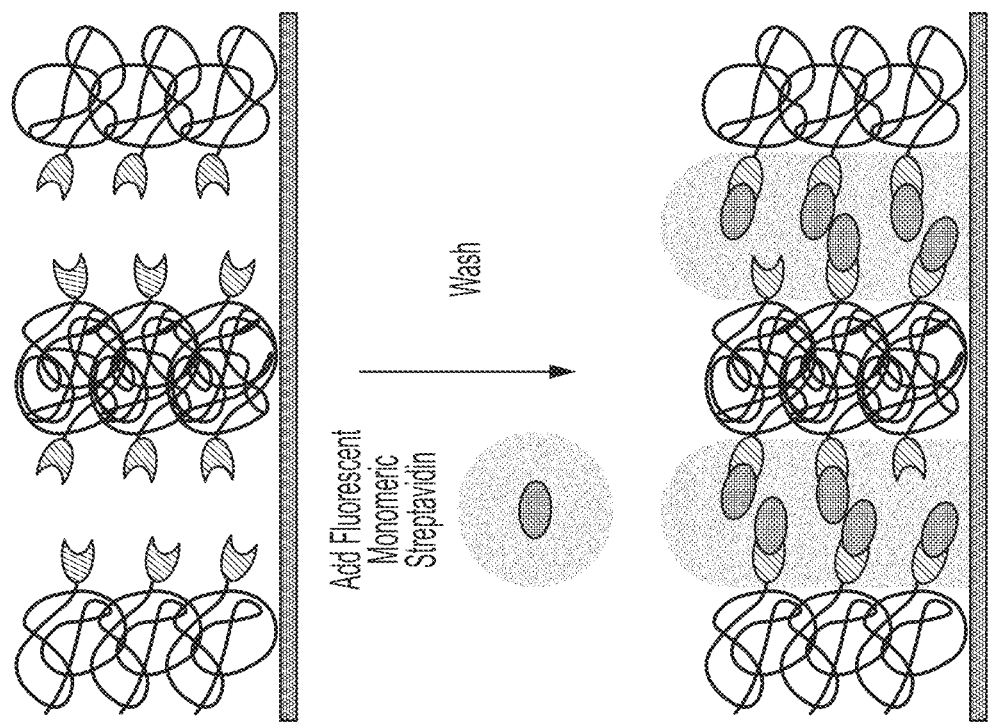
FIGS. 6A-6C.

Binding assays were performed by adding serially diluted solutions of fluorescently-labeled mSA2 to thin films of each studied conjugate (FIG. 6A). To maintain consistent transport properties between samples, each oligomer was conjugated to the same previously-synthesized 25 kDa PNIPAM sample. Analyte bound to thin films was quantified using fluorescence microscopy, and binding curves were fit to the collected mean fluorescent intensity (MFI) data using the following equation:

$$MFI = \frac{\alpha}{2}\left(\beta - \sqrt{\beta^2 - 4\gamma}\right)$$

where $\alpha$ is the average MFI per binding event, $\beta$ represents the sum of the total concentration of analyte molecules, total concentration of binding sites, and dissociation constant describing the binding equilibrium, and $\gamma$ is the product of two aforementioned concentrations. A derivation of this equation is provided above.

Curve fits performed on the binding assay data gave reasonable parameter values. Each fit yielded the same $\alpha$ value—which should be independent of sensor type—within the parameter uncertainty, demonstrating good self-consistency of the model. All thin film sensors also gave values for the total concentration of accessible binding sites $[P]_T$ significantly greater than that for the monolayer, as expected due to the greater thickness and thus total protein present in the thin films. Dissociation constant $K_d$ values for the conjugate thin film biosensors, however, are unreasonable large. These extremely high values likely result from the apparent rightward shift in fluorescent intensity values compared to the monolayer; since the $K_d$ parameter is the only parameter in the used model that can significantly control left/right movement of the binding curve, this value presumably increased to accommodate the shift. Though it leads to inflated $K_d$ values, the rightward shift of the binding curve in the thin film samples is consistent with behavior previously observed when increasing the concentration of binding sites within a protein biosensor.[18]

TABLE 4

Best-fit Parameter Values for Fits to Monomeric Streptavidin Binding Assays

| Biosensor | $\alpha^a$ (MFI/nM) | $[P]_T^a$ (nM) | $K_d^a$ (nM) |
|---|---|---|---|
| rcSso7d.SA Monolayer | 100 ± 10 | 0.34 ± 0.05 | 2000 ± 1000 |
| 1×SP25k Thin Film | 100 ± 10 | 3100 ± 400 | $8 \times 10^7 \pm 1 \times 10^7$ |
| 2×SP25k Thin Film | 100 ± 10 | 3300 ± 500 | $6.0 \times 10^7 \pm 9 \times 10^6$ |
| 3×SP25k Thin Film | 120 ± 20 | 3900 ± 700 | $4.7 \times 10^7 \pm 9 \times 10^6$ |
| 4×SP25k Thin Film | 112 ± 9 | 3700 ± 300 | $5.2 \times 10^7 \pm 4 \times 10^6$ |

$^a$Parameter ranges represent 95% confidence intervals for the parameter estimate.

Figure 6B:
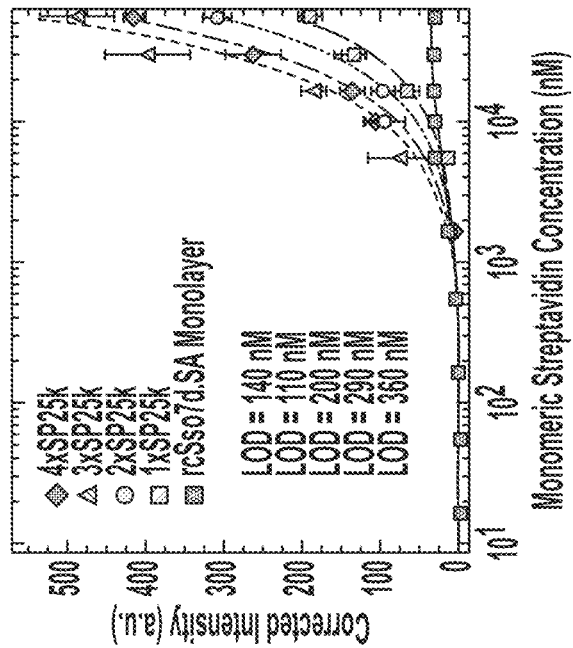
Figure 6C:
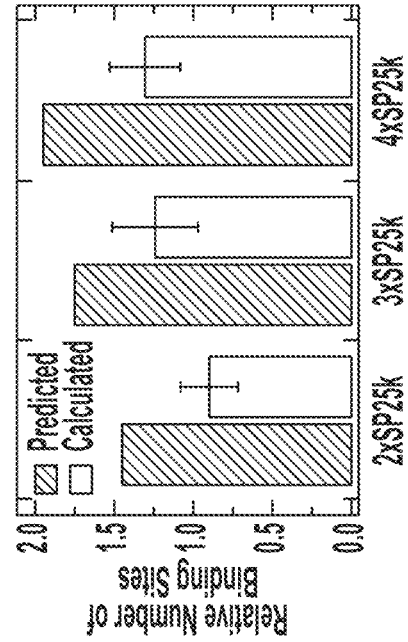

Analysis of binding curves indicates that rcSso7d.SA oligomer conjugates not only retain binding capacity, but also significantly enhance rcSso7d.SA biosensing capabilities (FIG. 6B). All conjugate samples show increased fluorescent signal at high concentration relative to a rcSso7d.SA monolayer, with the conjugate of the trimer displaying an improvement of over an order of magnitude at the highest measured concentration. Additionally, while the fluorescent intensity of the monolayer saturates for concentrations above 5 μM, all thin film samples show continually increasing signal at high analyte concentrations. Unlike the monolayer, the thin film samples contain densely-packed proteins in three-dimensions, thereby providing substantially more binding sites within the sensor and allowing distinction between a greater range of analyte concentrations before saturating. All binding curves are also considerably right-shifted compared to previously-reported curves for rcSso7d.SA in yeast-display experiments,[39] though the presence of an equivalent shift in the monolayer binding curve indicates that the weaker binding is not a result of inherently worse binding kinetics within the conjugate thin films. The monolayer curve does, however, indicate similar binding strength compared to previous surface-immobilized rcSso7d.SA assays using streptavidin as the analyte,[18, 39] indicating that rcSso7d.SA has similar binding affinities for streptavidin and mSA2.

Oligomerization of rcSso7d.SA also brings about a decrease in biosensor limit of detection (LOD). By calculating LOD using the standard definition as the minimum concentration which gives a signal three standard deviations above that of the average blank, it is found that the LODs for the monolayer and 1×SP25k, 2×SP25k, 3×SP25k, and 4×SP25k thin films are 360, 290, 200, 110, and 140 nM, respectively. While all thin films display improvements up to threefold in LOD over the monolayer, the trend in LOD with respect to degree of oligomerization is non-monotonic. The primary factor that is expected to affect LOD in the studied biosensors is number of binding sites, as more binding sites enable a greater number of analyte molecules to be captured and shifts analyte-receptor equilibrium in favor of binding events. Since the number of binding sites is a function of both the density of accessible rcSso7d.SA proteins within a plane parallel to the underlying substrate and the number of these planes within a biosensor, both rcSso7d.SA volume fraction and film thickness are required to determine the number of these sites.

Figure 35:
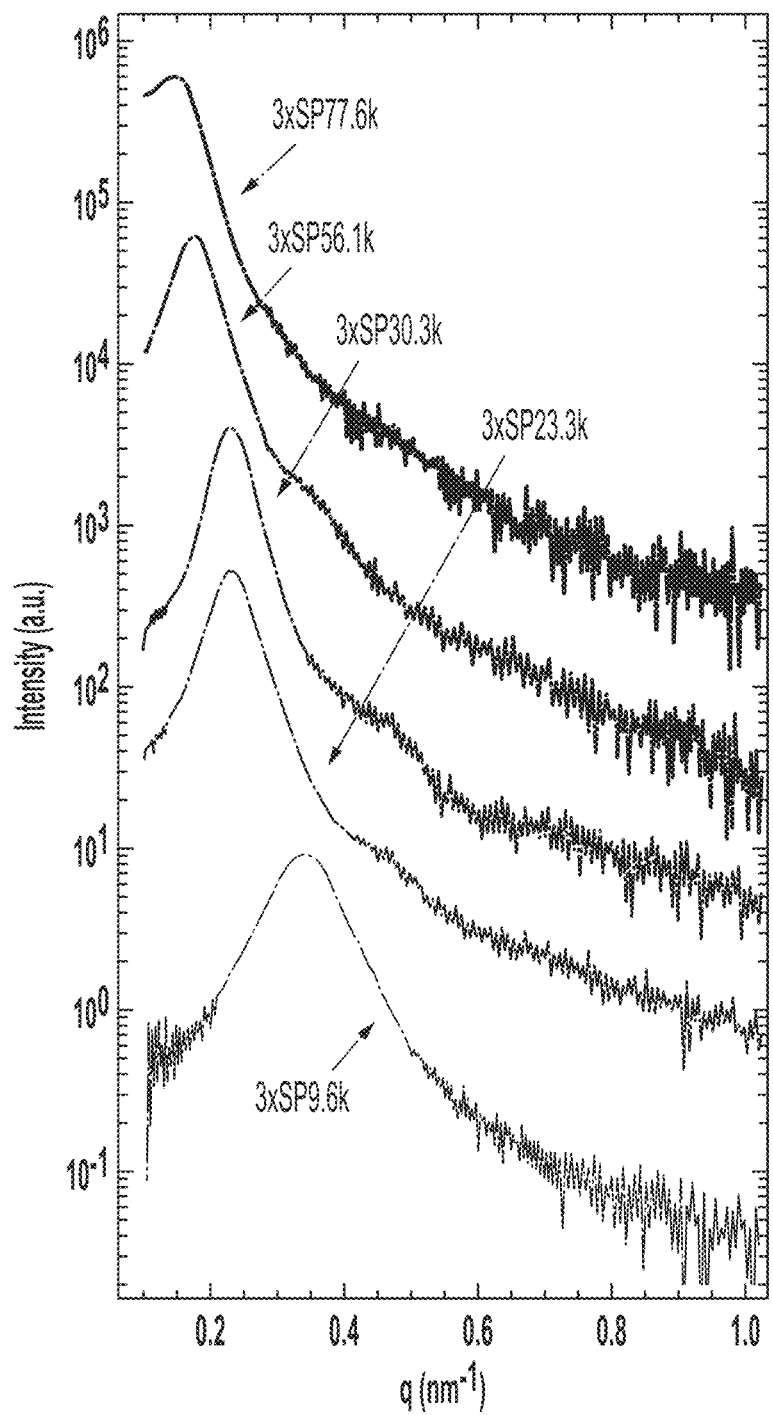
FIG. 35. Bulk SAXS curves for synthesized conjugates at ambient conditions.

Calculation of the number of binding sites reveals a significant increase in both number and density of available sites in conjugate thin films relative to rcSso7d.SA monolayers. To determine the density of binding proteins within a single plane of each thin film, the concentration of accessible binding sites throughout the entire film—taken directly from the binding assay curve fits (Table 4)—was multiplied by the corresponding film thickness. When accounting for differences in film thickness, the density of oligomerized rcSso7d.SA proteins capable of binding mSA2 is found to increase monotonically with degree of oligomerization (Table 5). This calculated density decreases, though, between the 1×SP25k and 2×SP25k thin films, indicating a lower density of accessible binding sites in the protein domains of the oligomerized rcSso7d.SA conjugate film. The total number of predicted binding sites within each thin film assuming complete accessibility should be proportional to the volume fraction of rcSso7d. SA in the conjugate with PNIPAM. Reasonable estimates for relative values of the predicted number of sites can thus be obtained by normalizing the weight fraction of rcSso7d. SA in each conjugate by the corresponding weight fraction in 1×SP25k. Comparing these predicted relative number of binding sites to the calculated values (FIG. 6C), all oligomeric rcSso7d.SA conjugates are found to contain fewer proteins capable of binding mSA2 than predicted. It is likely that this effect results from a combination of steric blocking of binding sites by bound mSA2 molecules as well as a lack of the free volume required to incorporate mSA2 molecules into the protein nanodomains at high degrees of binding. Despite the lower than expected binding capacity of the conjugate thin films, these biosensors contain approximately $10^4$ times the quantity of accessible binding sites compared to rcSso7d.SA monolayers on a volumetric basis (Table 4). Recognizing that each plane (and a monolayer) of rcSso7d.SA proteins is roughly 1-2 nm thick,[80] the studied thin films can be determined to contain approximately 100 more planes of protein than a monolayer. Therefore, by accounting for differences in height between the thin films and monolayers, the thin films are found to contain around 2 orders of magnitude more moles of accessible protein per area, offering a significant improvement in protein density over traditional surface-immobilized protein biosensors.

bulk conjugate samples (FIG. 35, Table 7), presumably due to the swelling of PNIPAM causing an expansion of domains in the films.

TABLE 6

Composition of 3x reSso7d.SA-PNIPAM Conjugates

| Conjugate | PNIPAM $M_n$ (kDa) | PNIPAM Đ | Protein Weight Fraction | Domain Spacing[a] (nm) |
|---|---|---|---|---|
| 3xSP9.6k | 9.6 | 1.05 | 0.72 | 21.9 |
| 3xSP23.3k | 23.3 | 1.06 | 0.52 | 30.6 |
| 3xSP30.3k | 30.3 | 1.08 | 0.45 | 32.0 |
| 3xSP56.1k | 56.1 | 1.11 | 0.31 | 43.5 |
| 3xSP77.6k | 77.6 | 1.13 | 0.24 | 53.9 |

Figure 22A:
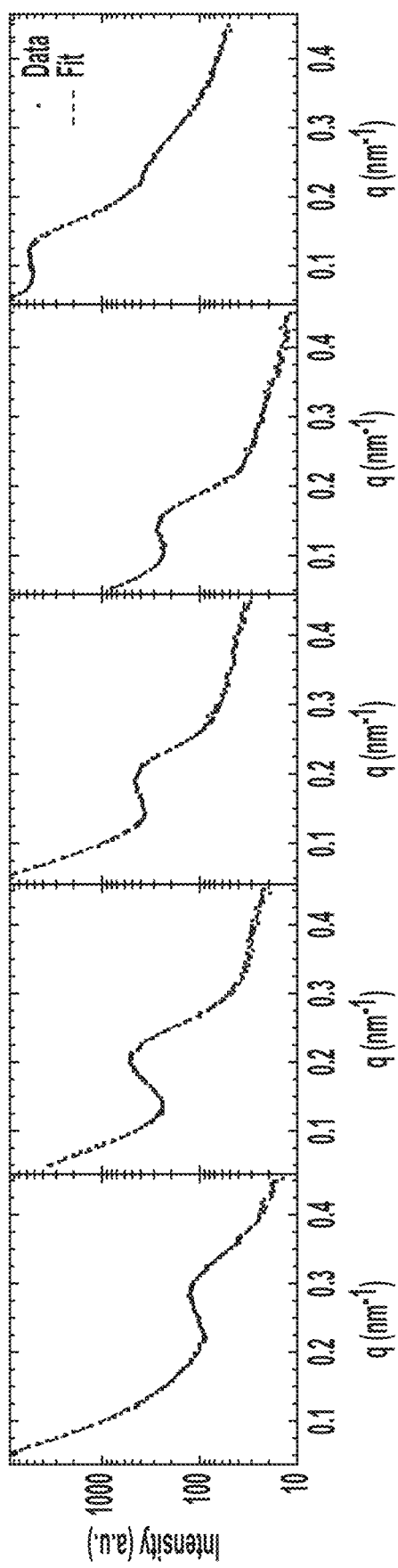
FIGS. 22A-22B. Grazing-incidence Small-angle X-ray Scattering (GISAXS) data. Fit GISAXS horizontal linecuts used to calculate domain spacing in swollen thin films (FIG. 22A) and corresponding GISAXS patterns (FIG. 22B). Images represent data for 3×SP9.6k, 3×SP23.3k, 3×SP56.1k, and 3×SP776.k (left to right). GISAXS patterns were collected at an incident angle of 0.140°.
Figure 22B:
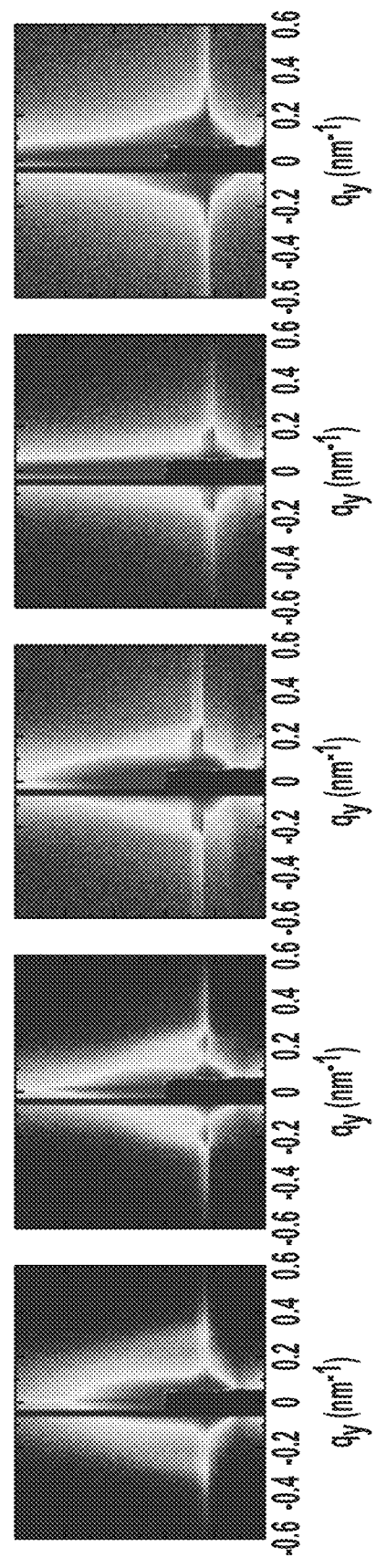

[a]Calculated from GISAXS horizontal linecuts (FIG. 22).

TABLE 7

Comparison of Bulk and Thin Film Domain Spacings

| Conjugate | Bulk Domain Spacing (nm)[a] | Film Domain Spacing (nm)[b] |
|---|---|---|
| 3xSP9.6k | 18.4 | 21.9 |
| 3xSP23.3k | 26.9 | 30.6 |
| 3xSP30.3k | 27.5 | 32.0 |
| 3xSP56.1k | 35.9 | 43.5 |
| 3xSP77.6k | 43.5 | 53.9 |

[a]Measured using bulk samples at ambient conditions.
[b]Measured at 95% RH.

Fluorescent assays performed on the thin films revealed gradual uptake of analyte. To assess effects of analyte size on diffusion into the films, the two aforementioned analytes that could be detected by the biosensor, SA (52.8 kDa) and mSA2 (15.6 kDa), were fluorescently-labeled, exposed to the films for a prescribed time, rinsed, and measured for

TABLE 5

Intermediate Values in Calculation of Relative Number of Binding Sites

| Thin Film | Weight Fraction[a] | Predicted Ratio[b] | Thickness (nm) | Calculated $[P]_T$ (nM) | Density[c] (μmol/cm$^2$) | Calculated Ratio[d] |
|---|---|---|---|---|---|---|
| 1xSP25k | 0.27 | 1.00 | 155 | 3100 | 48 | 1.00 |
| 2xSP25k | 0.39 | 1.43 | 130 | 3300 | 43 | 0.90 |
| 3xSP25k | 0.47 | 1.73 | 150 | 3900 | 59 | 1.24 |
| 4xSP25k | 0.53 | 1.94 | 170 | 3700 | 62 | 1.31 |

[a]Calculated as the weight fraction of rcSso7d.SA protein in the conjugate.
[b]Ratios of weight fractions relative to the 1xSP25k thin film.
[c]Density of binding sites within a cross-sectional area of the film parallel to the surface.
[d]Ratios of the product of film thickness and $[P]_T$ relative to the 1xSP25k thin film.

Characterizing Diffusion into Biosensor Thin Films

Figure 23A:
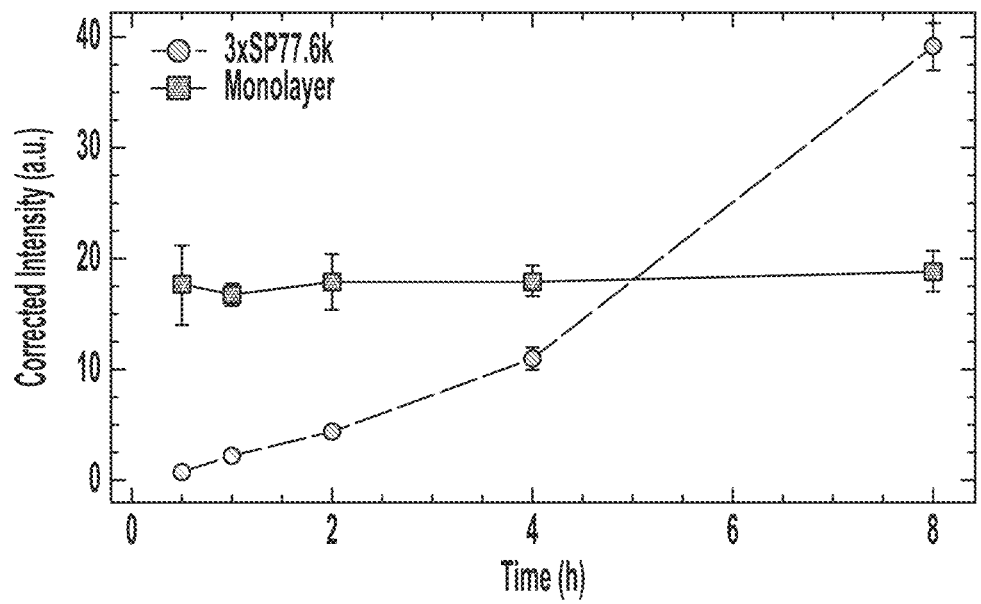
FIGS. 23A-23B. Fluorescent diffusion assays indicating the diffusion of streptavidin (SA) and monomeric streptavidin variant (mSA2) into bioconjugate thin films over time. The thin film was either 170 nm thick and exposed to a 10 µM solution SA (FIG. 23A) or the thin film was 166 nm thick and exposed to an 800 nM solution of mSA2 (FIG. 23B). Results are compared to those obtained using a rcSso7d. SA monolayer. Error bars represent the standard deviation of three replicates.
Figure 23B:
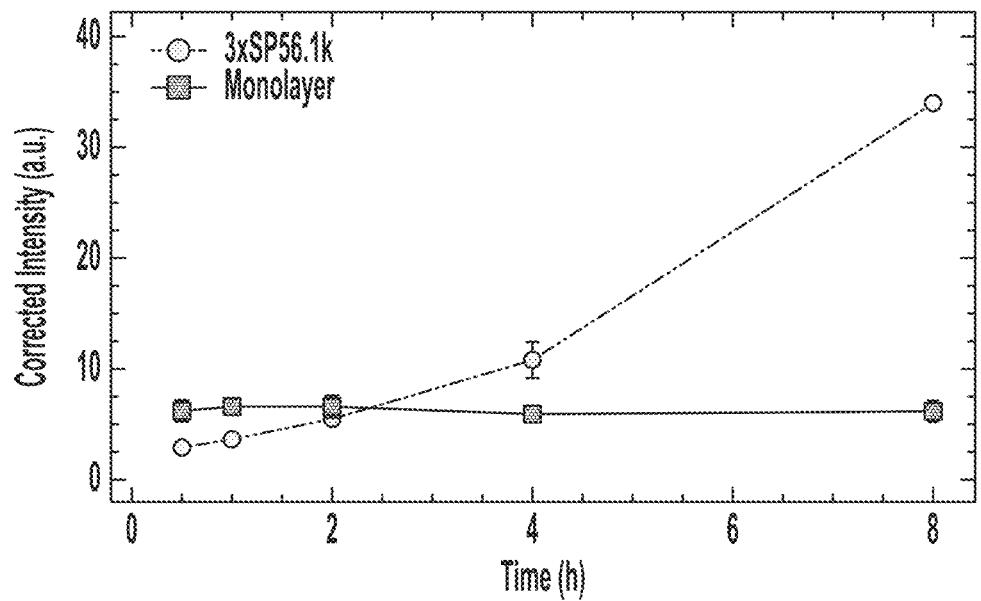
Figure 24A:
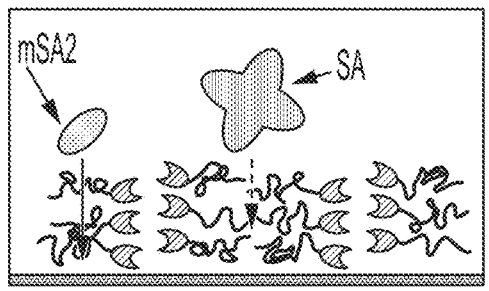
FIGS. 24A-24B. Diagram of SA and mSA2 diffusion into 3×SP conjugate thin films with a small domain spacing (FIG. 24A) and a larger domain spacing (FIG. 24B). Solid arrows represent relatively quick diffusion into the film, while dashed arrows represent greatly restricted diffusion.
Figure 24B:
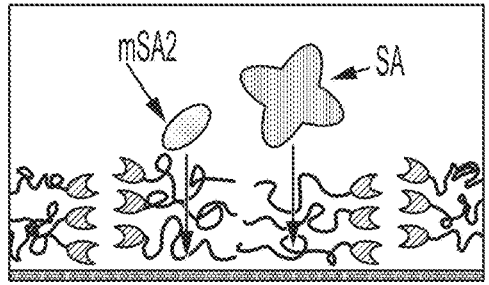
Figure 34:
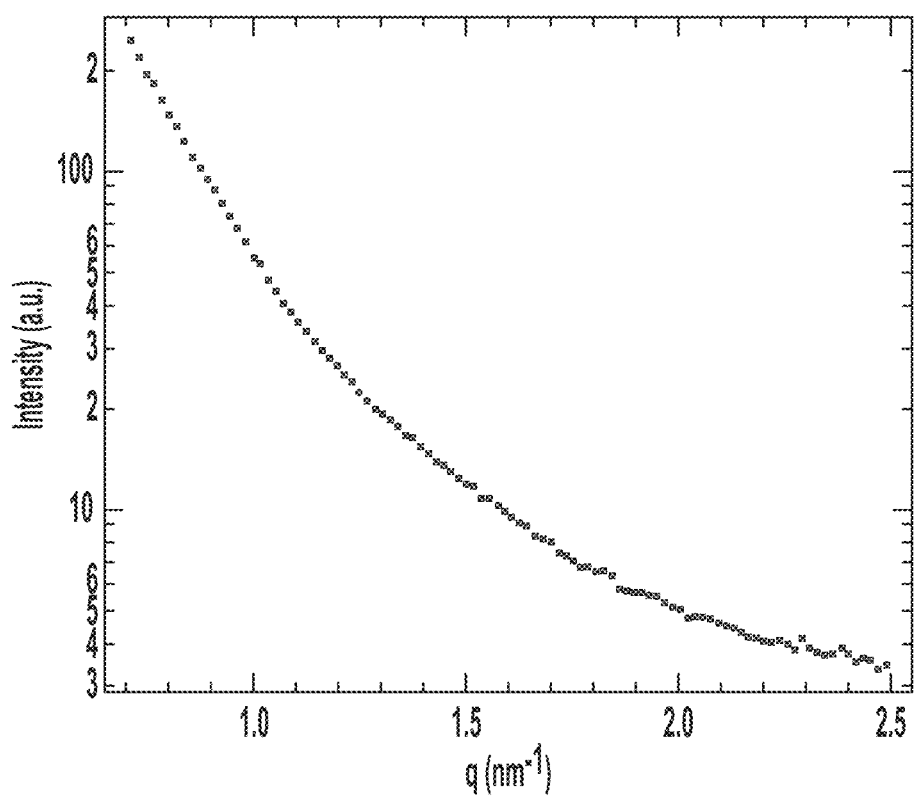
FIG. 34. Representative GISAXS vertical linecut from swollen thin films. GISAXS pattern was collected from a 3×SP56.1k thin film at an incident angle of 0.140°.
Figure 36:
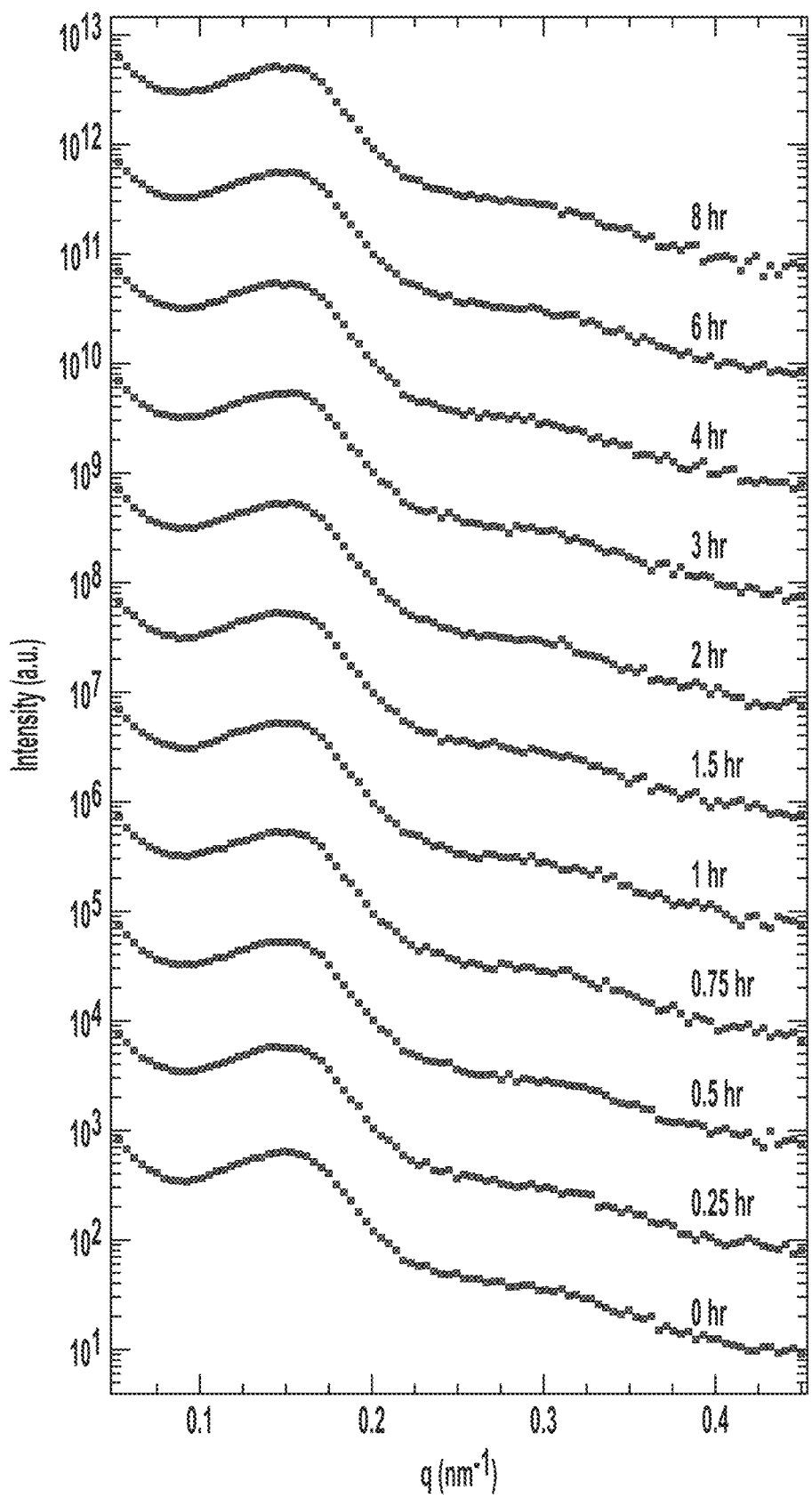
FIG. 36. GISAXS horizontal linecuts of a 150 nm 3×SP56.1k film swollen in an environment maintained at 95% RH for different periods of time. GISAXS patterns were collected at an incident angle of 0.140°.

Protein-polymer conjugate thin films were fabricated with a wide range of domain spacings to control diffusion into the films. Each conjugate was synthesized from a previously reported trimer of rcSso7d.SA,32 a modified DNA-binding protein with high binding affinities for streptavidin (SA)42 and a monomeric variant of streptavidin (mSA2),[83,81] conjugated to poly(N-isopropylacrylamide) (PNIPAM). Thin films created using these conjugates all adopted a weak lamellar morphology (FIG. 22) with domain spacings ranging from approximately 20 to 55 nm (Table 6) when swollen with water. Lamellar spacing was only observed in horizontal linecuts (FIG. 22), not in vertical linecuts (FIG. 34), suggesting that the lamellae adopted a predominantly perpendicular orientation. The film domain spacings were consistently larger than those measured in dry fluorescent intensity indicative of protein bound to the film. These experiments were also run using a monolayer of rcSso7d.SA immobilized onto a surface, allowing a direct comparison between the thin films and traditional surfaced-immobilized protein biosensors. Both SA and mSA2 displayed a continuous uptake into the ~170 nm films over at least 8 hours, whereas the monolayers were observed to equilibrate with the protein solution after 30 minutes (FIG. 23). Film structure and domain spacing were not found to change as a result of film swelling over an 8 hour time period (FIG. 36), suggesting that films remained stable throughout the experiment. It is worth noting that the film exposed to SA reached the same intensity observed in a monolayer after ~5 hours while the thin film exposed to mSA2 reached this intensity after only ~2.5 hours. These results are consistent with the idea that analyte size controls diffusion into these conjugate thin films. For a given domain spacing, a smaller molecule, such as mSA2, should experience less restricted diffusion into the films than a larger molecule, such as SA, due to the easier uptake of the smaller molecule into the polymer nanodomains (FIG. 24A). Similarly, all molecules would be expected to diffuse into the films more quickly as domain spacing increases (FIG. 24B). Because SA displayed slower uptake into the thin film than mSA2 (relative to a monolayer) despite being exposed to a film with a larger domain spacing, it appears analyte size does indeed affect uptake rate. Thus, even this initial experiment provided evidence that the larger SA molecule experienced greater resistance to diffusion into the bioconjugate films than mSA2.

Figure 25A:
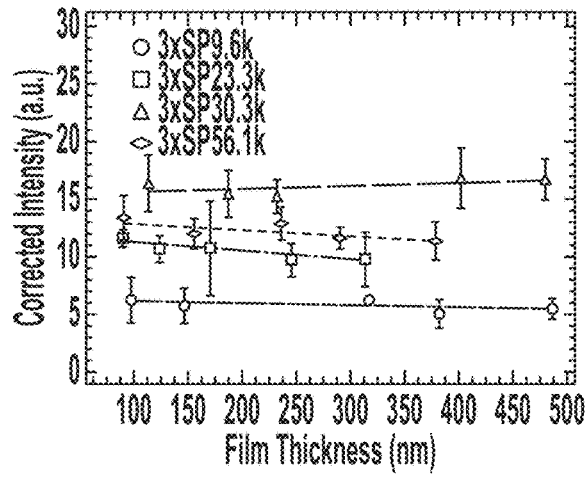
FIGS. 25A-25D. Results of 30 minute fluorescent binding assays performed in bioconjugate thin films using SA (FIGS. 25A, 25B) or (FIGS. 25C, 25D) mSA2 as the analyte. Graphs are divided to differentiate between films with low Mn PNIPAM and similar behavior (FIGS. 25A, 25C) and high Mn PNIPAM and similar behavior (FIGS. 25B, 25D). Lines in the figure are drawn to guide the eye. The films were exposed to a 4 µM solution of SA (FIGS. 25A, 25B) or mSA2 (FIGS. 25C, 25D). Error bars represent the standard deviation of three replicates.
Figure 25B:
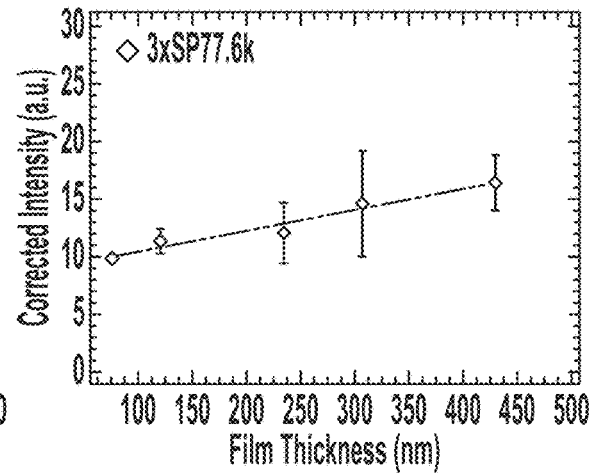

Larger domain spacings allowed faster diffusion into the thin films. Fluorescent assays were again run with both SA and mSA2, but films were exposed to protein solution for only 30 minutes to study diffusion into the thin films at early time points prior to saturation at equilibrium binding conditions. Fluorescent intensity remained constant with increasing film thickness for films with the smallest domain spacings when using SA as the analyte (FIG. 25A). This behavior suggests that SA is only able to diffuse a small distance (less than the thickness of the shortest thin film) into the films within 30 minutes, resulting in SA only binding in a region at the surface of each film. Only in thin films constructed from 3×SP77.6k, which had the largest domain spacing, was an increase in signal with film thickness observed when using SA as the analyte (FIG. 25B). In these films, SA is seemingly capable of diffusing through the entire thin film, causing this analyte to come into contact with and bind to more binding sites in thicker films. Because this less-restricted diffusion was only observed in the films with the largest domain spacing, these findings further support the idea that domain spacing controls diffusion into the films.

Figure 25C:
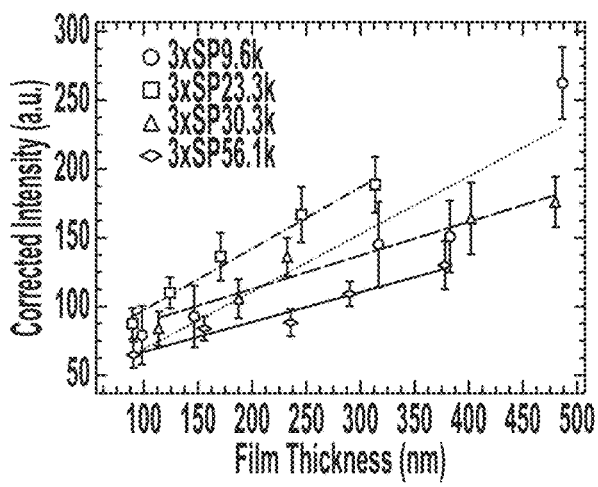
Figure 25D:
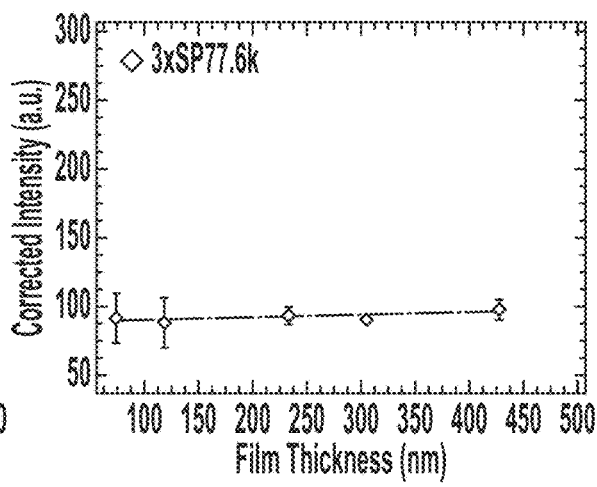

Film thickness measurements conducted using mSA2 as the analyte indicated that this smaller protein experienced less restricted diffusion into the thin films. In contrast to the constant intensity observed when using SA, films with the 4 smallest domain spacings all showed an increase in fluorescent intensity with film thickness (FIG. 25C). As such, analyte could fully access the binding sites within thin films with a significantly smaller domain spacing when mSA2 was used as the analyte (21.9 nm) than when SA was used (53.9 nm). Furthermore, when using mSA2 no change in signal with film thickness was found for 3×SP77.6k thin films (FIG. 25D). It is possible that, due to the significantly lower density of binding sites within the 3×SP77.6k films resulting from the low mass fraction of protein in this conjugate (Table 6), the greater intensity from increased mSA2 binding is difficult to detect. Indeed, only a very small increase in signal was observed with increasing film thickness when SA was added to these same thin films (FIG. 25B). On the whole, however, the different binding patterns when using mSA2 and SA strongly suggest that the smaller size of mSA2 permitted easier diffusion into the films.

Biosensing Capabilities

Sensing in Buffer.

To evaluate how the apparent size-based diffusion properties translated to biosensing capabilities, binding curves were measured using SA and mSA2 solutions in buffer. Binding curves were fit with a quadratic model that is a function of three parameters: the average MFI per binding event a, the total concentration of binding sites $[P]_T$, and the apparent dissociation constant $K_{d,app}$ describing the binding equilibrium between analyte and binding sites within the thin film. Best-fit values for these parameters are provided in Table 8. Nearly all independent fits gave 95% confidence intervals for a that contained the value 100 MFI/nM, demonstrating good self-consistency of the model. Limit of detection (LOD) was calculated as the concentration along the binding curve at which the measured intensity was three times the standard deviation of a blank sample measured on the same film.

TABLE 8

Best-fit Parameters for Buffer Binding Curves.

| Film | Thickness (nm) | $A^a$ (MFI/nM) | $[P]_T^a$ (nM) | $K_{d,\,app}$ (µM) |
|---|---|---|---|---|
| Streptavidin Films | | | | |
| Monolayer | — | 107 ± 8 | 0.36 ± 0.03 | 8 ± 2 |
| 3×SP9.6k, 0.5 h | 173 | 100 ± 10 | 0.08 ± 0.01 | 60 ± 10 |
| 3×SP9.6k, 4 h | 138 | 110 ± 20 | 0.9 ± 0.2 | 40 ± 10 |
| 3×SP77.6k, 0.5 h | 161 | 80 ± 50 | 0.3 ± 0.2 | 80 ± 60 |
| 3×SP77.6k, 4 h | 121 | 123 ± 6 | 0.41 ± 0.02 | 17 ± 2 |
| 3×SP77.6k, 8 h | 105 | 130 ± 20 | 0.64 ± 0.07 | 15 ± 4 |
| Monomeric Streptavidin Films | | | | |
| Monolayer | — | 100 ± 10 | 0.35 ± 0.05 | 3 ± 1 |
| 3×SP9.6k, 0.5 h | 165 | 114 ± 9 | 0.38 ± 0.03 | 11 ± 2 |
| 3×SP9.6k, 4 h | 138 | 100 ± 20 | 0.7 ± 0.1 | 3.7 ± 0.9 |
| 3×SP56.1k, 0.5 h | 202 | 129 ± 7 | 1.17 ± 0.06 | 33 ± 4 |
| 3×SP56.1k, 4 h | 140 | 80 ± 9 | 3.2 ± 0.4 | 16 ± 4 |
| 3×SP56.1k, 8 h | 133 | 90 ± 10 | 2.8 ± 0.4 | 13 ± 5 |

$^a$Reported errors represent 95% confidence intervals for the parameter estimate.

Figure 26A:
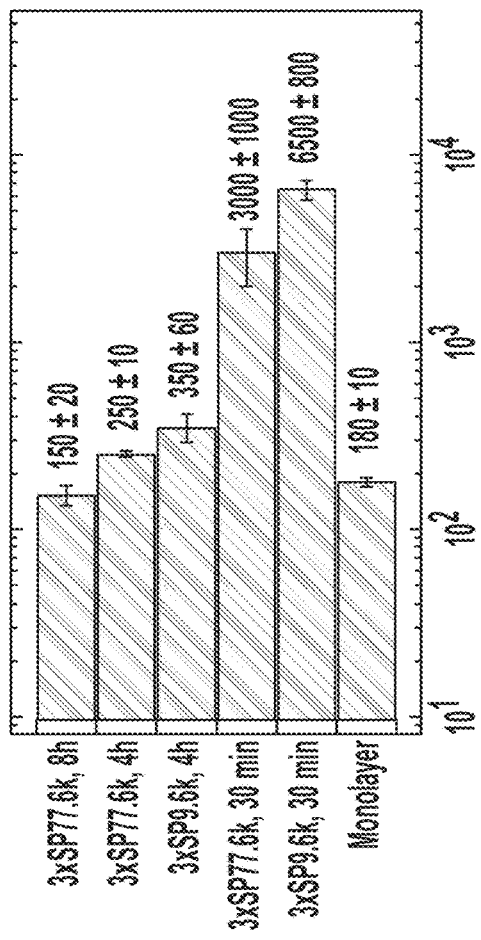
FIGS. 26A-26D. Binding curves for conjugate thin films exposed to SA (FIG. 26A) or mSA2 (FIG. 26C) in PBS for different periods of time. Results are compared to those obtained using a rcSso7d.SA monolayer with a 4 hour exposure time. The limit of detection determined for each binding curve is reported for films exposed to SA (FIG. 26B) or mSA2 (FIG. 26D). Film thicknesses are listed in Table 7. Error bars represent the standard deviation of three replicates.
Figure 26B:
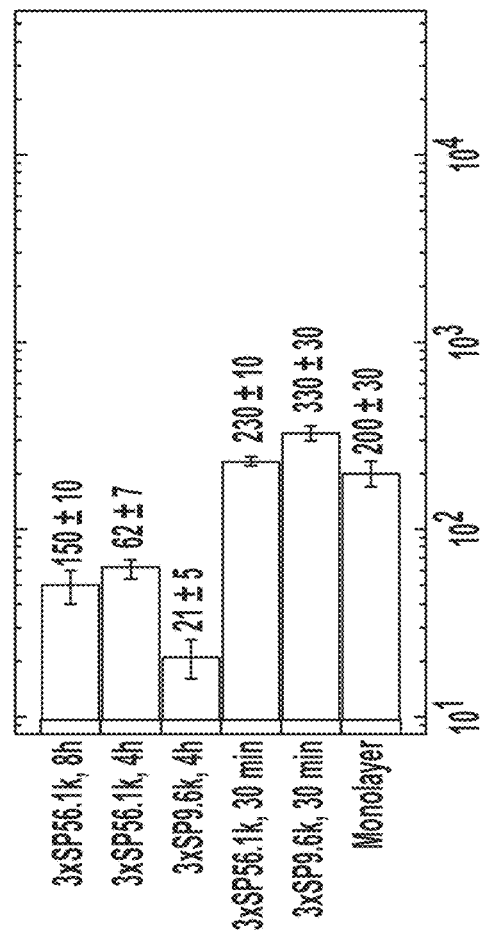

An rcSso7d.SA monolayer in general outperformed the 3×rcSso7d.SA-PNIPAM biosensor thin films when exposed to SA solutions (FIG. 26A). The sensitivity of films fabricated from conjugates with the smallest domain spacing (3×SP9.6k) was over an order of magnitude lower after 30 minutes of exposure and approximately 2-fold higher after 4 hours of exposure compared to a monolayer (FIG. 26B). These results are consistent with findings that 3×SP9.6k films significantly restricted SA diffusion (FIG. 25A). In contrast, 3×SP77.6k films that allowed much less restricted transport of SA (FIG. 25B) were found to approach the sensitivity of a monolayer after 4 hours and displayed slightly enhanced sensitivity after 8 hours, demonstrating the positive effect of enhanced SA diffusivity on device performance. This improved diffusivity in 3×SP77.6k films is best demonstrated by comparing the 30 minute data for the two conjugate films. Because the 3×SP77.6k film has a significantly lower density of binding sites than the 3×SP9.6k film, it would be expected that at equilibrium the 3×SP9.6k film would display a significantly stronger fluorescent signal. Since instead the 3×SP77.6k thin film shows a greater fluorescent intensity after 30 minutes (prior to reaching equilibrium), it is likely that SA has a greater diffusivity in this film, enabling the protein to penetrate further into the film within this short time frame. In fact, the binding curve fits reveal that nearly four times as many binding sites are accessed in the 3×SP77.6k film after 30 minutes, despite the lower total concentration of binding sites in this film (Table 8). Both films, though, demonstrate an increased number of accessible binding sites and $K_{d,app}$ value (that approaches but does not reach the monolayer value) over time. These observations are reasonable, as SA would be expected to further diffuse into the film over time, gradually accessing more binding sites and approaching the equilibrium value for bound analyte concentration. This slow approach to equilibrium binding conditions is also consistent with the finding that the thin films require significantly more time to saturate than a simple protein monolayer (FIG. 23A). Overall, these results indicate that compared to a monolayer, SA is largely excluded from the thin films due to reduced diffusivity, and the diffusion properties can be tuned by changing domain spacing.

Figure 26C:
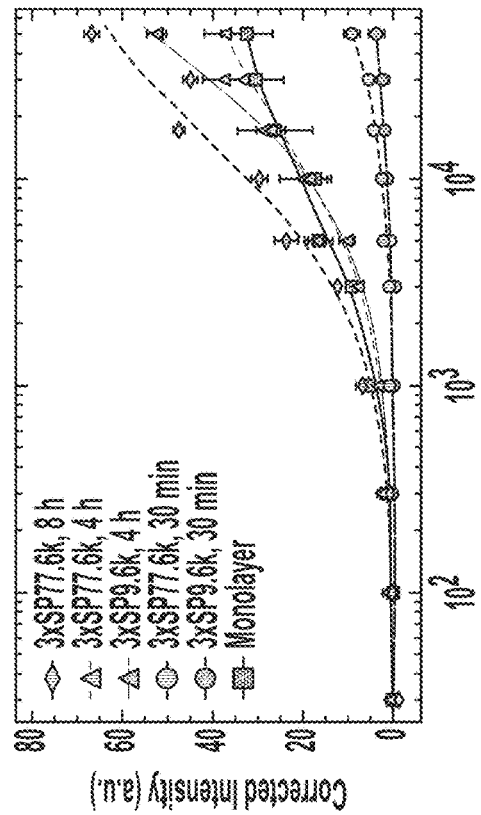
Figure 26D:
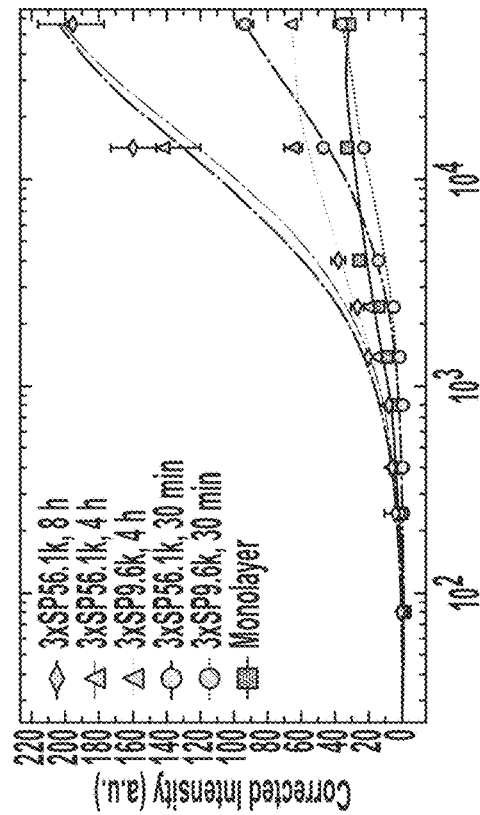

When using mSA2 as the analyte, the studied protein-polymer conjugate thin films displayed enhanced sensitivity compared to a protein monolayer. 3×SP9.6k films and 3×SP56.1k films were used to compare the biosensing capabilities of films that allowed complete mSA2 diffusion (FIG. 25C) but have a large difference in density of binding sites. While both films achieved a lower LOD than the rcSso7d.SA monolayer after 4 hours (FIGS. 26C, 26D), using the film with a smaller domain spacing (3×SP9.6k, 10-fold reduction in LOD) reduced the LOD more than using the film with the larger domain spacing (3×SP56.1k, ~4-fold reduction in LOD). As the opposite trend was found when using SA, mSA2 is likely small enough relative to the domain spacing in 3×SP9.6k films such that the reduction in diffusivity compared to that in 3×SP56.1k films is not large enough to overcome the sensitivity-enhancing effect of the greater density of binding sites. This effect, however, is not a result of mSA2 accessing more binding sites in the 3×SP9.6k film, as over four times the number of binding sites are accessible in the 3×SP56.1k films (Table 8). Instead, it appears that the enhanced sensitivity results from a lower $K_{d,app}$ value within then 3×SP9.6k film (Table 8), indicating that a greater fraction of mSA2 remains bound to these films. Thus, unlike when detecting SA, the thin film biosensors were able to effectively uptake and bind the smaller protein mSA2.

Sensing in Biological Fluids.

Figures 27E, 27F:
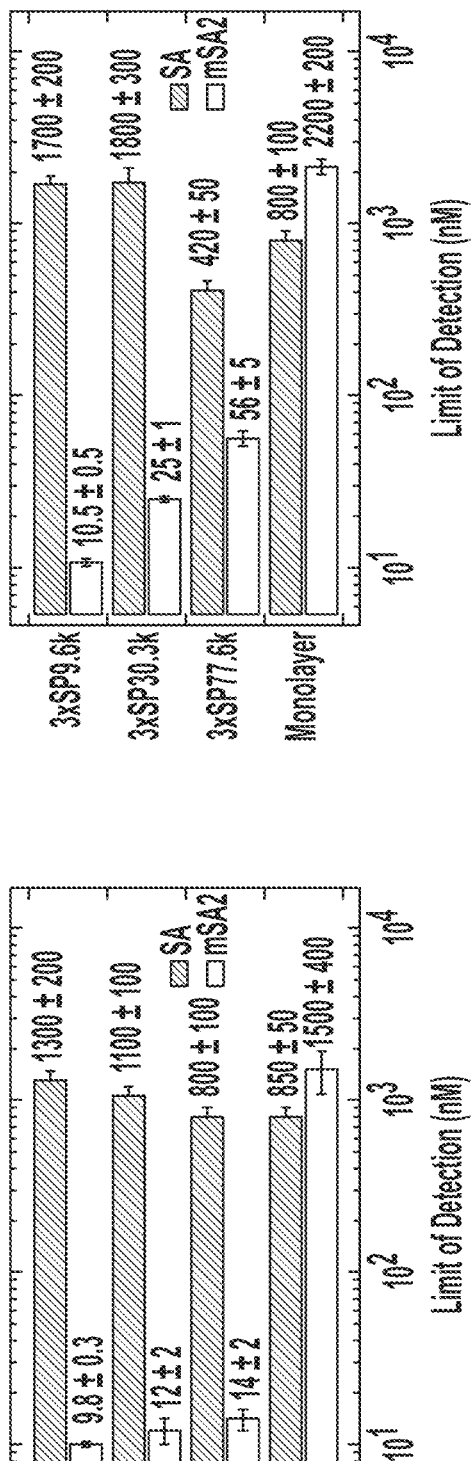

Binding curve measurements in blood serum and urine (both 50% diluted) demonstrated that the size-based exclusion properties of the conjugate thin films could enable enhanced selectivity in biological fluids. 3×SP9.6k, 3×SP30.3k, and 3×SP77.6k films were used for these experiments, allowing comparison of device sensitivity using a range of domain spacings. When detecting SA, the thin films in general performed comparably to a monolayer (FIGS. 27A, 27B). In both blood serum and urine, the monolayers and most thin film samples experienced an approximate 4 to 5-fold increase in LOD compared to measurements in buffer as a result of nonspecific binding from other molecules in the fluid (FIGS. 26B, 27E, 27F). Correspondingly, the binding events in each film could be described by a $K_{d,app}$ value ~4-5 times that of the monolayer value in buffer (Table 9). In fact, nearly all films were found to have the same concentration of accessible binding sites as a monolayer (Table 9), suggesting inaccessibility of most binding sites likely resulting from restriction of diffusion into the film. Additionally, the relationship between sensitivity and domain spacing mirrors that found in buffer, as 3×SP9.6k and 3×SP30.3k films greatly restrict SA diffusion and perform worse than the monolayer, while the 3×SP77.6k urine sample performance is indistinguishable from that of the monolayer. The one outlier to this trend is the 3×SP77.6k blood sample, which displays a near 2-fold reduction in LOD compared to the rcSso7d.SA monolayer (FIG. 27F). This enhanced performance may be attributable to the larger size of proteins in blood than in urine, enabling SA to diffuse into the thin films faster than a greater fraction of proteins in blood.

TABLE 9

Best-fit Parameters for Biological Matrix Binding Curves.

| Film | Thickness (nm) | $A^a$ (MFI/nM) | $[P]r^a$ (nM) | $K_{d,app}{}^a$ (µM) |
|---|---|---|---|---|
| Streptavidin Films (Urine) | | | | |
| Monolayer | — | 150 ± 10 | 0.29 ± 0.02 | 47 ± 5 |
| 3×SP9.6k | 142 | 80 ± 20 | 0.26 ± 0.05 | 30 ± 10 |
| 3×SP30.3k | 184 | 80 ± 20 | 0.27 ± 0.06 | 30 ± 10 |
| 3×SP77.6k | 154 | 160 ± 30 | 0.30 ± 0.06 | 50 ± 20 |
| Streptavidin Films (Blood) | | | | |
| Monolayer | — | 150 ± 20 | 0.28 ± 0.04 | 40 ± 10 |
| 3×SP9.6k | 123 | 90 ± 10 | 0.27 ± 0.04 | 50 ± 10 |
| 3×SP30.3k | 159 | 80 ± 20 | 0.23 ± 0.04 | 40 ± 10 |
| 3×SP77.6k | 133 | 120 ± 20 | 0.6 ± 0.1 | 40 ± 10 |
| Monomeric Streptavidin Films (Urine) | | | | |
| Monolayer | — | 119 ± 3 | 0.40 ± 0.01 | 50 ± 2 |
| 3×SP9.6k | 142 | 128 ± 5 | 17.0 ± 0.7 | 26 ± 2 |
| 3×SP30.3k | 184 | 120 ± 20 | 16 ± 2 | 29 ± 6 |
| 3×SP77.6k | 154 | 120 ± 10 | 15 ± 1 | 31 ± 5 |
| Monomeric Streptavidin Films (Blood) | | | | |
| Monolayer | — | 120 ± 10 | 0.40 ± 0.03 | 62 ± 7 |
| 3×SP9.6k | 123 | 97 ± 2 | 9.4 ± 0.2 | 12.2 ± 0.6 |
| 3×SP30.3k | 159 | 111 ± 4 | 5.7 ± 0.2 | 20 ± 1 |
| 3×SP77.6k | 133 | 110 ± 10 | 4.5 ± 0.5 | 35 ± 6 |

$^a$Reported errors represent 95% confidence intervals for the parameter estimate.

In the tested biological fluids, the small protein mSA2 could be detected with LOD values 2 orders of magnitude lower than those obtained when using a simple monolayer as the biosensor (FIGS. 27C-27F). Whereas the sensitivity of the monolayer in the fluids was up to an order of magnitude worse than in buffer, the thin films showed no change or slight improvement in sensitivity. The apparent improvement in thin film performance is likely a consequence of using slightly thicker films for the experiments performed in biological fluids (Table 9). Indeed, more binding sites were accessible in these samples than in those used for buffer experiments (Tables 8-9). $K_{d,app}$ values were also consistently lower in the thin films than in the monolayers, implying that less nonspecific binding occurred in the thin films due to the greater exclusion of proteins larger than mSA2 (Table 9). As expected, the $K_{d,app}$ values increased with increasing domain spacing, corresponding to more proteins being able to penetrate films with larger domain spacings. These findings further demonstrate that domain spacing can be tuned to allow selective uptake of small proteins.

Sensor Stability.

Figure 37A:
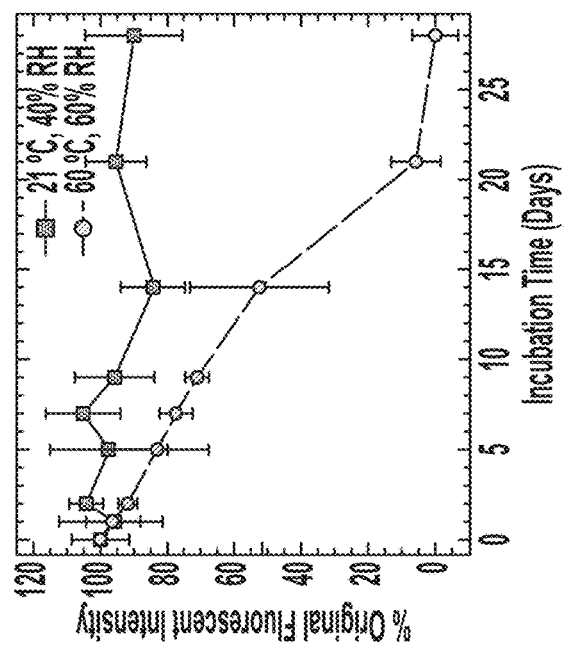
FIGS. 37A-37D. Retention of biosensing capabilities in 3×SP77.6k thin films under different temperature and humidity conditions (FIG. 37A). GISAXS horizontal linecuts of the films in FIG. 37A after 14 days show no significant change in structure (FIG. 37B). Full GISAXS patterns for films exposed to ambient conditions (FIG. 37C) and high temperature and high humidity (FIG. 37D) from which the linecuts in FIG. 37B were generated. All measurements were conducted on sections cut from the same 204 nm film. Films in FIG. 37A were exposed to 10 µM solutions of SA for 4 hours. GISAXS patterns were collected at an incident angle of 0.140°. Error bars in FIG. 37A represent the standard deviation of three replicates.
Figure 37B:
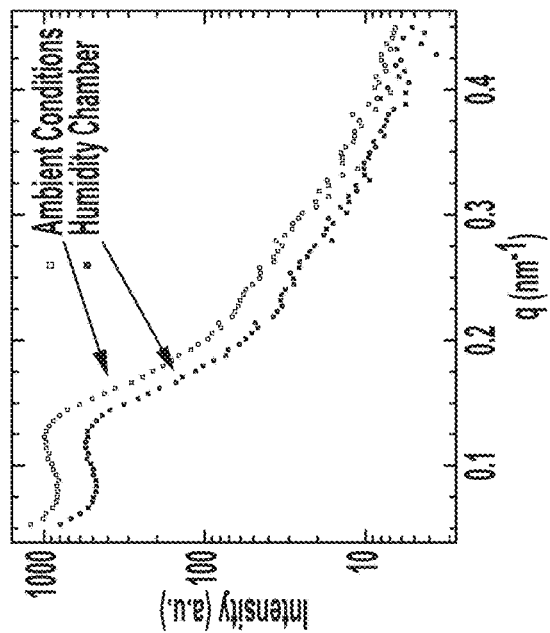
Figure 37C:
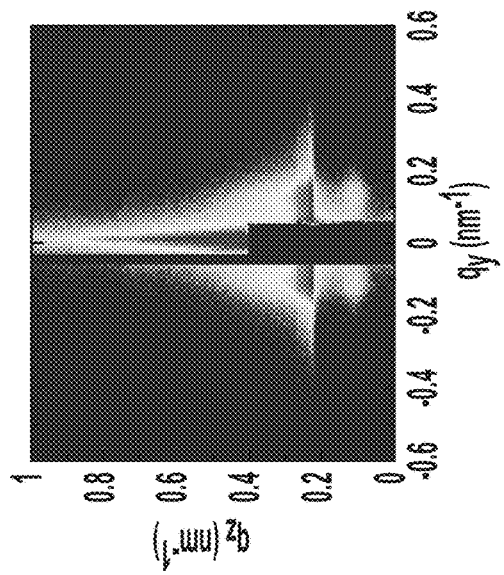
Figure 37D:
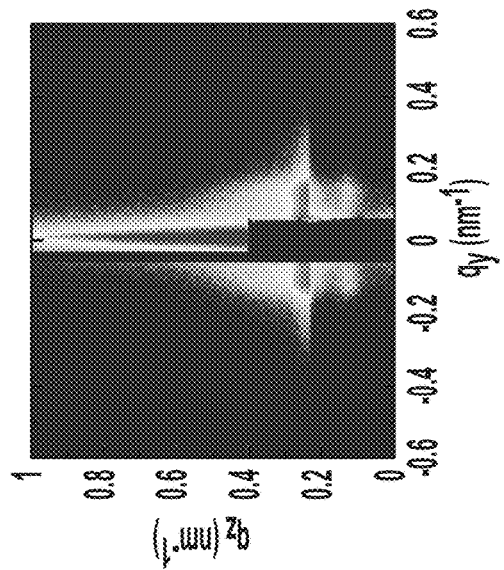

The developed protein-polymer conjugate thin films displayed excellent stability for a protein-based biosensor. When exposed to ambient conditions, films showed no significant decrease in binding capabilities over 4 weeks (FIG. 37A). Furthermore, when stored at 60° C. and 60% relative humidity, the films were still able to bind analyte to 50% of their original capacity after 2 weeks, only becoming completely inactive after 4 weeks. The exceptional temperature stability is unsurprising given that the rcSso7d.SA protein used as the molecular recognition element in these biosensors was engineered from a protein native to a hyperthermophilic microbe and was previously demonstrated to be resistant to extreme temperatures.[39] GISAXS linecuts indicated that no structural change had occurred in the films after 2 weeks (FIG. 37B), suggesting that the decrease in binding capability was the result of 3×rcSso7d.SA denaturing without causing microstructural rearrangement.

Sandwich Assay Demonstration

Figure 28:
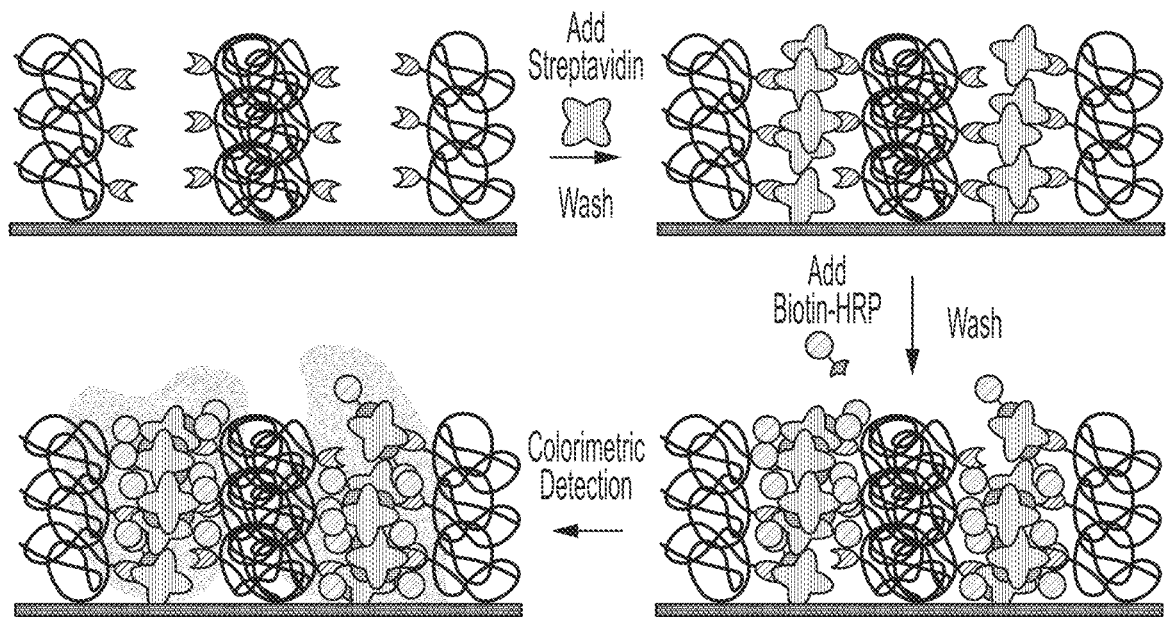
FIG. 28. Schematic of model sandwich assay performed in conjugate thin film biosensors.
Figure 38B:
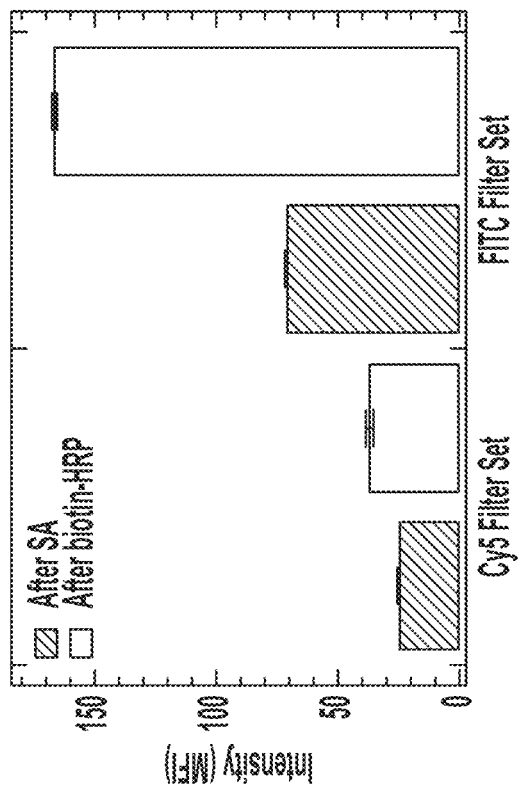
FIGS. 38A-38B Results of sequential fluorescent binding assays using mSA2 (FIG. 38A) and SA (FIG. 38B) as the analyte. Error bars represent the standard deviation of three replicates. 150 nm 3×SP77.6k thin films were exposed for 4 hours to solutions of either mSA2 or SA (fluorescently labeled with Alexa Fluor 647; similar emission and excitation maxima as Cy5), each with a concentration of 10 and imaged using Cy5 and FITC filter sets (boxes filled with diagonal lines). Films were then exposed to a 200 ng/mL solution of biotin-HRP (fluorescently labeled with Alexa Fluor 488; similar emission and excitation maxima as FITC) for 4 hours and again imaged using Cy5 and FITC filter sets (solid boxes). While the film exposed to SA showed significant biotin-HRP binding, almost no biotin-HRP was bound to the film exposed to mSA2. The slight increase in fluorescent signal in the Cy5 filter channel after biotin-HRP binding in FIG. 38B is likely due to slight overlap of the Cy5 filter set emission and excitation wavelengths with the emission and excitation spectra for Alexa Fluor 488.
Figure 38A:
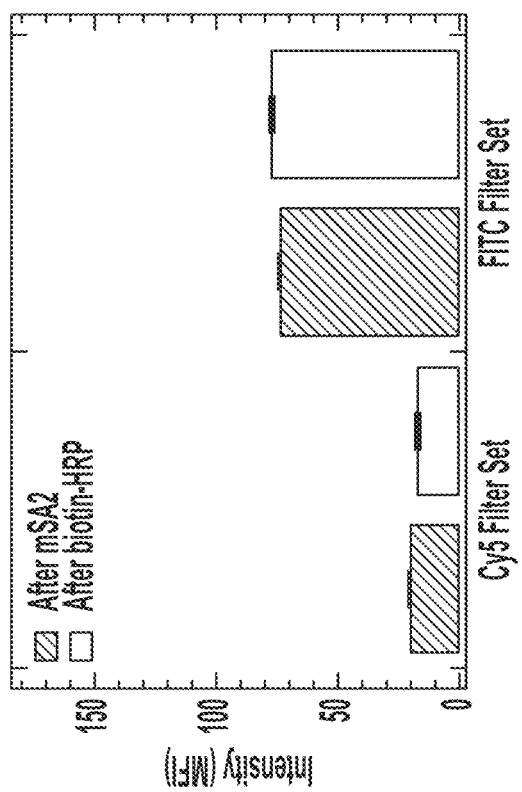

To demonstrate that the thin film biosensors could be used in detection formats beyond simple imaging of fluorescently-labeled analytes, model sandwich assays were performed in the films. Specifically, these tests were designed to demonstrate the feasibility of using the films for multi-step detection assays such as a sandwich ELISA. The general procedure for this proof-of-concept experiment is diagrammed in FIG. 28. Films were first exposed to SA solutions and rinsed to remove unbound analyte. Taking advantage of the strong interaction between SA and biotin, thin films were then submerged in a solution of biotinylated horseradish peroxidase (biotin-HRP). Bound SA was detected colorimetrically through the HRP-mediated oxidation of 3,3',5,5'-tetramethylbenzidine (TMB). Attempts to perform this assay using mSA2 as the analyte were unsuccessful, even when run on an rcSso7d.SA monolayer. Binding experiments with fluorescently-labeled biotin-HRP revealed extremely weak binding between biotin and mSA2 (FIG. 38), which is consistent with previous reports of the biotin-mSA2 dissociation constant being multiple orders of magnitude greater than that for biotin and streptavidin.

Figure 29:
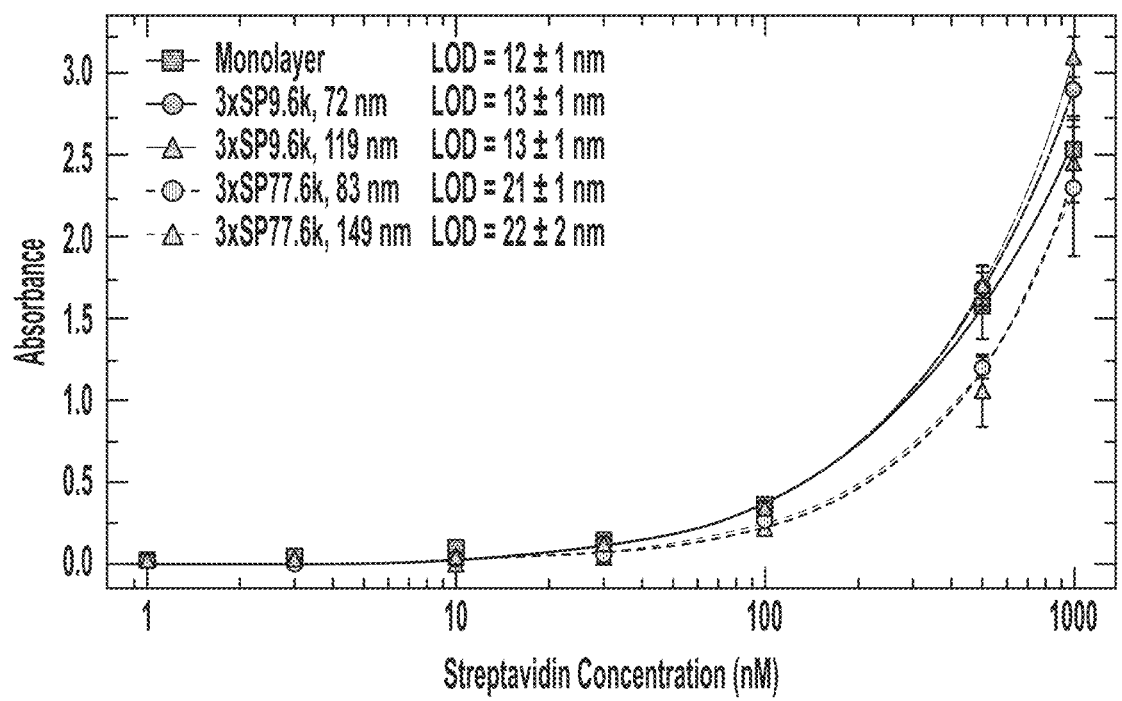
FIG. 29. Binding curves for sandwich assays performed with SA in PBS. Error bars represent the standard deviation of three replicates.
Figure 30:
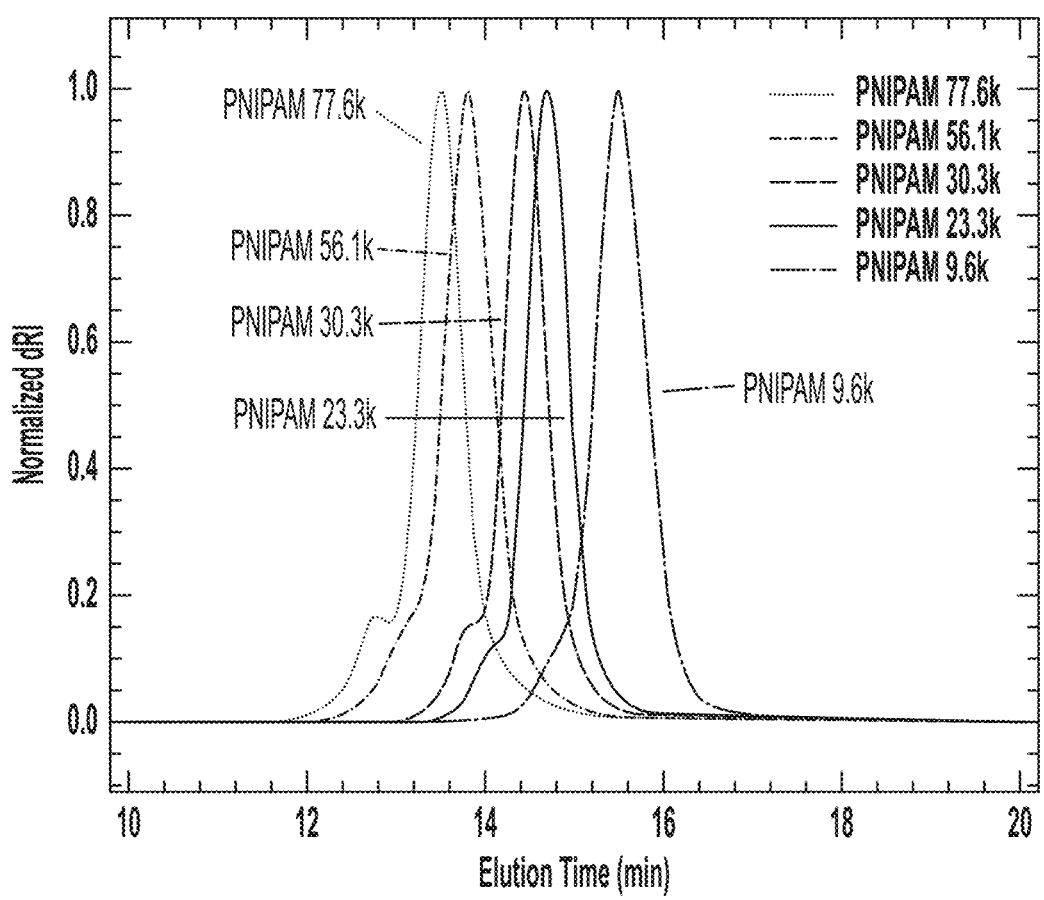
FIG. 30. Normalized differential refractive index signals from gel permeation chromatography of PNIPAM samples. The small shoulder at earlier elution times corresponding to twice the peak molecular weight in some samples results from slight reactivity of the double bond in the furan-protected maleimide of the CTA, as reported previously (Thomas, C. S.; Glassman, M. J.; Olsen, B. D., Solid-State Nanostructured Materials from Self-Assembly of a Globular Protein—Polymer Diblock Copolymer. ACS Nano 2011, 5 (7), 5697-5707, DOI: 10.1021/nn2013673).
Figure 31A:
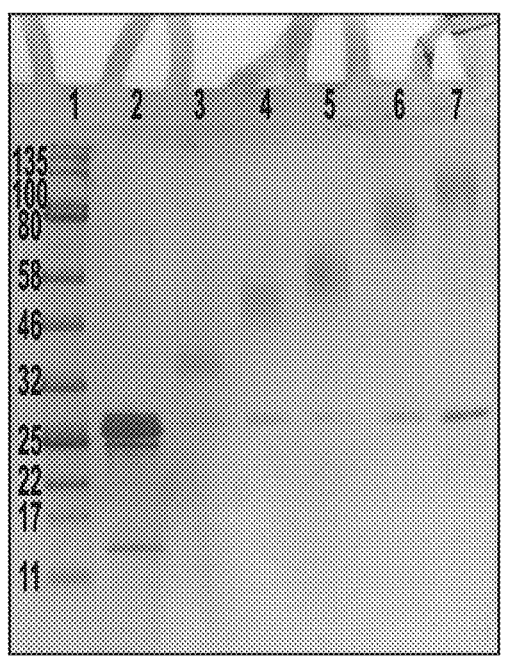
FIGS. 31A-31B. Denaturing protein gels of 3×rcSso7d.SA (FIG. 31A) and bioconjugates, and native protein gel of bioconjugates (FIG. 31B). Lanes 1-7 in FIG. 31A represent ladder, 3×rcSso7d.SA, 3×SP9.6k, 3×SP23.3k, 3×SP30.3k, 3×SP56.1k, 3×SP77.6k, respectively. Lanes 1-6 in FIG. 31B represent ladder, 3×SP9.6k, 3×SP23.3k, 3×SP30.3k, 3×SP56.1k, 3×SP77.6k, respectively. All ladders represent molecular weight in kDa. Minor impurities in denaturing gel are primarily the result of hydrolysis of an ester linkage between protein and PNIPAM during heating of samples; integration of the bands in native gel reveals that all conjugate samples are >90% pure.
Figure 31B:
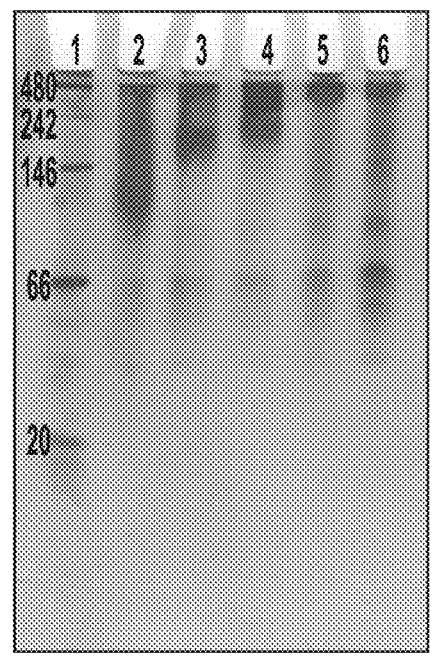
Figure 32B:
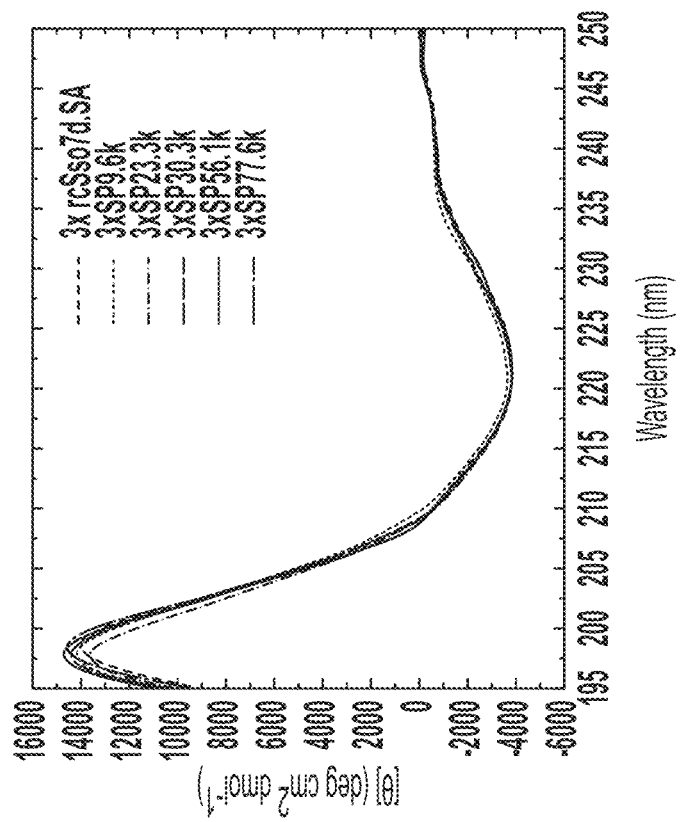
FIGS. 32A-32B. Circular dichroism spectroscopy of 3×SP30.3k before dehydration and after rehydration of solid conjugate pellets (FIG. 32A) and 3×rcSso7d.SA and all bioconjugates used in this study confirm minimal change in protein secondary structure (FIG. 32B). Results in FIG. 32A are representative of all conjugates. Slight differences between CD spectra of conjugates in FIG. 32B below 205 nm are primarily due to high noise in the CD spectrometer at these wavelengths.
Figure 32A:
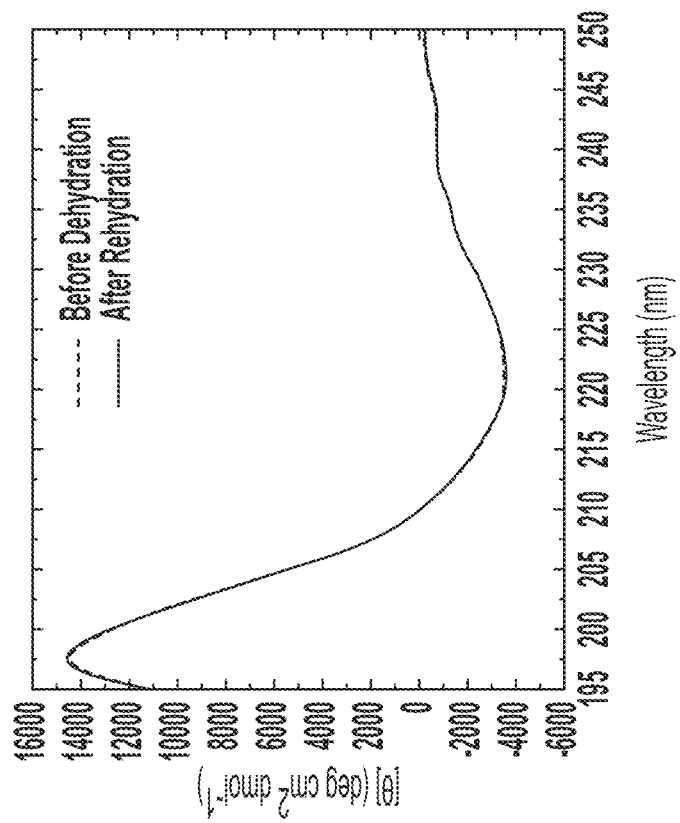

When SA was applied to the bioconjugate films in buffer, the films generally performed as well as a monolayer (FIG. 29). In contrast to the findings using fluorescent assays, 3×SP9.6k films achieved essentially the same LOD as an rcSso7d.SA monolayer, while the LOD attained with 3×SP77.6k films was nearly twice as large. LOD was also found to be effectively independent of film thickness, giving a sensitivity that only varied based on the conjugate used to fabricate the film. Together, these results suggest that detection only occurred within a thin layer at the film surface. If diffusion limitations were significant enough to restrict analyte access to the majority of the film volume, the absorbance in 3×SP77.6k films would be predicted to consistently be less than that in 3×SP9.6k films due to the lower fraction of binding sites in the former films (Table 6). This expectation is consistent with experimental observations and is reasonable when considering that in these experiments, HRP was also required to diffuse into the films to observe a signal. The relatively large size of HRP (44 kDa) combined with likely steric hindrance from SA molecules bound to the film may have resulted in restrictions to diffusion greater than in one-step fluorescent binding assays.

Figure 39B:
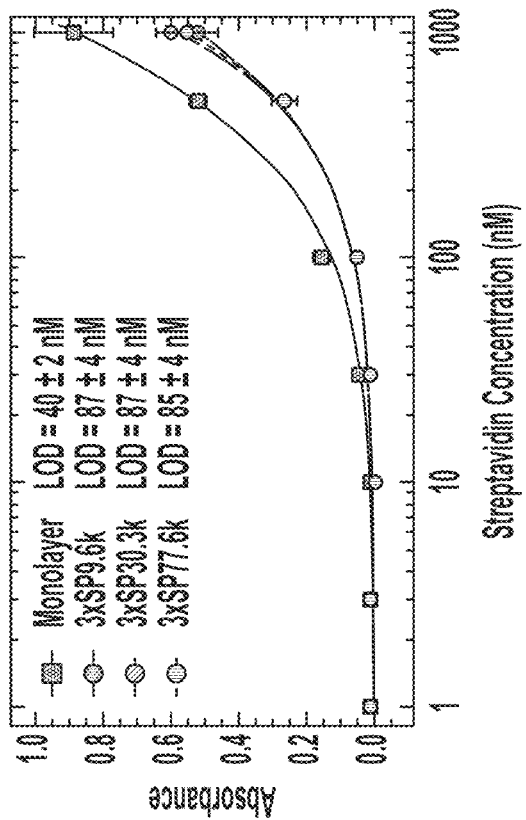
FIGS. 39A-39B. Binding curves for sandwich assays performed with SA in 50% urine (FIG. 39A) and 50% blood serum (FIG. 39B). Error bars represent the standard deviation of three replicates.
Figure 39A:
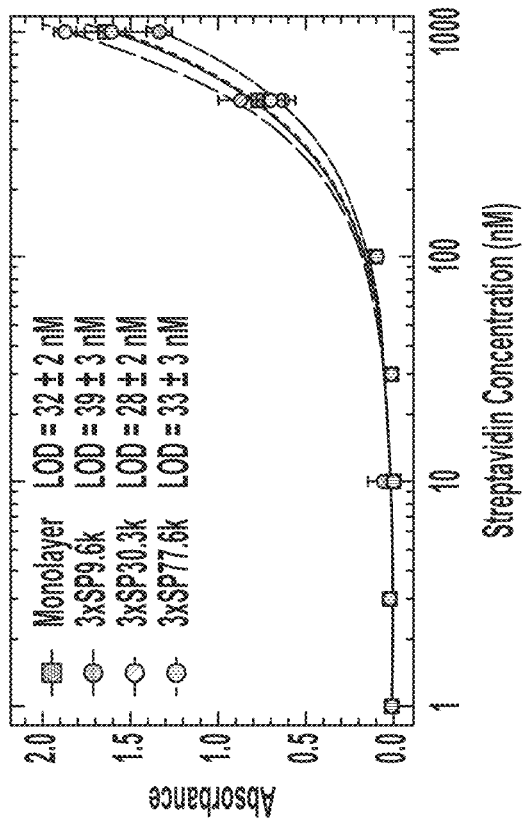

Sandwich assays exposed to SA in urine and blood serum gave similar results to those found using fluorescent assays. As was observed in the fluorescent assays (FIG. 27A), LODs for all tested thin films were similar to that of a monolayer when SA was dissolved in 50% urine (FIG. 39A). For SA samples in 50% blood serum, the LOD values for 3×SP9.6k and 3×SP30.3k films were 2-fold greater than that for an rcSso7d.SA monolayer (FIG. 39B), again mirroring results for the fluorescent assays (FIG. 35B). Unlike the fluorescent assays, however, for which 3×SP77.6k films were found to give a slight improvement in LOD, these same films resulted in a 2-fold greater LOD than a monolayer in the sandwich assays, possibly due to additional diffusion limitations for HRP. Though sandwich assay experiments could not be performed using mSA2 as the analyte, the general similarities between findings for fluorescent and sandwich assays suggest that sandwich assays with a smaller analyte would yield improved LOD values relative to a monolayer. Regardless, model sandwich assays using SA still demonstrate that these assays are feasible in the fabricated conjugate thin films.

CONCLUSIONS

The oligomerization of the low molecular weight protein rcSso7d.SA in protein-polymer conjugates is demonstrated to significantly improve the concentrated solution self-assembly in these materials. Block copolymers containing oligomerized rcSso7d.SA connected with flexible peptide sequences as a protein block display long-range lamellar ordering that is strongest in trimer and tetramer conjugates. All oligomer conjugates also show improved ordering quality relative to previously-studied protein-polymer block copolymers, suggesting that the greater flexibility of the protein block due to the addition of flexible linkers promotes more efficient packing within the protein domains. In highly concentrated solution, the studied conjugates assemble into weakly-ordered lamellae and display domain spacings that vary non-monotonically across the studied concentration range.

Thin films of the rcSso7d.SA oligomer conjugates are also found to function as highly sensitive biosensors, retaining binding capabilities and providing up to threefold decreases in limit of detection compared to traditionally-used protein monolayers. In general, oligomerization is observed to lower the limit of detection by increasing density of binding sites, but some evidence suggests too high protein densities result in inaccessibility of some sites. Despite not containing fully-accessible binding sites, the protein-polymer conjugate thin film biosensors are estimated to contain a 100-fold greater density of accessible sites within a single plane of conjugates than an rcSso7d.SA monolayer. By identifying a strategy that both improves ordering in low molecular weight protein-polymer conjugates and enables the development of more sensitive biosensors, this work provides a substantial framework for future research in protein design for both fundamental understanding of protein-polymer conjugate self-assembly and biosensing applications.

3×rcSso7d.SA-PNIPAM thin films display an apparent size-based diffusional resistance for proteins entering the film. Experiments performed with both mSA2 and the larger protein SA reveal that SA experiences greater resistance to diffusion into the films. In all cases, SA either demonstrates a longer timescale for diffusion into the thin films or requires films with larger domain spacings to allow appreciable uptake. By varying the molecular weight of the polymer block in the protein-polymer conjugates used to create the thin films, domain spacing can be adjusted to tune the size of proteins that the films could uptake. This simple tuning method should allow facile design of biosensors optimized for uptake of a target analyte.

The size-based uptake properties of the bioconjugate thin films are also found to enable greatly enhanced biosensor performance in biological fluids. Not only do these films achieve an LOD an order of magnitude lower than that of a traditional surface-immobilized protein biosensor in buffer, but the LOD is also found to be up to 2 orders of magnitude lower for detection in biological fluids due to minimization of nonspecific binding events. Model sandwich assays performed in the thin films generally match results in fluorescent binding assays, demonstrating potential for application in a variety of detection formats. With their easily tunable structure and highly sensitive detection capabilities, the designed protein-polymer conjugate thin films represent an extremely promising technology for detection of small proteins and peptides in biological matrices.

REFERENCES

1. Bahadir, E. B.; Sezgintürk, M. K., Lateral flow assays: Principles, designs and labels. *TrAC, Trends Anal. Chem.* 2016, 82, 286-306, DOI: 10.1016/j.trac.2016.06.006

2. Li, J.; Macdonald, J., Multiplexed lateral flow biosensors: Technological advances for radically improving point-of-care diagnoses. *Biosens. Bioelectron.* 2016, 83, 177-192, DOI: 10.1016/j.bios. 2016.04.021
3. Quesada-Gonzalez, D.; Merkoci, A., Nanoparticle-based lateral flow biosensors. *Biosens. Bioelectron.* 2015, 73, 47-63, DOI: 10.1016/j.bios. 2015.05.050
4. Sajid, M.; Kawde, A.-N.; Daud, M., Designs, formats and applications of lateral flow assay: A literature review. *J. Saudi Chem. Soc.* 2015, 19 (6), 689-705, DOI: 10.1016/j.jscs. 2014.09.001
5. Yetisen, A. K.; Akram, M. S.; Lowe, C. R., Paper-based microfluidic point-of-care diagnostic devices. *Lab Chip* 2013, 13 (12), 2210-2251, DOI: 10.1039/C3LC50169H
6. Yang, H.; Gijs, M. A. M., Micro-optics for microfluidic analytical applications. *Chem. Soc. Rev.* 2018, 47 (4), 1391-1458, DOI: 10.1039/C5CS00649J
7. Myers, F. B.; Lee, L. P., Innovations in optical microfluidic technologies for point-of-care diagnostics. *Lab Chip* 2008, 8 (12), 2015-2031, DOI: 10.1039/B812343H
8. Kim, D.; Herr, A. E., Protein immobilization techniques for microfluidic assays. *Biomicrofluidics* 2013, 7 (4), 041501, DOI: 10.1063/1.4816934
9. Ling, M. M.; Ricks, C.; Lea, P., Multiplexing molecular diagnostics and immunoassays using emerging microarray technologies. *Expert Rev. Mol. Diagn.* 2007, 7 (1), 87-98, DOI: 10.1586/14737159.7.1.87
10. Chandra, P. E.; Sokolove, J.; Hipp, B. G.; Lindstrom, T. M.; Elder, J. T.; Reveille, J. D.; Eberl, H.; Klause, U.; Robinson, W. H., Novel multiplex technology for diagnostic characterization of rheumatoid arthritis. *Arthrit. Res. Ther.* 2011, 13 (3), R102, DOI: 10.1186/ar3383
11. Cracknell, J. A.; Vincent, K. A.; Armstrong, F. A., Enzymes as Working or Inspirational Electrocatalysts for Fuel Cells and Electrolysis. *Chem. Rev.* 2008, 108 (7), 2439-2461, DOI: 10.1021/cr0680639
12. Makaraviciute, A.; Ramanaviciene, A., Site-directed antibody immobilization techniques for immunosensors. *Biosens. Bioelectron.* 2013, 50 (Supplement C), 460-471, DOI: 10.1016/j.bios. 2013.06.060
13. Squires, T. M.; Messinger, R. J.; Manalis, S. R., Making it stick: convection, reaction and diffusion in surface-based biosensors. *Nat. Biotechnol.* 2008, 26 (4), 417-426, DOI: 10.1038/nbt1388
14. Ho, J.-a. A.; Hsu, W.-L.; Liao, W.-C.; Chiu, J.-K.; Chen, M.-L.; Chang, H.-C.; Li, C.-C., Ultrasensitive electrochemical detection of biotin using electrically addressable site-oriented antibody immobilization approach via aminophenyl boronic acid. *Biosens. Bioelectron.* 2010, 26 (3), 1021-1027, DOI: 10.1016/j.bios. 2010.08.048
15. Peluso, P.; Wilson, D. S.; Do, D.; Tran, H.; Venkatasubbaiah, M.; Quincy, D.; Heidecker, B.; Poindexter, K.; Tolani, N.; Phelan, M.; Witte, K.; Jung, L. S.; Wagner, P.; Nock, S., Optimizing antibody immobilization strategies for the construction of protein microarrays. *Anal. Biochem.* 2003, 312 (2), 113-124, DOI: 10.1016/S0003-2697(02)00442-6
16. Boozer, C.; Ladd, J.; Chen, S.; Jiang, S., DNA-Directed Protein Immobilization for Simultaneous Detection of Multiple Analytes by Surface Plasmon Resonance Biosensor. *Anal. Chem.* 2006, 78 (5), 1515-1519, DOI: 10.1021/ac0519231
17. Naal, Z.; Park, J. H.; Bernhard, S.; Shapleigh, J. P.; Batt, C. A.; Abrulia, H. D., Amperometric TNT Biosensor Based on the Oriented Immobilization of a Nitroreductase Maltose Binding Protein Fusion. *Anal. Chem.* 2002, 74 (1), 140-148, DOI: 10.1021/ac010596o
18. Miller, E. A.; Baniya, S.; Osorio, D.; Al Maalouf, Y. J.; Sikes, H. D., Paper-based diagnostics in the antigen-depletion regime: High-density immobilization of rcSso7d-cellulose-binding domain fusion proteins for efficient target capture. *Biosens. Bioelectron.* 2018, 102, 456-463, DOI: 10.1016/j.bios. 2017.11.050
19. Sinem, E.; Dagmar, F.; Doris, W.; Ljiljana, F., SNAP-tag as a Tool for Surface Immobilization. *Curr. Pharm. Des.* 2013, 19 (30), 5443-5448, DOI: 10.2174/13816128113199300015
20. Wasserberg, D.; Cabanas-Danes, J.; Prangsma, J.; O'Mahony, S.; Cazade, P.-A.; Tromp, E.; Blum, C.; Thompson, D.; Huskens, J.; Subramaniam, V.; Jonkheijm, P., Controlling Protein Surface Orientation by Strategic Placement of Oligo-Histidine Tags. *ACS Nano* 2017, 11 (9), 9068-9083, DOI: 10.1021/acsnano. 7b03717
21. Thomas, C. S.; Glassman, M. J.; Olsen, B. D., Solid-State Nanostructured Materials from Self-Assembly of a Globular Protein—Polymer Diblock Copolymer. *ACS Nano* 2011, 5 (7), 5697-5707, DOI: 10.1021/nn2013673
22. Thomas, C. S.; Xu, L.; Olsen, B. D., Kinetically Controlled Nanostructure Formation in Self-Assembled Globular Protein—Polymer Diblock Copolymers. *Biomacromolecules* 2012, 13 (9), 2781-2792, DOI: 10.1021/bm300763x
23. Lam, C. N.; Olsen, B. D., Phase transitions in concentrated solution self-assembly of globular protein-polymer block copolymers. *Soft Matter* 2013, 9 (8), 2393-2402, DOI: 10.1039/C2SM27459K
24. Thomas, C. S.; Olsen, B. D., Coil fraction-dependent phase behaviour of a model globular protein-polymer diblock copolymer. *Soft Matter* 2014, 10 (17), 3093-3102, DOI: 10.1039/C3SM52531G
25. Chang, D.; Lam, C. N.; Tang, S.; Olsen, B. D., Effect of polymer chemistry on globular protein-polymer block copolymer self-assembly. *Polymer Chemistry* 2014, 5 (17), 4884-4895, DOI: 10.1039/C4PY00448E
26. Huang, C.-I.; Lodge, T. P., Self-Consistent Calculations of Block Copolymer Solution Phase Behavior. *Macromolecules* 1998, 31 (11), 3556-3565, DOI: 10.1021/ma980007p
27. Qin, G.; Glassman, M. J.; Lam, C. N.; Chang, D.; Schaible, E.; Hexemer, A.; Olsen, B. D., Topological Effects on Globular Protein-ELP Fusion Block Copolymer Self-Assembly. *Adv. Funct. Mater.* 2015, 25 (5), 729-738, DOI: 10.1002/adfm. 201403453
28. Lam, C. N.; Kim, M.; Thomas, C. S.; Chang, D.; Sanoja, G. E.; Okwara, C. U.; Olsen, B. D., The Nature of Protein Interactions Governing Globular Protein—Polymer Block Copolymer Self-Assembly. *Biomacromolecules* 2014, 15 (4), 1248-1258, DOI: 10.1021/bm401817p
29. Lam, C. N.; Yao, H.; Olsen, B. D., The Effect of Protein Electrostatic Interactions on Globular Protein—Polymer Block Copolymer Self-Assembly. *Biomacromolecules* 2016, 17 (9), 2820-2829, DOI: 10.1021/acs.biomac. 6b00522
30. Huang, A.; Qin, G.; Olsen, B. D., Highly Active Biocatalytic Coatings from Protein-Polymer Diblock Copolymers. *ACS Appl. Mater. Interfaces* 2015, 7 (27), 14660-14669, DOI: 10.1021/acsami. 5b01884
31. Dong, X. H.; Obermeyer, A. C.; Olsen, B. D., Three-Dimensional Ordered Antibody Arrays Through Self-Assembly of Antibody—Polymer Conjugates. *Angew. Chem. Int. Ed.* 2017, 56 (5), 1273-1277, DOI: 10.1002/anie. 201607085
32. Hassanzadeh-Ghassabeh, G.; Devoogdt, N.; Pauw, P. D.; Vincke, C.; Muyldermans, S., Nanobodies and their 33. Wang, H.; Li, G.; Zhang, Y.; Zhu, M.; Ma, H.; Du, B.; Wei, Q.; Wan, Y., Nanobody-Based Electrochemical Immunoassay for Ultrasensitive Determination of Apolipoprotein-A1 Using Silver Nanoparticles Loaded Nanohydroxyapatite as Label. *Anal. Chem.* 2015, 87 (22), 11209-11214, DOI: 10.1021/acs.analchem. 5b04063
34. Li, H.; Sun, Y.; Elseviers, J.; Muyldermans, S.; Liu, S.; Wan, Y., A nanobody-based electrochemiluminescent immunosensor for sensitive detection of human procalcitonin. *Analyst* 2014, 139 (15), 3718-3721, DOI: 10.1039/C4AN00626G
35. Renberg, B.; Nordin, J.; Merca, A.; Uhlén, M.; Feldwisch, J.; Nygren, P.-A.; Eriksson Karlstrom, A., Affibody Molecules in Protein Capture Microarrays: Evaluation of Multidomain Ligands and Different Detection Formats. *J. Proteome Res.* 2007, 6 (1), 171-179, DOI: 10.1021/pr060316r
36. Nygren, P. A., Alternative binding proteins: Affibody binding proteins developed from a small three-helix bundle scaffold. *FEBS J.* 2008, 275 (11), 2668-2676, DOI: 10.1111/j.1742-4658.2008.06438.x
37. Miranda, F. F.; Brient-Litzler, E.; Zidane, N.; Pecorari, F.; Bedouelle, H., Reagentless fluorescent biosensors from artificial families of antigen binding proteins. *Biosens. Bioelectron.* 2011, 26 (10), 4184-4190, DOI: 10.1016/j.bios. 2011.04.030
38. Traxlmayr, M. W.; Kiefer, J. D.; Srinivas, R. R.; Lobner, E.; Tisdale, A. W.; Mehta, N. K.; Yang, N. J.; Tidor, B.; Wittrup, K. D., Strong Enrichment of Aromatic Residues in Binding Sites from a Charge-neutralized Hyperthermostable Sso7d Scaffold Library. *J. Biol. Chem.* 2016, 291 (43), 22496-22508, DOI: 10.1074/jbc.M116.741314
39. Miller, E. A.; Traxlmayr, M. W.; Shen, J.; Sikes, H. D., Activity-based assessment of an engineered hyperthermophilic protein as a capture agent in paper-based diagnostic tests. *Mol. Syst. Des. Eng.* 2016, 1 (4), 377-381, DOI: 10.1039/C6ME00032K
40. Zhao, N.; Spencer, J.; Schmitt, M. A.; Fisk, J. D., Hyperthermostable binding molecules on phage: Assay components for point-of-care diagnostics for active tuberculosis infection. *Anal. Biochem.* 2017, 521, 59-71, DOI: 10.1016/j.ab. 2016.12.021
41. Kalichuk, V.; Béhar, G.; Renodon-Corniére, A.; Danovski, G.; Obal, G.; Barbet, J.; Mouratou, B.; Pecorari, F., The archaeal "7 kDa DNA-binding" proteins: extended characterization of an old gifted family. *Sci. Rep.* 2016, 6, 37274, DOI: 10.1038/srep37274
42. Baumann, H.; Knapp, S.; Lundbáck, T.; Ladenstein, R.; Hard, T., Solution structure and DNA-binding properties of a thermostable protein from the archaeon *Sulfolobus solfataricus*. *Nat. Struct. Biol.* 1994, 1, 808, DOI: 10.1038/nsb1194-808
43. Traxlmayr, M. W.; Kiefer, J. D.; Srinivas, R. R.; Lobner, E.; Tisdale, A. W.; Mehta, N. K.; Yang, N. J.; Tidor, B.; Wittrup, K. D. Strong Enrichment of Aromatic Residues in Binding Sites from a Charge-neutralized Hyperthermostable Sso7d Scaffold Library. *J Biol Chem,* 2016, 291 (43): 22496-22508.
44. Ahlgren, S.; Wallberg, H.; Tran, T. A.; Widstrom, C.; Hjertman, M.; Abrahmsen, L.; Berndorff, D.; Dinkelborg, L. M.; Cyr, J. E.; Feldwisch, J.; Orlova, A.; Tolmachev, V. Targeting of HER2-expressing tumors with a site-specifically 99mTc-labeled recombinant affibody molecule, ZHER2:2395, with C-terminally engineered cysteine. *J. Nucl. Med.* 2009, 50(5): 781-789.
45. Orlova, R. A.; Rosik, D.; Sandstrom, M.; Lundgvist, H.; Einarsson, L.; Tolmachev, V. Evaluation of [(111/114m)ln]CHX-A"-DPTA-ZHER2:342, an affibody ligand conjugate for targeting of HER2-expressing malignant tumors. *Q J Nucl Med Mol Imaging* 2007, 51(4): 314-323.
46. Tran, T.; Englfeldt, T.; Orlova, A.; Sandstrom, M.; Felwisch, J.; Abrahmsen, L.; Wennborg, A.; Tolmachev, V.; Karlstrom, A. E. (99m)Tc-maEEE-Z(HER2:342), an Affibody molecule-based tracer for the detection of HER2 expression in malignant tumors. *Bioconjug Chem.* 2007, 18(6): 1956-1964.
47. Desmet, J.; Verstraete, K.; Bloch, Y.; Lorent, E.; Wen, Y.; Devreese, B.; Vandenbroucke, K.; Loverix, S.; Hettmann, T.; Deroo, S.; Somers, K.' Henderikx, P.; Lasters, I.; Savvides, S. N. Structural basis of IL-23 antagonism by an Alphabody protein scaffold. *Nat Comm,* 2014, 5: 5237.
48. Chiu, M. and Gilliland, G. Engineered antibody therapeutics. *Curr Opin Struc Biol,* 2016, 38: 163-173.
49. Frenzel, A.; Hust, M.; Schirrmann, T. Expression of Recombinant Antibodies. *Front Immunol,* 2013, 4: 217.
50. Hudson, P. J.; Kortt, A. A. High avidity scFv multimers: diabodies and triabodies. *J Immunol Methods,* 1999, 231: 177.
51. Hu, S.; Shively, L.; Raubitschek, A.; Sherman, M.; Williams, L. E.; Wong, J. Y.; Shively, J. E.; Wu, A. M. Minibody: a novel engineered anti-carcinoembryonic antigen antibody fragment (single-chain Fv-CH$_3$) which exhibits rapid, high-level targeting of xenografts. *Cancer Res.* 1996, 56(13): 3055-3061.
52. Choi, B. D.; Kuan, C. T.; Cai, M.; Archer, G. E.; Mitchell, D. A.; Gedeon, P. C.; Sanchez-Perez, L.; Pastan, I.; Bigner, D. D.; Sampson, J. H. Systemic administration of a bispecific antibody targeting EGFRvIII successfully treats intracerebral glioma. *PNAS.* 2013, 110(1): 270-275.
53. Fournier, P.; Schirrmacher, V. Bispecific antibodies and trispecific immunocytokines for targeting the immune system against cancer: preparing for the future. *BioDrugs.* 2013, 27: 35.
54. Zitron, I. M.; Thakur, A.; Norkina, O.; Barger, G. R.; Lum, L. G.; Mittal, S. Targeting and killing of glioblastoma with activated T cells armed with bispecific antibodies. *BMC Cancer* 2013, 13.
55. Pant, N.; Hultberg, A.; Zhao, Y., Svensson, L.; Pan-Hammarstrom, Q.; Johansen, K.; Pouwels, P. H.; Ruggeri, F. M.; Hermans, P.; Frenken, L.; Boren, T.; Marcotte, H.; Hammarstrom, L. Lactobacilli expressing variable domain of llama heavy-chain antibody fragments (lactobodies) confer protection against rotavirus-induced diarrhea. *J Infect. Dis.* 2006, 194(11): 1580-1588.
56. Gonzalez-Sapienza, G.; Rossotti, M.; Tabaraes-da Rosa, S. Single-Domain Antibodies as Versatile Affinity Reagents for Analytic and Diagnostic Applications. *Front Immunol,* 2017.
57. Chen, X.; Zaro, J. L.; Shen, W. C. Fusion protein linkers: property, design, and functionality. *Adv Drug Deliv Rev* 2013, 65 (10): 1357-1369.
58. Ackerman, M.; Levary, D.; Tobon, G.; Hackel, B.; Orcutt, K. D.; Wittrup, K. D. Highly avid magnetic bead capture: an efficient selection method for de novo protein engineering utilizing yeast surface display. *Biotechnol. Prog.,* 2009, 25(3): 774-83.
59. Chao, G.; Lau, W. L.; Hackel, B. J.; Sazinsky, S. L.; Lippow, S. M.; Wittrup, K. D. Isolating and engineering human antibodies using yeast surface display. *Nat. Prot.* 2006, 1(2): 755-768.
60. Zhu, L.; Wang, K.; Cui, J.; Liu, H.; Bu, X.; Ma, H.; Wang, W.; Gong, H.; Lausted, C.; Hood, L.; Yang, G.; Hu, Z. Label-Free Quantative Detection of Tumor-Derived Exosomes through Surface Plasmon Resonance Imaging. *Anal Chem,* 2014, 86: 8857-8864.
61. Vuoriluoto, M.; Orlema, H.; Zhu, B.; Johansson, L. S.; Rojas, O. J. Control of Protein Affinity of Bioactive Nanocellulose and Passivation Using Engineered Block and Random Copolymers. *ACS Appl Mater Interfaces,* 2016, 8(8): 5668-5678.
62. Chang, D.; Huang, A.; Olsen, B. D., Kinetic Effects on Self-Assembly and Function of Protein—Polymer Bioconjugates in Thin Films Prepared by Flow *Coating. Macromol. Rapid Commun.* 2017, 38 (1), 1600449, DOI: 10.1002/marc. 201600449
63. Dixit, C. K.; Vashist, S. K.; MacCraith, B. D.; O'Kennedy, R., Multisubstrate-compatible ELISA procedures for rapid and high-sensitivity immunoassays. *Nat. Prot.* 2011, 6, 439, DOI: 10.1038/nprot. 2011.304
64. Balsara, N. P.; Perahia, D.; Safinya, C. R.; Tirrell, M.; Lodge, T. P., Birefringence detection of the order-to-disorder transition in block copolymer liquids. *Macromolecules* 1992, 25 (15), 3896-3901, DOI: 10.1021/ma00041a011
65. Olsen, B. D.; Segalman, R. A., Phase Transitions in Asymmetric Rod-Coil Block Copolymers. *Macromolecules* 2006, 39 (20), 7078-7083, DOI: 10.1021/ma060994z
66. Boutris, C.; Chatzi, E. G.; Kiparissides, C., Characterization of the LCST behaviour of aqueous poly(N-isopropylacrylamide) solutions by thermal and cloud point techniques. *Polymer* 1997, 38 (10), 2567-2570, DOI: 10.1016/S0032-3861(97)01024-067.
67. Schneider, C. A.; Rasband, W. S.; Eliceiri, K. W., NIH Image to ImageJ: 25 years of image analysis. *Nat. Methods* 2012, 9, 671, DOI: 10.1038/nmeth. 2089
68. Olsen, B. D.; Shah, M.; Ganesan, V.; Segalman, R. A., Universalization of the Phase Diagram for a Model Rod-Coil Diblock Copolymer. *Macromolecules* 2008, 41 (18), 6809-6817, DOI: 10.1021/ma800978c
69. Xia, Y.; Yin, X.; Burke, N. A. D.; Stover, H. D. H., Thermal Response of Narrow-Disperse Poly(N-isopropylacrylamide) Prepared by Atom Transfer Radical *Polymerization. Macromolecules* 2005, 38 (14), 5937-5943, DOI: 10.1021/ma050261z
70. Lessard, D. G.; Ousalem, M.; Zhu, X. X., Effect of the molecular weight on the lower critical solution temperature of poly(N,N-diethylacrylamide) in aqueous solutions. *Can. J. Chem.* 2001, 79 (12), 1870-1874, DOI: 10.1139/v01-180
71. Lodge, T. P.; Hanley, K. J.; Pudil, B.; Alahapperuma, V., Phase Behavior of Block Copolymers in a Neutral Solvent. *Macromolecules* 2003, 36 (3), 816-822, DOI: 10.1021/ma0209601
72. Lodge, T. P.; Pudil, B.; Hanley, K. J., The Full Phase Behavior for Block Copolymers in Solvents of Varying Selectivity. *Macromolecules* 2002, 35 (12), 4707-4717, DOI: 10.1021/ma0200975
73. Hanley, K. J.; Lodge, T. P.; Huang, C.-I., Phase Behavior of a Block Copolymer in Solvents of Varying Selectivity. *Macromolecules* 2000, 33 (16), 5918-5931, DOI: 10.1021/ma000318b
74. McConnell, G. A.; Gast, A. P., Melting of Ordered Arrays and Shape Transitions in Highly Concentrated Diblock Copolymer Solutions. *Macromolecules* 1997, 30 (3), 435-444, DOI: 10.1021/ma961241n
75. Lai, C.; Russel, W. B.; Register, R. A., Scaling of Domain Spacing in Concentrated Solutions of Block Copolymers in Selective Solvents. *Macromolecules* 2002, 35 (10), 4044-4049, DOI: 10.1021/ma0122223
76. Lodge, T. P.; Hamersky, M. W.; Hanley, K. J.; Huang, C.-I., Solvent Distribution in Weakly-Ordered Block Copolymer Solutions. *Macromolecules* 1997, 30 (20), 6139-6149, DOI: 10.1021/ma970720z
77. Shibayama, M.; Hashimoto, T.; Hasegawa, H.; Kawai, H., Ordered structure in block polymer solutions. 3. Concentration dependence of microdomains in nonselective solvents. *Macromolecules* 1983, 16 (9), 1427-1433, DOI: 10.1021/ma00243a005
78. Hashimoto, T.; Shibayama, M.; Kawai, H., Ordered structure in block polymer solutions. 4. Scaling rules on size of fluctuations with block molecular weight, concentration, and temperature in segregation and homogeneous regimes. *Macromolecules* 1983, 16 (7), 1093-1101, DOI: 10.1021/ma00241a010
79. Dubacheva, G. V.; Araya-Callis, C.; Geert Volbeda, A.; Fairhead, M.; Codée, J.; Howarth, M.; Richter, R. P., Controlling Multivalent Binding through Surface Chemistry: Model Study on Streptavidin. *J. Am. Chem. Soc.* 2017, 139 (11), 4157-4167, DOI: 10.1021/jacs. 7b00540
80. Pérez-Luna, V. H.; O'Brien, M. J.; Opperman, K. A.; Hampton, P. D.; Lopez, G. P.; Klumb, L. A.; Stayton, P. S., Molecular Recognition between Genetically Engineered Streptavidin and Surface-Bound Biotin. *J. Am. Chem. Soc.* 1999, 121 (27), 6469-6478, DOI: 10.1021/ja983984p
81. DeMonte, D.; Drake, E. J.; Lim, K. H.; Gulick, A. M.; Park, S., Structure-based engineering of streptavidin monomer with a reduced biotin dissociation rate. *Proteins: Struct., Funct., Bioinf.* 2013, 81 (9), 1621-1633, DOI: 10.1002/prot. 24320
82. Merlino, A.; Graziano, G.; Mazzarella, L., Structural and dynamic effects of α-Helix deletion in Sso7d: Implications for protein thermal stability. *Proteins: Struct., Funct., Bioinf.* 2004, 57 (4), 692-701, DOI: 10.1002/prot. 20270
83. Paloni, J. M.; Miller, E. A.; Sikes, H. D.; Olsen, B. D., Improved Ordering in Low Molecular Weight Protein—Polymer Conjugates Through Oligomerization of the Protein Block. Biomacromolecules 2018, 19 (9), 3814-3824, DOI: 10.1021/acs.biomac. 8b00928

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

The invention claimed is:

1. A protein-polymer conjugate comprising an oligomer of an engineered binding protein linked to a polymer,
   wherein the engineered binding protein is a Sso7d protein, a Sac7d protein, an engineered coiled-coil protein, or an antibody variable domain,
   wherein the protein-polymer conjugate self-assembles into a lamellar nanostructure, and
   wherein:
   (i) the protein-polymer conjugate forms a thin film that comprises at least 2-fold more binding sites in an area of the protein-polymer conjugate compared to a monolayer of the engineered binding protein of the same size as the area of the protein-polymer conjugate; and/or
   (ii) the unit spacing between repeating domains of the protein-polymer conjugates is less than 30 nm.

2. The protein-polymer conjugate of claim 1, wherein:
   (i) the polymer comprises a poly(N-isopropylacrylamide) (PNIPAM) block, a poly(hydroxypropyl acrylate) (PHPA) block, a poly(oligoethylene glycol acrylate) (POEGA) block, or a poly(3-(2-methacroyloyethyl)-N,N-dimethylammonio)propane sulfonate) (PDMAS) block; and/or
   (ii) the protein oligomers comprise trimers and/or tetramers of the engineered binding protein.

3. The protein-polymer conjugate of claim 1, wherein:
   (i) the Sso7d protein is a recombinant (rc) rcSso7d protein engineered to bind a ligand;
   (ii) the rcSso7d protein comprises at least 85% of the amino acid sequence of SEQ ID NO: 2 from *Sulfolobus solfataricus*;

(iii) the coiled-coil protein is a three-helix bundle protein;
(iv) the antibody variable domain is a VH, VHH, and/or VL domain; and/or
(v) the engineered binding protein is an oligomer of an antibody variable domain that is an scFv.

4. The protein-polymer conjugate of claim 1, wherein the binding proteins are linked by peptide linkers, wherein the peptide linkers comprise Gly-Ser linkers.

5. A biosensor comprising the protein-polymer conjugate of claim 1 bound to a surface, wherein:
(i) the protein-polymer conjugate forms a thin film on the surface that comprises at least 2-fold more binding sites in an area of the protein-polymer conjugate compared to a monolayer of the engineered binding protein of the same size as the area of the protein-polymer conjugate;
(ii) the limit of detection for binding by the protein is between 100 nM and 300 nM;
(iii) the surface is a semiconductor material, a quartz material, a glass material, a paper material, a cellulose material, or a nitrocellulose material; and/or
(iv) the unit spacing between repeating domains of protein-polymer conjugates on the surface is less than 30 nm.

6. The biosensor of claim 5, wherein:
the surface is silicon.

7. A method for detecting a ligand of interest, the method comprising:
(a) contacting the biosensor of claim 5 with a sample comprising a ligand of interest, wherein the engineered binding protein oligomer binds the ligand of interest; and
(b) detecting the ligand of interest bound by the engineered binding protein oligomer.

8. The method of claim 7, wherein:
(i) the protein-polymer conjugate is in molar excess of the ligand of interest;
(ii) the ligand of interest is streptavidin or monomeric streptavidin;
(iii) the sample is a biological sample from a subject;
(iv) the unit spacing between repeating domains of engineered binding protein oligomers on the surface is less than 50 nm; and/or
(v) the molecular weight of the ligand of interest is less than 50 kDa.

9. A method for detecting a ligand of interest, the method comprising:
(a) contacting the protein-polymer conjugate of claim 1 with a sample comprising a ligand of interest, wherein the ligand of interest binds to the engineered binding protein oligomer and forms a complex;
(b) contacting the complex with a surface for a time sufficient for the complex to bind the surface; and
(c) detecting the ligand of interest bound by the engineered binding protein oligomer.

10. The method of claim 9, wherein:
(i) the protein-polymer conjugate is in solution;
(ii) the sample is a biological sample;
(iii) the protein-polymer conjugate is in molar excess of the ligand of interest;
(iv) the ligand of interest is streptavidin or monomeric streptavidin;
(v) the surface is a semiconductor material, a quartz material, a glass material, a paper material, a cellulose material, or a nitrocellulose material;
(vi) wherein the surface is silicon;
(vii) the engineered binding protein oligomer binds to streptavidin or monomeric streptavidin;
(viii) the limit of detection for binding by the protein is between 100 nM and 300 nM;
(ix) unit spacing between repeating domains of the engineered binding protein oligomers in the complex is less than 50 nm; and/or
(x) the molecular weight of the ligand of interest is less than 50 kDa.

11. The method of claim 9, wherein the sample is a biological sample from a subject, wherein the subject has or is suspected of having an infectious disease.

12. A kit for assessing a presence or amount of a ligand, the kit comprising a container containing the protein-polymer conjugate of claim 1, further comprising a surface for binding the protein-polymer conjugate.

13. The kit of claim 12, wherein:
(i) the protein-polymer conjugate is bound to the surface;
(ii) the protein-polymer conjugate is not bound to the surface; and/or
(iii) the surface is a semiconductor material, a quartz material, a glass material, a paper material, a cellulose material, or a nitrocellulose material.

14. A method of detecting a ligand of interest, the method comprising:
(a) contacting the biosensor of claim 5 with a sample comprising a ligand of interest, wherein the ligand of interest binds to the protein-polymer conjugate and forms a complex; and
(b) detecting the ligand of interest bound by the protein-polymer conjugate.

15. The method of claim 14 wherein the sample is a biological sample, wherein the biological sample is from a subject having or suspected of having an infectious disease.

16. The method of claim 15, wherein:
(i) the protein-polymer conjugate is in molar excess of the ligand of interest;
(ii) the ligand of interest is streptavidin or monomeric streptavidin; and/or
(iii) the limit of detection is 5 nM-300 nM.

17. The protein-polymer conjugate of claim 3, wherein the ligand is streptavidin or a monomeric variant of streptavidin.

18. The method of claim 10, wherein the solution comprises a buffer.

* * * * *

UNITED STATES PATENT AND TRADEMARK OFFICE
CERTIFICATE OF CORRECTION

| | |
|---|---|
| PATENT NO. | : 11,598,769 B2 |
| APPLICATION NO. | : 16/523209 |
| DATED | : March 7, 2023 |
| INVENTOR(S) | : Bradley David Olsen et al. |

It is certified that error appears in the above-identified patent and that said Letters Patent is hereby corrected as shown below:

In the Claims

At Column 86, Claim 17, Lines 50-52:
"The protein-polymer conjugate of claim 3, wherein the ligand is streptavidin or a monomeric variant of streptavidin."
Should read:
--The protein-polymer conjugate of claim 3, wherein the rcSso7d protein is engineered to bind a ligand and wherein the ligand is streptavidin or a monomeric variant of streptavidin.--

At Column 86, Claim 18, Lines 53-54:
"The method of claim 10, wherein the solution comprises a buffer."
Should read:
--The method of claim 10, wherein the protein-polymer conjugate is in solution and wherein the solution comprises a buffer.--

Signed and Sealed this
Sixteenth Day of May, 2023

Katherine Kelly Vidal
*Director of the United States Patent and Trademark Office*